(12) United States Patent
Luo

(10) Patent No.: US 12,090,279 B2
(45) Date of Patent: Sep. 17, 2024

(54) SYSTEM FOR CIRCADIAN RHYTHM ADJUSTMENT

(71) Applicant: LumosTech, Inc., Irvine, CA (US)

(72) Inventor: Biquan Luo, San Francisco, CA (US)

(73) Assignee: LumosTech, Inc., Irvine, CA (US)

( * ) Notice: Subject to any disclaimer, the term of this patent is extended or adjusted under 35 U.S.C. 154(b) by 180 days.

(21) Appl. No.: 17/933,240

(22) Filed: Sep. 19, 2022

(65) Prior Publication Data

US 2023/0013810 A1 Jan. 19, 2023

Related U.S. Application Data

(63) Continuation of application No. 17/548,206, filed on Dec. 10, 2021, now Pat. No. 11,446,465, which is a continuation-in-part of application No. 16/810,800, filed on Mar. 5, 2020, now abandoned, which is a continuation-in-part of application No. 16/803,961, filed on Feb. 27, 2020, now Pat. No. 11,666,485.

(60) Provisional application No. 63/124,096, filed on Dec. 11, 2020, provisional application No. 62/835,473, filed on Apr. 17, 2019, provisional application No. 62/814,257, filed on Mar. 5, 2019, provisional application No. 62/812,683, filed on Mar. 1, 2019.

(51) Int. Cl.
*A61M 21/02* (2006.01)
*A61F 9/04* (2006.01)
*A61M 21/00* (2006.01)
*G16H 20/30* (2018.01)
*G16H 40/67* (2018.01)

(52) U.S. Cl.
CPC .............. *A61M 21/02* (2013.01); *A61F 9/04* (2013.01); *G16H 20/30* (2018.01); *G16H 40/67* (2018.01); *A61M 2021/0044* (2013.01); *A61M 2021/0083* (2013.01); *A61M 2205/3306* (2013.01); *A61M 2205/3317* (2013.01); *A61M 2205/583* (2013.01); *A61M 2209/088* (2013.01); *A61M 2230/63* (2013.01)

(58) Field of Classification Search
CPC .......... A61M 21/02; A61M 2021/0044; A61M 2021/0083; A61M 2205/3306; A61M 2205/3317; A61M 2205/583; A61M 2209/088; A61M 2230/63; A61F 9/04
See application file for complete search history.

(56) References Cited

U.S. PATENT DOCUMENTS

| 11,857,731 B2 * | 1/2024 | Guo | A61B 5/4815 |
| 2016/0193442 A1 * | 7/2016 | Adamczyk | A61M 21/02 |
| | | | 600/27 |
| 2021/0205573 A1 * | 7/2021 | Guo | A61M 21/02 |

FOREIGN PATENT DOCUMENTS

WO  WO-2018197243 A1 * 11/2018 ........... A61N 5/0618

* cited by examiner

*Primary Examiner* — Jonathan T Kuo
(74) *Attorney, Agent, or Firm* — Scale LLP

(57) ABSTRACT

Systems and methods for adjusting a user's circadian rhythm are described. In some embodiments, a system may include one or more input modules for collecting data, a light source, a processor system including one or more processors that controls the light source, and a memory system storing one or more machine instructions. The system may be configured to obtain light sensitivity data for a user, compare the user's light sensitivity data against calibration data, and based on at least the light sensitivity data and the calibration data, generate instructions for activating the light source to adjust the user's circadian rhythm.

20 Claims, 20 Drawing Sheets

| 1502 | obtain information relating to the user's circadian rhythm (e.g., information relating to times of sleep and/or wakefulness) |

| 1504 | obtain information relating to one or more anticipated times of sleep and/or wakefulness, for the user, on one or more days |

| 1506 | based on at least the information relating to the user's circadian rhythm, generate a model for estimating the user's circadian rhythm over one or more days, the estimates of the user's circadian rhythm being configured to be adjusted in response to application, or anticipated application, of light by the light source |

| 1508 | based on at least the one or more current, past, and/or anticipated times of sleep and/or wakefulness, generating a model for estimating the user's homeostatic sleep drive over one or more days, the estimates of the user's homeostatic sleep drive being configured to be adjusted in response to changes in the user's sleep and wakefulness times |

| 1510 | generating instructions for activating the light source to adjust the user's circadian rhythm |

| 1512 | based on the generated instructions, activating the light source during a treatment window to adjust the user's circadian rhythm |

| 1514 | obtain updated information relating to circadian rhythm, user feedback, device usage, and/or the efficacy of the instructions for activating the light source during at least the treatment window |

| 1516 | based on the updated information, adjust the instructions for activating the light source to adjust the user's circadian rhythm. |

| 1602 | obtain information relating to the user's circadian rhythm (e.g., information relating to times of sleep and/or wakefulness, and light exposure) with sensors. |

| 1604 | obtain information relating to one or more anticipated times of sleep and/or wakefulness, for the user, on one or more days |

| 1606 | based on at least the information relating to the user's circadian rhythm, generate a model for estimating the user's circadian rhythm over one or more days, the estimates of the user's circadian rhythm being configured to be adjusted in response to application, or anticipated application, of light by the light source (e.g. sleep mask emitting light flashes) |

| 1608 | generating instructions for activating the light source to adjust the user's circadian rhythm |

| 1610 | based on the generated instructions, activating the light source during a treatment window to adjust the user's circadian rhythm |

| 1612 | obtain updated information relating to circadian rhythm via user feedback and/or sensors throughout the treatment process |

| 1614 | based on the updated information, adjust the instructions for activating the light source to adjust the user's circadian rhythm. |

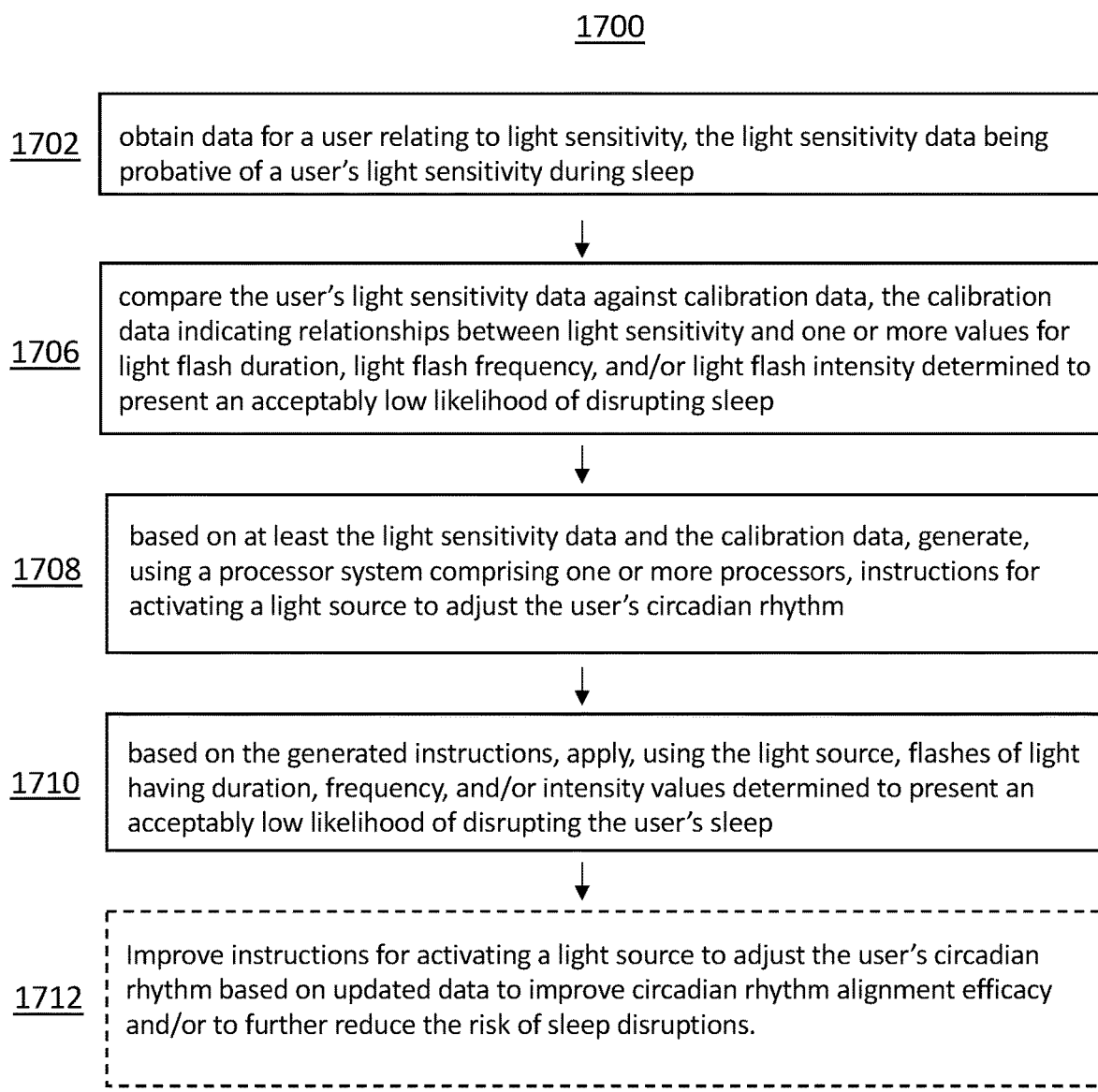

SYSTEM FOR CIRCADIAN RHYTHM ADJUSTMENT

CROSS REFERENCE TO RELATED APPLICATIONS

This application is a continuation of U.S. patent application Ser. No. 17/548,206 (the '206 application), filed Dec. 10, 2021, which claims the benefit of U.S. Provisional Application No. 63/124,096, filed Dec. 11, 2020.

The '206 application is also a continuation-in-part of U.S. patent application Ser. No. 16/810,800, filed Mar. 5, 2020, which is a continuation-in-part of U.S. patent application Ser. No. 16/803,961 (the '961 application), filed Feb. 27, 2020.

The '961 application claims the benefit of U.S. Provisional Application No. 62/835,473, filed Apr. 17, 2019, U.S. Provisional Application No. 62/812,683, filed Mar. 1, 2019, and U.S. Provisional Application No. 62/814,257, filed Mar. 5, 2019.

All of the above applications are incorporated herein by reference.

FIELD OF THE INVENTION

This specification relates to the field of methods and devices for treating and/or adjusting circadian rhythms.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions.

Circadian rhythms are physiological and behavioral oscillations that are normally synchronized with the natural light-dark cycle of the day. Circadian rhythm disorders happen when circadian rhythms are out of synchronization with the actual sleep-wake schedules. Disruptions in the circadian rhythm or misalignments of the circadian rhythm with a user's schedule, such as due to traveling or night shift work requirement can cause difficulty falling asleep, frequent waking up during sleep, and difficulty remaining asleep throughout the intended sleep time. In addition, while awake, circadian rhythm misalignment can lead to impaired cognitive and physiologic performance as well as lethargy, drowsiness, fatigue, and gastrointestinal distress. The circadian rhythms in humans and other mammals are affected by the exposure of the retina to light. Accordingly, it may be desirable to develop device and methods to more effectively treat circadian rhythm disorders by exposing the eyes to light, for example.

SUMMARY

The following description presents a simplified summary in order to provide a basic understanding of some aspects described herein. This summary is not an extensive overview of the claimed subject matter. It is intended to neither identify key or critical elements of the claimed subject matter nor delineate the scope thereof.

In some embodiments, a system for adjusting a user's circadian rhythm may be provided. In some embodiments, the system may include one or more input modules for collecting information relating to a user's sleep and/or wakefulness. The system may also include a light source, a processor system including one or more processors that control the light source, and a memory system storing one or more machine instructions. In some embodiments, the system may be configured to obtain information relating to the user's present circadian rhythm. The system may also be configured to obtain information relating to one or more anticipated times of sleep and/or wakefulness, for the user, on one or more days. Based on at least the information relating to the user's present circadian rhythm, the system may generate a model for estimating the user's circadian rhythm over one or more days. The estimates of the user's circadian rhythm may be configured to be adjusted in response to application, or anticipated application, of light by the light source. Based on at least the one or more anticipated times of sleep and/or wakefulness, the system may be configured to generate a model for estimating the user's homeostatic sleep drive over one or more days. The estimates of the user's homeostatic sleep drive may be configured to be adjusted in response to changes in the user's sleep and wakefulness times. Based on at least the model for estimating the user's circadian rhythm and the model for estimating the user's homeostatic sleep drive, the system may be configured to generate instructions for activating the light source to adjust the user's circadian rhythm.

In some embodiments, a method for adjusting a user's circadian rhythm may be provided. In some embodiments, the method may include one or a combination of the following steps: (i) obtaining information relating to the user's present circadian rhythm; (ii) obtaining information relating to one or more anticipated times of sleep and/or wakefulness, for the user, on one or more days; (iii) based on at least the information relating to the user's circadian rhythm, generating a model for estimating the user's circadian rhythm over one or more days, the estimates of the user's circadian rhythm being configured to be adjusted in response to application, or anticipated application, of light by the light source; (iv) based on at least the one or more anticipated times of sleep and/or wakefulness, generating a model for estimating the user's homeostatic sleep drive over one or more days, the estimates of the user's homeostatic sleep drive being configured to be adjusted in response to changes in the user's sleep and wakefulness times; and (v) based on at least the model for estimating the user's circadian rhythm and the model for estimating the user's homeostatic sleep drive, generating instructions for activating the light source to adjust the user's circadian rhythm.

Further variations encompassed within the systems and methods are described in the detailed description of the invention below.

BRIEF DESCRIPTION OF THE DRAWINGS

In the following drawings like reference numbers are used to refer to like elements. Although the following figures depict various examples of the invention, the invention is not limited to the examples depicted in the figures.

FIG. 12 shows a diagram of how elements of the algorithm interact and what the circadian rhythm adjustment algorithm is optimized for.

FIG. 15 shows an exemplary method for adjusting a user's circadian rhythm.

FIG. 16 shows an exemplary method for adjusting a user's circadian rhythm using input from sensors.

FIG. 17 shows an exemplary method for selecting light treatment parameters.

DETAILED DESCRIPTION

Figure 1:
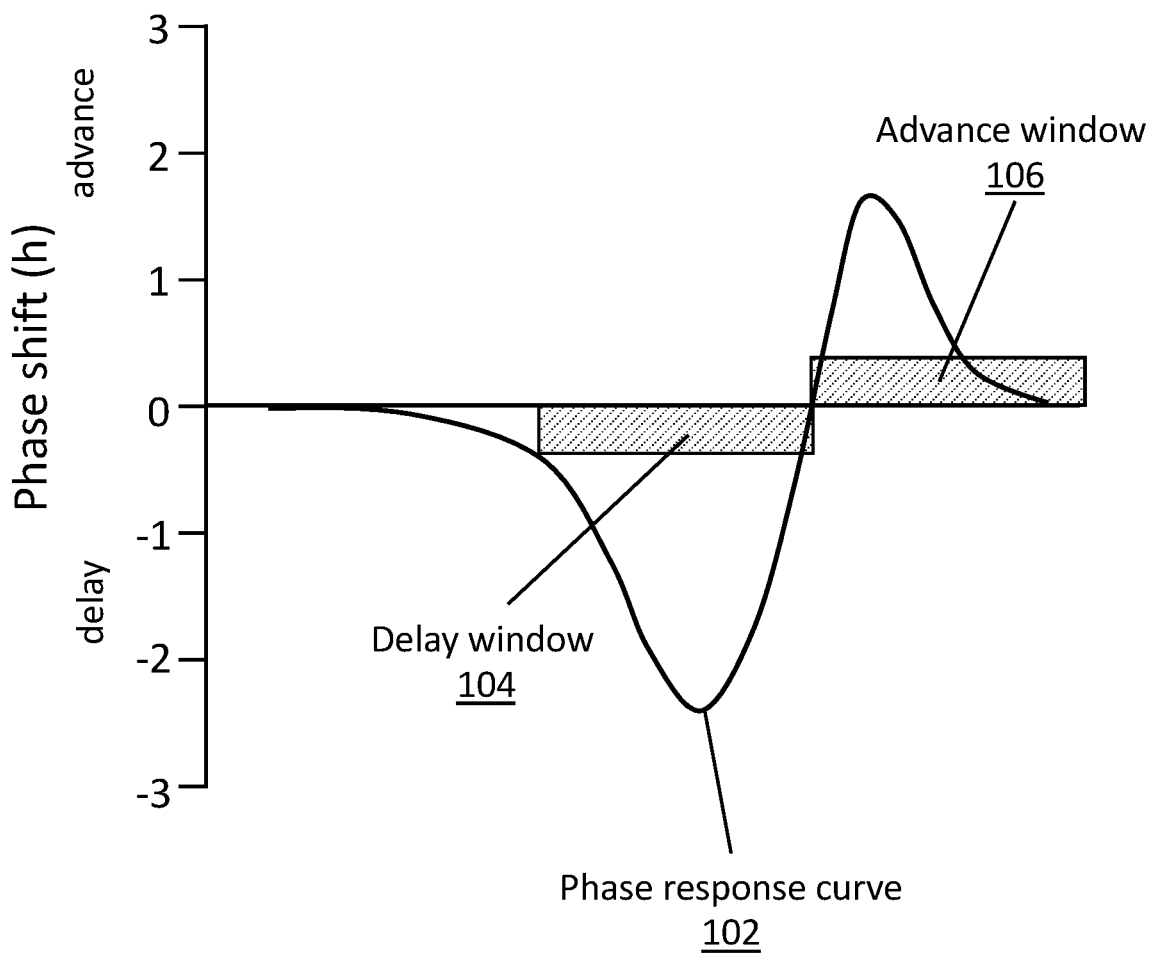
FIG. 1 shows an example of the phase response curve (PRC) for estimating how the circadian phase may be shifted upon light treatment.

Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

Technical Terminology

Some concepts discussed in this specification are as follows,

A. Circadian rhythms: refers to physical, mental, and behavioral changes that follow a 24-hour cycle.

B. Circadian pacemaker: refers to a small group of nerve cells located in the hypothalamus that controls the circadian cycles and influences many physiological and behavioral rhythms occurring over a 24-hour period, including the sleep/wake cycle.

C. Homeostatic sleep drive: also referred as sleep drive or sleep pressure, which refers to the drive to sleep that is influenced by the duration of wakefulness. Homeostatic sleep drive/pressure can be understood as the hunger for sleep.

D. Process C: refers to a process controlled by the circadian pacemaker in sleep regulation.

E. Process S: refers to a sleep regulation process that represents the homeostatic sleep drive.

F. Advance the sleep phase: refers to shifting the wake up time to earlier in the morning or an earlier time.

G. Delay the sleep phase: refers to shifting the wake up time to later in the morning or a later time.

H. Zeitgeber: refers to physical and social events which entrain the circadian clock. Light is an entrainer.

K. Entrainment: refers to the synchronization or alignment of the internal biological clock rhythm, including its phase and period, to external time cues, such as the natural dark-light cycle.

Overview

Embodiment of a circadian rhythm adjustment system have been disclosed in U.S. patent application Ser. No. 16/810,800, which is incorporated herein by reference in its entirety. The circadian rhythm adjustment system described in this specification is an improvement of the system described in U.S. patent application Ser. No. 16/810,800. Embodiments of the system described in this specification may include: (1) data collection mechanisms including software, hardware, and/or lab assays, (2) logic (e.g., software or hardware) for adjusting the circadian rhythm that is based on the prediction of not only the circadian phases but also the homeostatic sleep drive, both of which are guided by mathematical models, user inputs, and environmental data, and data obtained from lab studies (3) circadian rhythm adjustment hardware devices, which may incorporate logic modules, and optionally processors, sensors, light sources and other components, (4) form factor (e.g. a sleep mask) that delivers the circadian rhythm adjustment treatment. In order to generate a circadian-shifting treatment program, embodiments of the system described in this specification may estimate the current circadian phase and the target circadian phase by implementing one or more factors for sleep regulation that affects both the circadian rhythms and the homeostatic sleep drive as part of its circadian-adjustment algorithms. Data collected from user input, sensors in device, lab assays, and/or third party sources may be used as both input of the circadian clock adjustment models and/or a basis for modifying the models (e.g., automatically). A device separating from the circadian rhythm adjustment device, for example, an environmental light sensor that may or may not be wearable, may be used to collect data from the user or the environment, which may provide input for the circadian rhythm adjustment models. Based on at least one algorithm that predicts opportune times for applying therapy, circadian rhythm adjustment programs that include light therapy parameters (e.g. using light flashes or other forms of light) with or without other stimulation or behavioral suggestions may be generated by computation, which may then be executed through a circadian rhythm adjustment hardware device (for example, a sleep mask with electronics that delivers light flashes to shift circadian clocks).

In one embodiment, a system is designed to treat/prevent circadian rhythm misalignment by actively shifting the circadian phase of the user during sleep at night or during the daytime. In an embodiment, the user may use light flashes while the user is sleeping, to adjust the user's circadian rhythm. As a result of using light pulses, and as a result of light pulses being less invasive and less disruptive to sleep, the system may shift circadian rhythm while the users remain sleeping. Compared to other light therapy devices that may shift the circadian rhythm, the use of light pulses is less disruptive to users' day-time activities, also, and is therefore potentially more convenient. More importantly, due to retinal physiology and the sensitivity of the circadian adjustment system in the brain, light flash stimulation at night may be more effective in shifting circadian rhythm than continuous light stimulation during the day.

In some embodiments, the circadian rhythm light program may be generated based on a treatment regimen, which may be controlled by a software program. The system may include software, hardware, a light source, such as an LED, and/or user interface, for example. The system may include a light calculation module, which implements light calculation logic, which determines a pattern of light to apply to the user. Form factors may include sleep masks, and/or different sizes and shapes of other things worn (or that may accompany of a person while sleeping). The system may be integrated into a variety of devices of systems of a variety of sizes and shapes.

In one embodiment of the circadian rhythm adjustment systems, the light calculation logic is based on the phase response curve (PRC) and light flashes are applied during the windows in which circadian clocks can be advanced or delayed by light stimulation. FIG. 1 is an illustration of a PRC (202) in response to light stimulation, and its respective time windows to delay (204) or advance (206) the circadian phase. When sleep consistency is good, meaning that the user has relatively consistent sleep schedules, it is relatively straight forward to estimate the phase-response curve, and therefore relatively straight forward to estimate the treatment windows for phase shifts. In at least one embodiment, the light therapy program may be generated by estimating the treatment window based on simple circadian-estimating models that consider input variables such as current and desired sleep schedules as well as chronotypes. The simple circadian rhythm adjustment usually works quite well. However, predicting the PRC and the corresponding advance or delay windows becomes difficult with irregular schedules. The light therapy treatment windows specified by the circadian rhythm adjustment model based on the PRC alone may be less effective or even counterproductive if part of the light therapy occurs in the delay window and the other part in advance. Moreover, the circadian phase may be shifted in the opposite direction when the advance or delay windows are predicted incorrectly in a circadian rhythm adjustment system when using the circadian rhythm adjustment model based only on estimation of circadian shifts by comparing bedtime or wake time changes and/or time zone changes, which was not previously recognized but later observed in real-life user experience. Additionally, in the case of frequent travel or frequent night shift changes (e.g., for a shift worker) when sleep schedules are subject to irregularity or full entrainment may be challenging to achieved within a desired time, and at times, in some situations, it may be potentially unreliable to use the simple circadian-estimating models to estimate the advance and delay windows. In some circadian rhythm misalignment scenarios, partial or complete sleep deprivation often occurs due to schedule constraints and/or incomplete entrainment, which may further impact how the circadian clocks respond to light and other Zeitgeber input. In additional to circadian rhythm misalignment, there are also times when performances during certain time frames may need to be optimized and prioritized, and operations are highly limited by schedule constraints, for example, in a competition or in a battlefield, which are stressful situations that further add to the complexity of predicting the PRC. Instead of shifting circadian phases to achieve the maximal possible shift, it now recognized that an alternative solution is to shift the circadian phases so the local maximal wakefulness falls in the window when high performances are desired, or the local minimal wakefulness falls out of the window when high performances are desired. At least some embodiments of the system in this disclosure addresses at least some of the above-mentioned circadian rhythm misalignment scenarios in which the effect may be limited by merely calculating circadian phase changes.

The regulation of the sleep-wake cycle is determined by many factors, including genetics, circadian rhythms, homeostatic sleep drive, sleep environment, conscious decisions and behaviors, and so on. The factors that determine the regulation of sleep may play a part in the circadian rhythm misalignment cases described above. Therefore, in at least one embodiment of the circadian rhythm adjustment system, to account for the circadian rhythm misalignment scenarios described above, instead of the circadian rhythm adjustment algorithm only considering circadian rhythm misalignment based only on the estimated PRC based on the current and target sleep times and wake times, a model that includes multiple factors that regulate sleep and wake cycles, such as the circadian rhythm (Process C) and the homeostatic sleep drive (Process S), and based on the combination of multiple factors, the windows of time during which to apply a light treatment in order to shift the circadian rhythm are determined.

The suprachiasmatic nucleus (SCN) is the central circadian pacemaker in the brain. SCN regulates a number of markers for the circadian clock (C), including peripheral oscillators, such as melatonin and core body temperature. Process C refers to a process controlled by the circadian pacemaker in sleep regulation. The homeostatic sleep drive (S) builds up during wakefulness and declines monotonically during sleep. The interaction of Process C and Process S regulates sleep.

Figure 2:
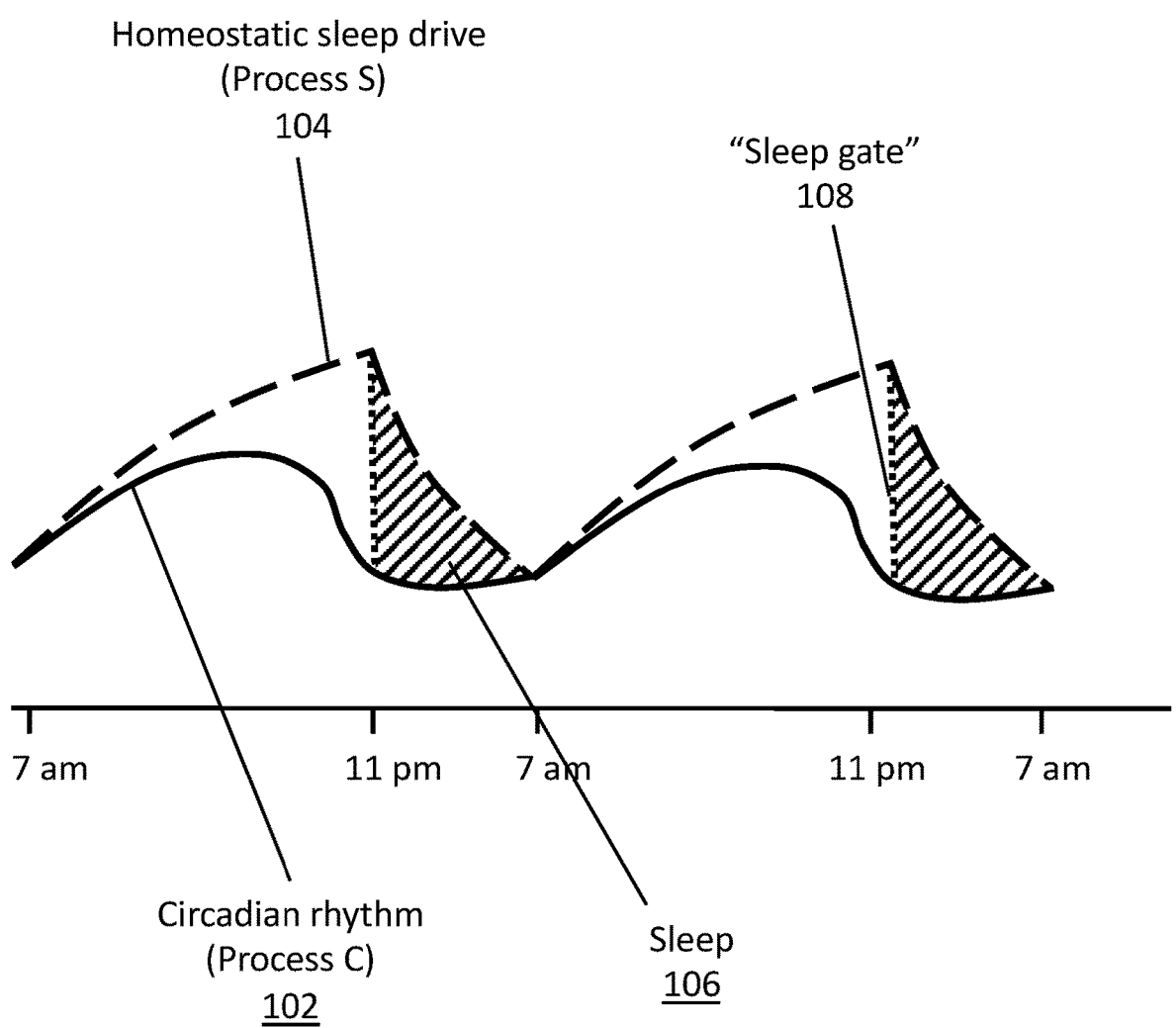
FIG. 2 shows how sleep/wake cycle is regulated by Process C, Process S, and their interactions.

FIG. 2 shows the two-process model of sleep regulation, and how the circadian rhythms and the homeostatic sleep drive together regulate the sleep wake cycle. The lower solid, oscillating line (102) represents Process C, and the upper dash line with sharp angles (104) represents Process S. Sleep switches on when the distance between S and C reaches maximum and switches off when the distance reaches minimum. Sleep gate 108 represents when sleep switches on. The area 106 represents sleep. In some embodiments, a circadian rhythm optimization system may use not only information for circadian rhythm estimation, but also information to calculate the homeostatic sleep drive when computing the sleep and wake cycles for the users.

A circadian rhythm adjustment system may be optimized for at least one of two outcomes, or both if possible: (1) maximizing circadian shifts to achieve the largest overlap between the "sleep" phase of the circadian clock with desired sleep time, and the largest overlap between the "awake" phase of the circadian clock with desired windows of wakefulness; and (2) shifting the circadian phase so the window of high alertness can be best overlapped with desired window when peak performances are required or so the window of low alertness can be best avoided from when peak performances are required. Within each prioritization, the model may have different algorithms to handle different tiers of complexity, including but not limited to: (1) considering circadian rhythm misalignment only; (2) considering the additive effect between circadian rhythm misalignment and the changes of homeostatic sleep pressure with good sleep consistency and/or simple schedule changes that are predictable, regular, or lasts for the amount of time for possible full entrainment to occur with the light therapy; (3) considering the additive effect between circadian rhythm misalignment and the changes of homeostatic sleep pressure with irregular sleep consistency or complicated schedule changes that are changing, unpredictable, or significant over a short amount of time; (4) considering not only the additive effect between circadian rhythm misalignment and the changes of homeostatic sleep pressure, but also the interaction between the two and how one process affects the other when responding to regulatory signals (regulatory signals are signals that regulate the circadian phase and/or the homeostatic sleep drive); (5) besides the circadian rhythm misalignment and homeostatic sleep drive from the schedule changes, also considering other sleep-regulating factors (such as genetic components) that affect the natural circadian clocks or sleep-wake cycles.

Embodiments of the system described in this specification may be useful for treatment of acute circadian rhythm misalignment, for example, during travel or night shift work—or the combination of both. The systems described in this specification may be especially useful for scenarios when a substantial circadian phase shift is required and full entrainment may not be feasible, or when performances during certain time frame need to be optimized and prioritized, for example, for competition or battlefield (however, the system is not limited to such uses and some embodiments may even preclude such uses). Embodiments of this specification may also be useful for treating and preventing chronic circadian rhythm misalignment in night owls, teenagers, and elderly. The circadian rhythm treatment system can be used before, during, and/or after the occurrence of the change of sleep schedules or time zones or anytime when the user would like to improve sleep through optimizing circadian rhythms and alertness.

In this specification, the word "program" may refer to a computer program or other software that the processor runs to turn on and off the light and deliver the treatment plan to the user to adjust and/or regulate the circadian rhythm. The word "program" may also (or alternatively) refer to the treatment plan for adjusting the circadian rhythm (which may be implemented, via a software program). The treatment plan may be implemented by software running on a processor, embedded software, firmware, middleware, and/or hardware. The program used for treating the circadian rhythm disorder may be referred to as a light program, when light is used for treating the circadian rhythm disorder or more generally as a circadian rhythm disorder treatment program. In this specification, "generate" may mean create, design, produce from scratches, or modify from existing version of algorithm, model, or program.

System

Embodiments of the system described in this specification may include: (1) data collection mechanisms including software, hardware, and/or lab assays, (2) logic (e.g., software or hardware) for adjusting the circadian rhythm that is based on the prediction of not only the circadian phases but also the homeostatic sleep drive, both of which are guided by mathematical models, user inputs, and environmental data, and data obtained from lab studies (3) circadian rhythm adjustment hardware device, which may incorporate logic modules, and optionally processors, sensors, and other components, (4) form factor (e.g. a sleep mask) that delivers the circadian rhythm adjustment treatment.

Figure 3A:
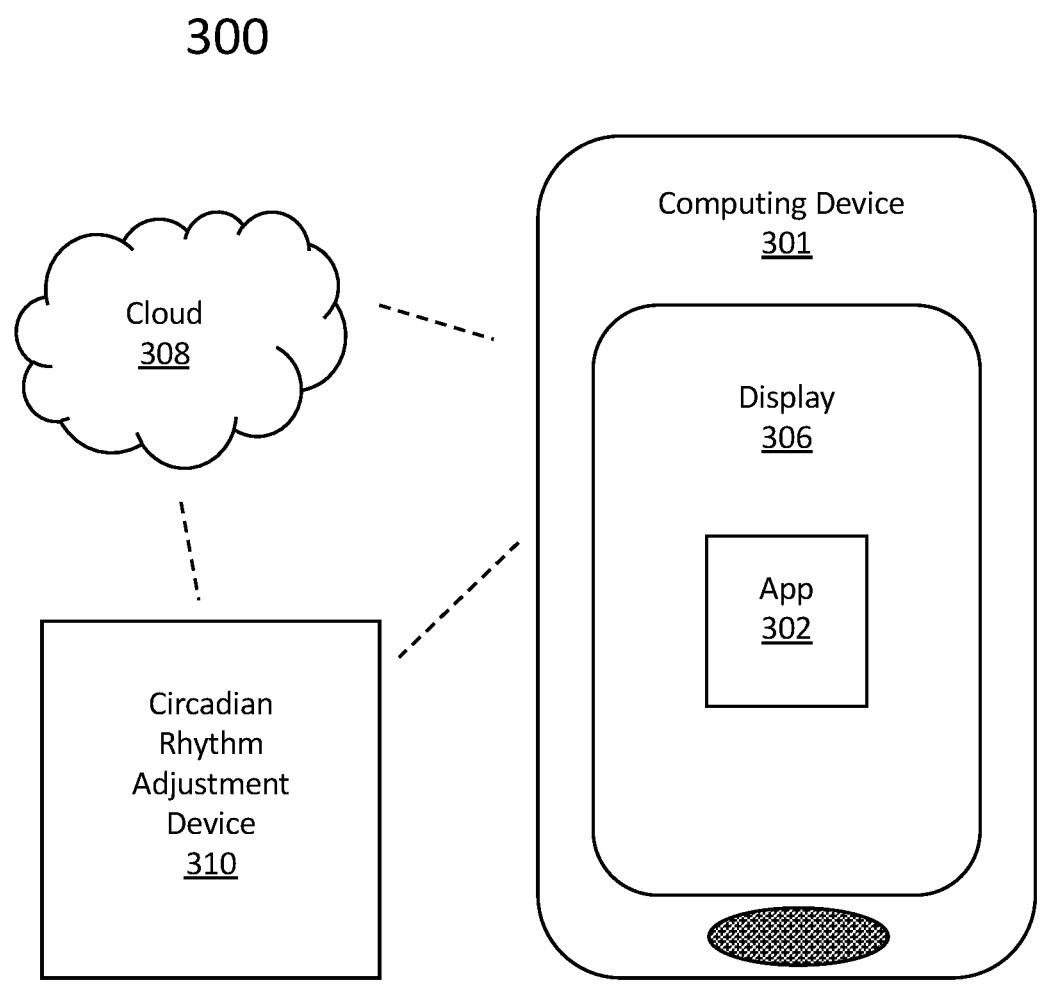
FIG. 3A shows a block diagram of an embodiment of the circadian rhythm therapy system.

FIG. 3A shows a block diagram of an embodiment of a computing system 300. Computing system 300 may include computing device 301, an application 302 and display 306. Computing system 300 may also include cloud 308 and/or circadian rhythm adjustment device 310. Computing device 301 may be a mobile device, Personal Computer (PC), laptop, smart phone, and/or other computing device. Application 302 may reconfigure a computing device 301 to function as a circadian rhythm adjustment apparatus and/or may interface with a circadian rhythm adjustment apparatus. Display 306 may be a touch screen or other display via which the user may view setting and pages generated by application 302 and enter input for configuring the computing device 301 and/or system 300 for adjusting a circadian rhythm. Cloud 308 may include any combination of wide area networks and/or local area networks. Cloud 308 may include one or more servers, computing devices, and/or devices on which an algorithm for determining a circadian rhythm therapy and/or controlling sleep therapy system may reside. Besides storing the data collected from the mobile application 302 and/or from circadian rhythm adjustment device 310, the cloud 308 may run application 302 and/or may run an algorithm based on input from application 302 (which is running of computing device 301), and cloud may send the sleep therapy program to computing device 301 and/or circadian rhythm adjustment device 310. Computing device 301 may communicate with circadian rhythm adjustment device 310, via cloud 308. An example of a circadian rhythm treatment apparatus is a light pulse delivery apparatus, such as a mobile sleep mask, goggles, bedroom lights, and/or other circadian rhythm treatment apparatus (which may deliver light pulses). In one embodiment, user data input, environmental data, and data from the lab may be collected via user interface or set in the backend of the app 302. In another embodiment, in addition to user input or manufacturer's preset via app 302, data used for circadian rhythm calculation may be collected via sensors on the circadian rhythm adjustment device 310. The software may be stored on and run on a mobile device (e.g., a smart phone), a computational device (e.g., a computer), an/or delivered from a server, such as, as a result of the user interacting with a webpage. The software may be located in a light-emitting device (e.g., the sleep mask or a lamp in a bedroom), and the light emitting device may run the program producing the pattern of light used to treat the user. Treatment logic including the mathematical models and the light program algorithms may be implemented on the software within the app 302 on the computing device 300, or the cloud 308, or the combination of both. In one embodiment, part of the light program treatment logic may be implemented in the firmware on the circadian rhythm adjustment device 310. Additionally or alternatively, the light emitting device may respond to signals from a device running the program to produce the pattern of light for treating the user, and thereby the light emitting device may act as the circadian rhythm treatment apparatus. The light emitting device may communicate via a wide area network, such as the Internet, with a server (and/or other devices), and the light emitting device may receive signals, from a server (and/or other devices), directing the light emitting device to flash in a desired pattern to adjust a circadian rhythm. Optionally, the circadian rhythm treatment apparatus may have an Application Program Interface (API), via which another device may control or interface with the circadian rhythm treatment apparatus, allowing the user to adjust the user's circadian clocks, via the API. The circadian rhythm treatment device may communicate with other devices and/or programs, via the API associated with those other devices and/or programs. The circadian rhythm treatment apparatus may interface with a wearable device and/or software applications, or through a program and/or hardware device that controls the collection of Internet of Things (IoT) devices (e.g., a smart home device or a virtual intelligent personal assistant). Alternatively, or additionally, circadian rhythm treatment apparatus may be incorporated into a wearable device and/or software application.

Figure 3B:
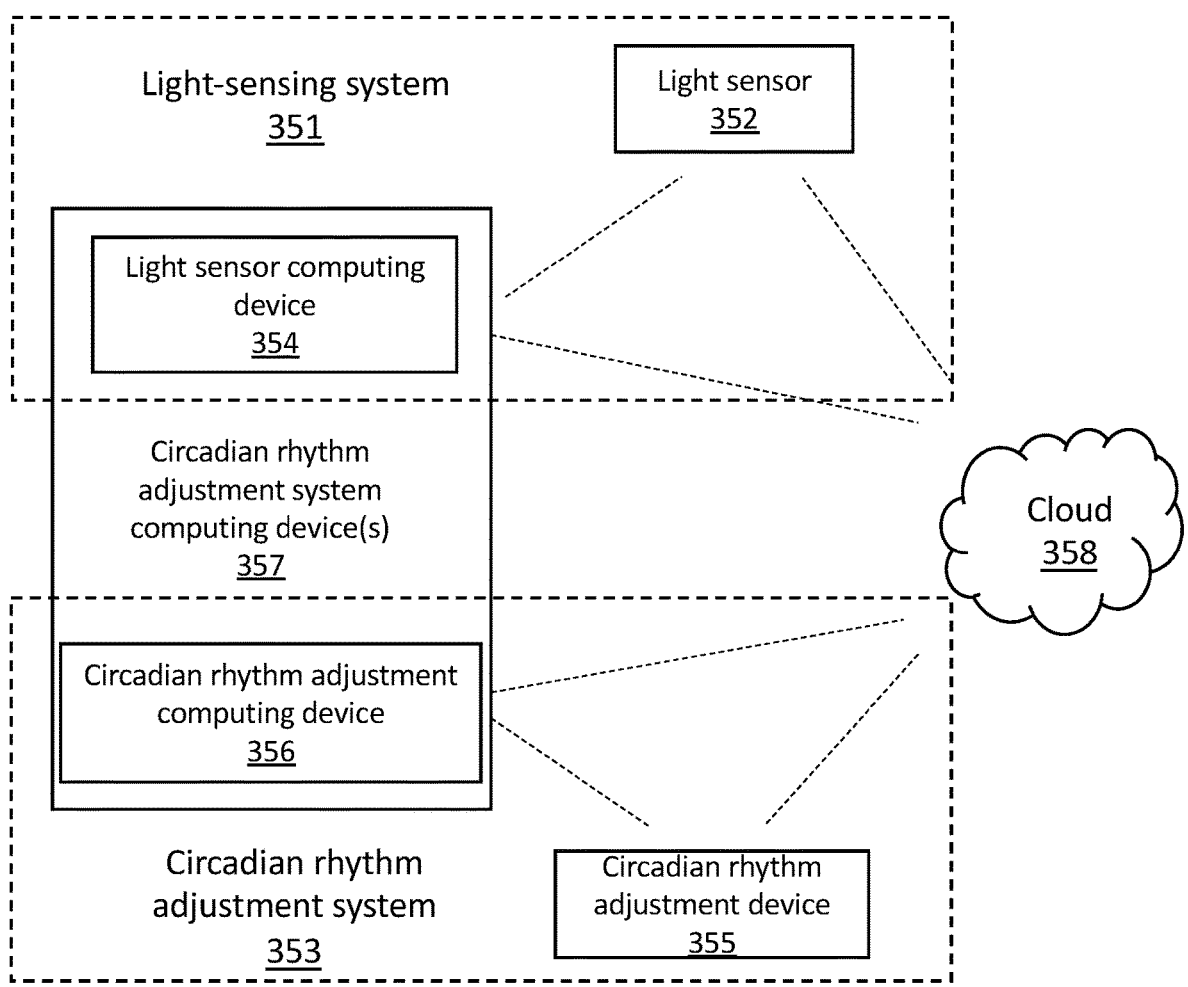
FIG. 3B shows a block diagram of an embodiment of the circadian rhythm therapy system with an environmental light sensing system.

In one embodiment, data collection mechanism may include additional hardware such as a wearable environmental light sensor. FIG. 3B shows a block diagram of an embodiment of the circadian rhythm therapy system 350 that includes both the light sensing system 351 and the circadian rhythm adjustment system 353. The light-sensing system include a light sensor 352 that may or may not be wearable, and the light sensor computing device 354. The circadian rhythm adjustment system includes a computing system 356 to calculate the light program based on the user's circadian clocks and sleep/work schedules, and a device to deliver the treatment light program 355. The light sensor computing device and the circadian rhythm adjustment computing device can be one 357 (e.g. one mobile application) or separate computing devices (e.g. separate mobile applications). The light sensor captures the ambient light data, stores on the device, preliminary processes the data and sends the data to the light sensor computing device. The light sensor computing device then further processes the data and send it to the circadian rhythm adjustment device as the mathematical model input to calculate the user's circadian phase. The mathematical model then output the necessary light program to optimize the user's circadian clocks. Cloud 358 may include any combination of wide area networks and/or local area networks. Cloud may include one or more servers, computing devices, and/or devices on which an algorithm for determining a circadian rhythm therapy and/or controlling sleep therapy system may reside. Circadian rhythm adjustment device may be controlled directly by the circadian rhythm adjustment computing system and/or a device on cloud. Besides storing the data collected from the mobile application and/or from the light sensor and the circadian rhythm adjustment device, the cloud may run application and/or may run an algorithm based on input from application (which is running of computing device), and cloud may send the sleep therapy program to computing device and/or circadian rhythm adjustment device. Computing device may communicate with circadian rhythm adjustment device, via cloud. In one embodiment, the light sensor may have its own computing device 354. In another embodiment, the light sensor computing device 354 and the computing device for the circadian rhythm adjustment device 356 are different parts of the same computing device 357. Treatment logic including the mathematical models and the light program algorithms may be implemented on the software on the computing device 356 or 357, or the cloud 358, or the combination of both. Part of the light program treatment logic may also be implemented in the firmware on the wearable light sensor 352 or 354 and the circadian rhythm adjustment device 355 or 356. In one embodiment, the light sensor 352 and the circadian rhythm adjustment device 355 may be different parts of the same hardware device. The treatment may be a pattern of light pulses and/or other changes in lighting that are delivered to the user, via the circadian rhythm treatment apparatus that delivers the treatment (e.g., via a program that controls the lighting, such as by controlling pulses of light delivered to the user) to effectively treat or prevent circadian rhythm disorders. The treatment may be applied while the subject is asleep and/or awake in the middle of sleep or within 1-2 hours before or after sleep. In at least one embodiment, the program may recommend nap time or caffeine intake to adjust the homeostatic sleep drive and its impact on the sensitivity of circadian system in response to light. There may be an audio component to the circadian rhythm disorder treatment program, which may produce therapeutic sounds, relaxing sounds, and/or pleasant sounds that are synchronized with, and played together with, or independent of, the treatment, such as the pattern of light produced.

In an embodiment, multiple users may use the same device at different times. Each user may have his/her own account with past programs, biological, sleep, homeostasis sleep load profiles, and behavioral profiles. Based on the information collected throughout the time that user uses the circadian rhythm treatment apparatus, the software adjusts and improves itself to provide personalized circadian rhythm disorder treatment program (e.g., light program).

Form Factor

Different form factors (e.g., different types of systems of different sizes and shapes and/or using different patterns of light pulses) may be used to deliver the light programs and adjust circadian rhythms. The circadian treatment device may be mobile, may be a sleep mask or a goggle, a bedside lamp, a hood, a screen, or may not be mobile, such as in-room lighting. In at least one embodiment of the circadian rhythm treatment, the circadian rhythm treatment apparatus can be an eye mask that the user wears while sleeping.

For a smart sleep mask that contains electronic components, it may be desirable to design the mask so that the mask not only has the ability to hold the electronics and to deliver the circadian rhythm disorder treatment program (e.g., a light program), but also the mask should remain in its position on the user's head while in use, as well as being worn in bed comfortably in all, nearly all, or a large variety of sleeping positions, even when incorporating rigid electronics components in the mask. In various embodiments of this specification (but not all embodiments), the system of the mask may be built so as to meet a balance of six features (in addition to other criteria: 1) the mask should is soft enough not to apply an uncomfortable pressure against the user's face when sleeping on the side or face-down; 2) the mask provides enough cushion around the rigid electronics to protect the electronics from environmental damage and to protect the face from pressure from the electronics; 3) while providing enough cushion with soft materials, the mask still breathes (e.g., to help ensure that the electronics cools properly and does not over heat); 4) the eye regions of the mask is be recessed enough and away from the eyes to prevent rubbing against the user's eyes; 5) the mask effectively blocks environmental light; 6) the mask is adjustable to different head sizes and shapes; 7) the mask stays in place to ensure that light programs are received properly by the user throughout the treatment process.

Figure 4A:
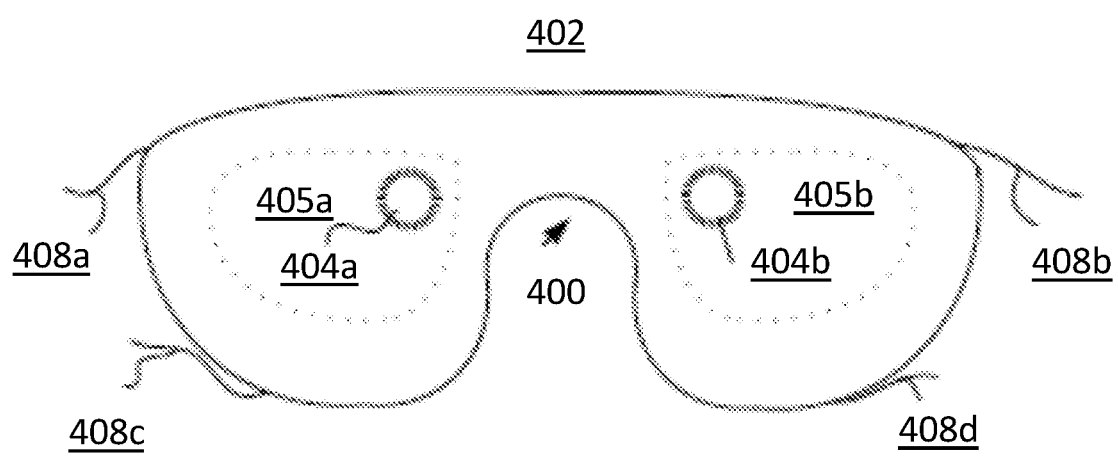
FIG. 4A shows a diagram of an embodiment of the eye mask that delivers the circadian rhythm treatment programs.

FIG. 4A shows an embodiment of system in which the circadian rhythm treatment hardware is built into a sleep mask 400. Mask 400 covers the user's eyes and blocks environmental light from shining on the eyes of the user. Mask 400 may be fashioned from a soft and/or resilient material. Cupped regions 405a and 405b are regions that form cups away from the user's eyes, to ensure that the mask does not cause discomfort by pressing against the user's eyes and/or to ensure that the lights that generate the flashes are a predetermined distance from the eyes to ensure proper illumination of the eyes during a light flash.

Figure 4B:
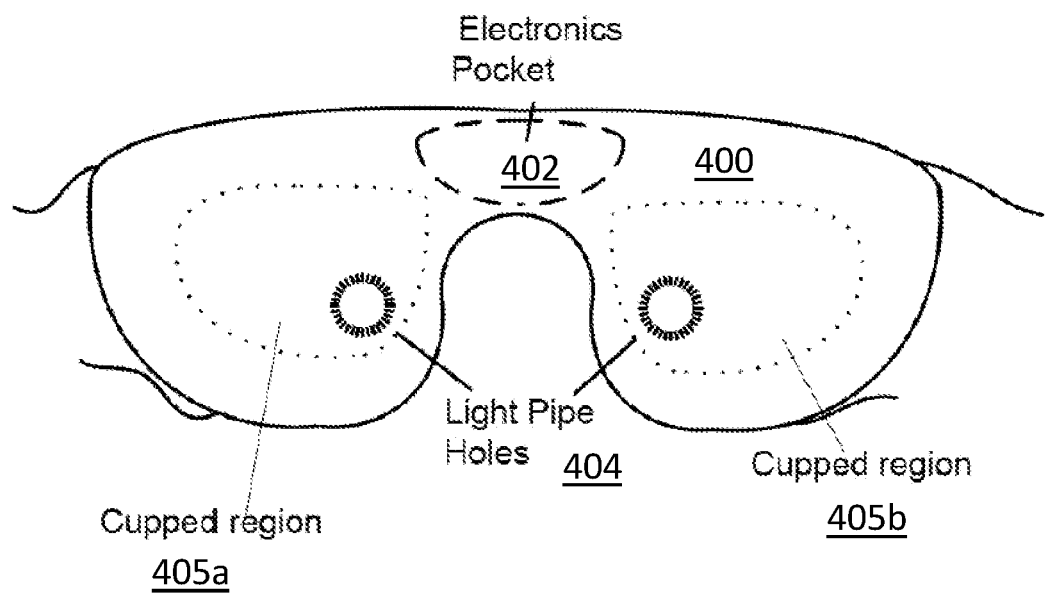
FIG. 4B shows a diagram of an embodiment of the eye mask prior to placing the hardware into the mask.
Figure 4C:
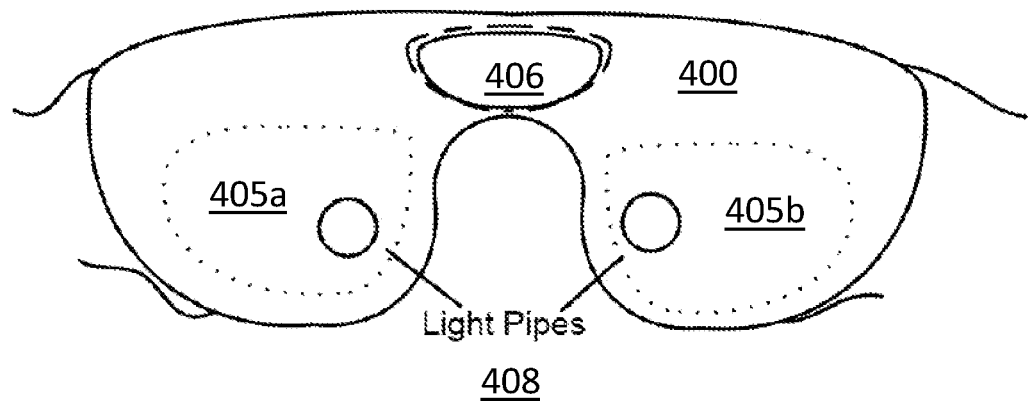
FIG. 4C shows a diagram of an embodiment of the mask of FIG. 4B after the hardware has been installed.
Figure 4D:
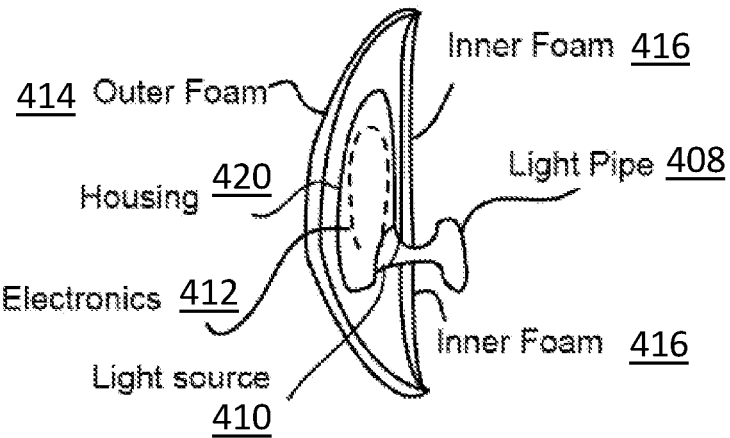
FIG. 4D shows an embodiment of a cross section of the mask with the electronic insert inside the pocket and one light pipe for delivering the light generated to the user.

In one embodiment, the electronics which are responsible for delivering light programs can be inserted into the mask and removed as needed, for example, when the mask needs to be cleaned. FIG. 4B shows a diagram of an embodiment of the mask 400 with empty electronics pocket 402 and light pipe holes 404, prior to placing the hardware into the electronics pocket 402 and the light pipes into light pipe holes 404 of the mask 400. FIG. 4C shows a diagram of an embodiment of the mask of FIG. 4B after the hardware, electronics 406 and light pipes 408 have been installed. Light pipe holes 404 are regions where lights and/or light pipes are placed for illuminating the user's eyes with light flashes, prior to placing the hardware into the electronics pocket 402 and the light pipes into light pipe holes 404 of the mask 400. FIG. 4D shows that light pipe 408 may be connected to an LED (or other light source 410) and/or other electronics 412 on one side of the mask and light pipe for delivering the light generated to the user. The light pipe 408 has an enlarged part at the end in the shape of a button that goes through the light pipe hole on the inner side of the eye mask to hold the electronics and the mask together tightly in the right place. Electronics 406, light pipes 408, light source 410 and/or other electronics 412 may be held between outer foam 414 and inner foam 416. In an embodiment, the electronic 406, light pipes 408, light source 410 and/or other electronics 412 are on one single rigid Printed Circuit Board (PCB) and held in a single rigid plastic enclosure housing 420.

Figure 4E:
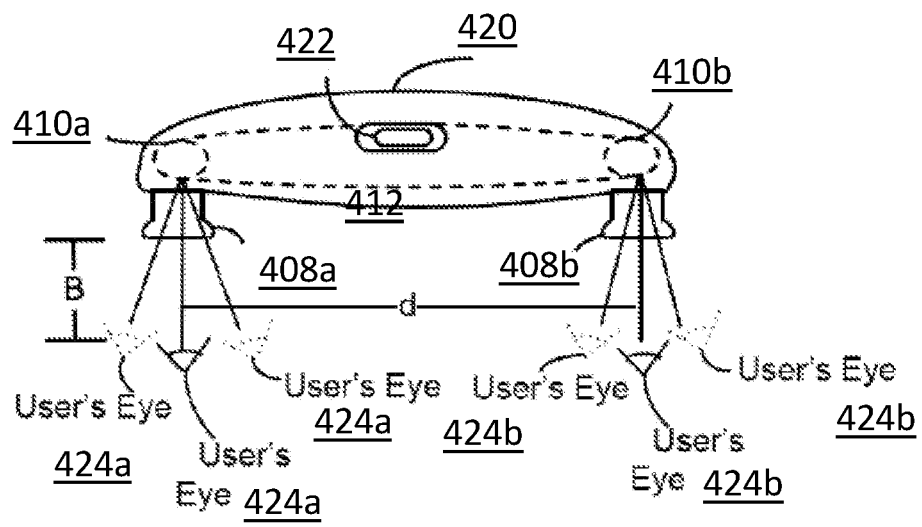
FIG. 4E shows a top view of the embodiment of the electronic insert of FIG. 4D.
Figure 4F:
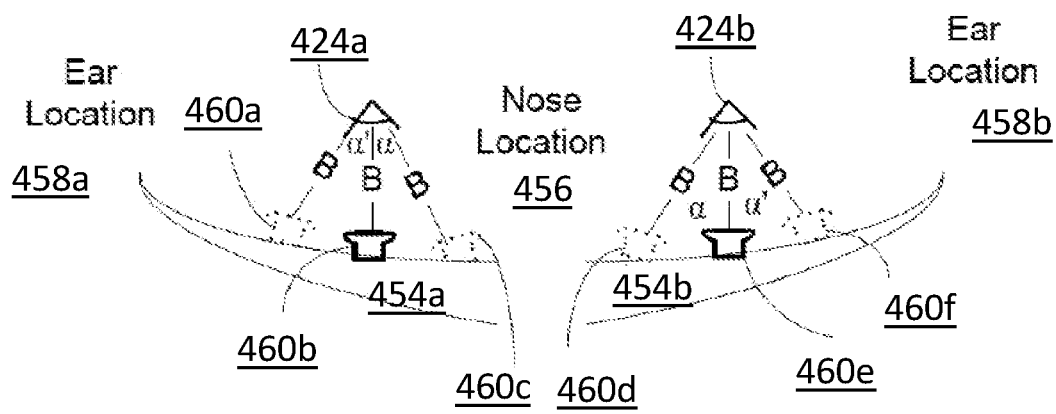
FIG. 4F shows the angle and dimension design of the electronic insert of FIG. 4D.

FIG. 4E shows a top view of housing 420, within in which electronics 406, light sources 410, and/or electronics 412 are enclosed. Housing 420 may be made from a hard resilient plastic and/or may include (e.g., made from) softer materials. Charging port 422 may be used for charging the battery that powers electronics 406 and/or electronics 412. Electronics 412 (e.g. a PCBA) and light sources 410a and b are shown in dashed lines, because electronics 412 and light sources 410a and b are hidden from view. FIG. 4F shows that the two light pipes are spaced apart by a distance d, and an angle α or α' is made between a line connecting the center of the light pipes and the center of the user's eyes, and line perpendicular to the line connecting the two light pipes, representing the angle between the center of the light pipe and the center of the user's eye pointing from the pupil. FIG. 4F shows different possible locations of the light pipes 408a and 408b. Mask portions 454a and 454b are portions of mask 400. For clarity, the rest of the mask 400 is not shown. As a reference for the direction of the angles nose location 456 and ear locations 458a and 458b are labeled. Light pipes 460a-c show possible locations for light pipe 408a for different embodiments mask 400. Similarly, light pipes 460d-f show possible locations for light pipe 408b for different embodiments mask 400. Although light pipes 460b and 460e are drawn in solid lines and light pipes 460a, 460c, 460d, and 460f are drawn in dotted lines, each of light pipes 460b and 460e and light pipes 460a-460f represent possible positions of light pipes 408a and 408b. Although there may be more than two light pipes, since only two are needed (one for the left eye and one for the right eye), only two were drawn in solid lines. In FIGS. 4E and 4F, B is the distance between the surface of the eye and the light pipe, the angle α is the angle of a diagonal line may between the user's eye 424a or 424b and the light pipe 460c and 460d when the light pipe is between the eye 424a or 424b and the nose location 454, respectively. The angle α' is the angle of a diagonal line may between the user's eye 424a or 424b and the light pipe 460a and 460f when the light pipe is between the eye 424a or 424b and the ear locations 458a and 458b, respectively.

The light pipes direct the lights from the light source to the user's eyes. In one embodiment, the light pipes are connected directly on the PCB over the location of the light sources (e.g. LED) (FIG. 4D-F). The light pipes, and light sources, are separated by a distance d of 30-150 mm apart from each other, and located within a distance B of 5-25 mm away from the surface of the user's eyes. The direction of the light pipes points at an angle α=0-72 degrees from the direction that is perpendicular to the pupil opening of the user's eyes if the light pipes are located closer to the nose than the ears, or at an angle α'=0-86 degrees from the direction that is perpendicular to the pupil opening of the user's eyes if the light pipes are located closer to the ears than the nose (FIG. 4E and FIG. 4F). In one embodiment, α and α' are both 0 degree. In one embodiment, the light pipes may include a diffuser, a scattering material, and/or a diverging lens to spread the light more evenly across the user's eyes. In one embodiment, the light pipes may be clear. In one embodiment, there may be multiple the light pipes within one cupped eye socket, with at least one pointing directly to the pupil of the user's eyes within the angle α and a' and distance B and d described above. In one embodiment, there may be reflective materials inside the eye sockets to redirect the lights coming out of the light pipe into the user's eyes. In an embodiment, the light pipes may be flexible or adjustable to adapt to different facial structures such as pupillary distance.

Figure 5A:
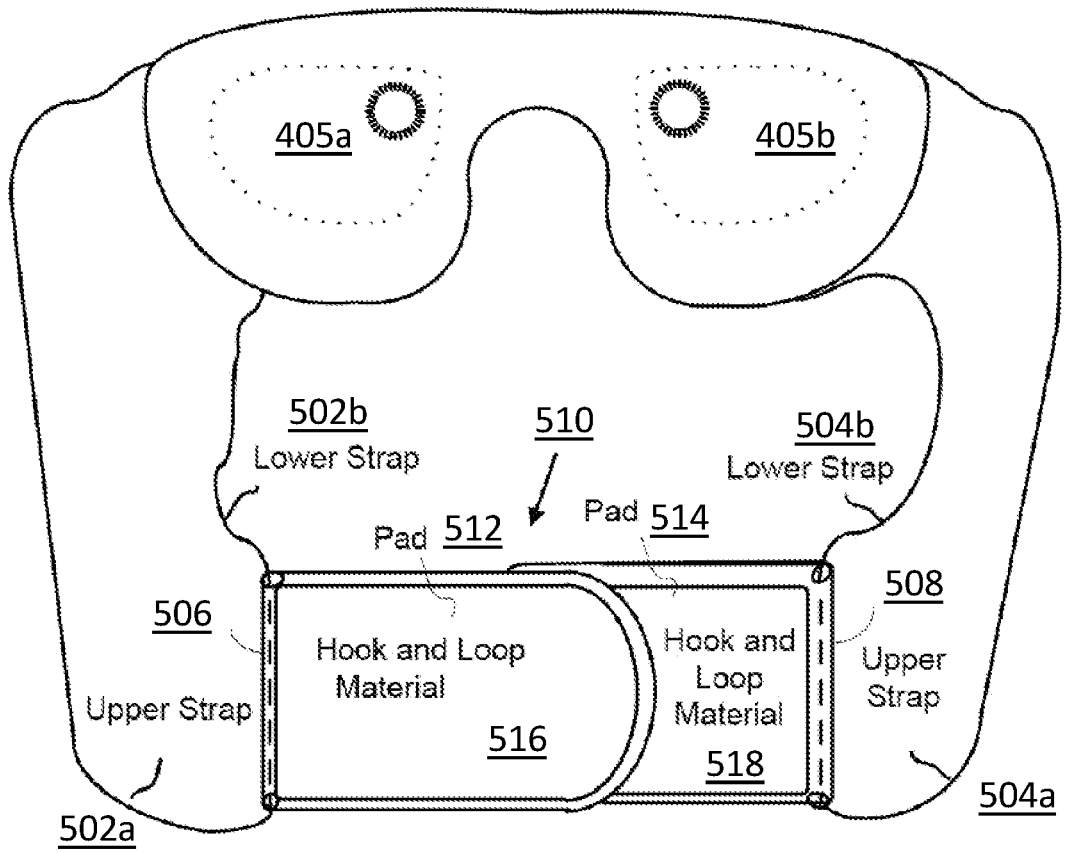
FIG. 5A shows a diagram of an embodiment of a mask illustrating the strap.

FIG. 5A shows a diagram of an embodiment of a mask illustrating the strap. The strap may be comprised of one strap at each side (e.g., strap 502 having upper strap 502a and lower strap 502b and strap 504 having upper strap 504a and lower strap 504b). The straps 502 and 504 each goes through a tunnel (e.g., tunnels 506 and 508) or slot, forming a double-strap structure that allows the adjustment of the length of the upper segment (upper straps 502a and/or 504a) and lower segment (lower straps 502b and/or 504b). The strap from each side of the mask forms a loop that goes through the tunnel 506 or 508 one pad. One part of the loop (the upper strap 502a and 504a) spans above the user's ear, and another part (the lower strap 502b and 504b) spans under the user's ear, with the third part going through the tunnel the pad (506 or 508). The double strap design enables the mask to be worn with the two straps across the upper and lower rim of the ears, individually, to keep the mask in place on the user's head without stretching on the back of the ears. The tunnel/loop structure (e.g., tunnels 506 and 508) and the relative movement of the strap through the tunnel/loop allows the adjustment of the upper and lower segment of the strap, so the mask can be adjusted according to different ear sizes, head sizes, and positions.

Figure 5B:
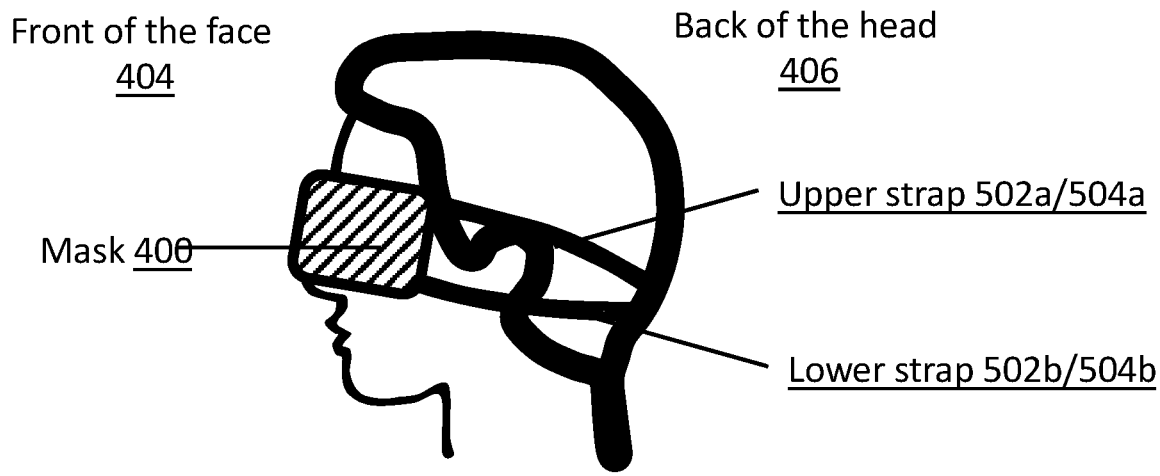
FIG. 5B shows an illustration of how a user would an embodiment of the mask.

FIG. 5A also shows a diagram of an embodiment of a mask illustrating the adjustable strap. For example, the fastener 510 having pads 512 and 514, which may be made from hook and loop material 516 and/or 518, such as Velcro®. In an embodiment, hook and loop material 516 is on both sides of pad 512 and hook and loop material 518 is on both sides of pad 514. In an embodiment, hook and loop material 516 is on at least one side of pad 512 and/or hook and loop material 518 is on at least side of pad 514. The hook and loop material piece enables the adjustment of the circumference, so the mask 400 can be adjusted to different head sizes. In other embodiments other straps, pads, and/or fasteners may be used. FIG. 5B shows a diagram of am embodiment of a mask illustrating how the straps would be worn by a user. The front of the face 402 and the back of the head 406 are shown. The mask 400 covers the region around the user's eyes. Upper strap 502a/504a spans over the top of the ear while the lower strap 502b/504b spans around the bottom of the ear.

Figure 6:
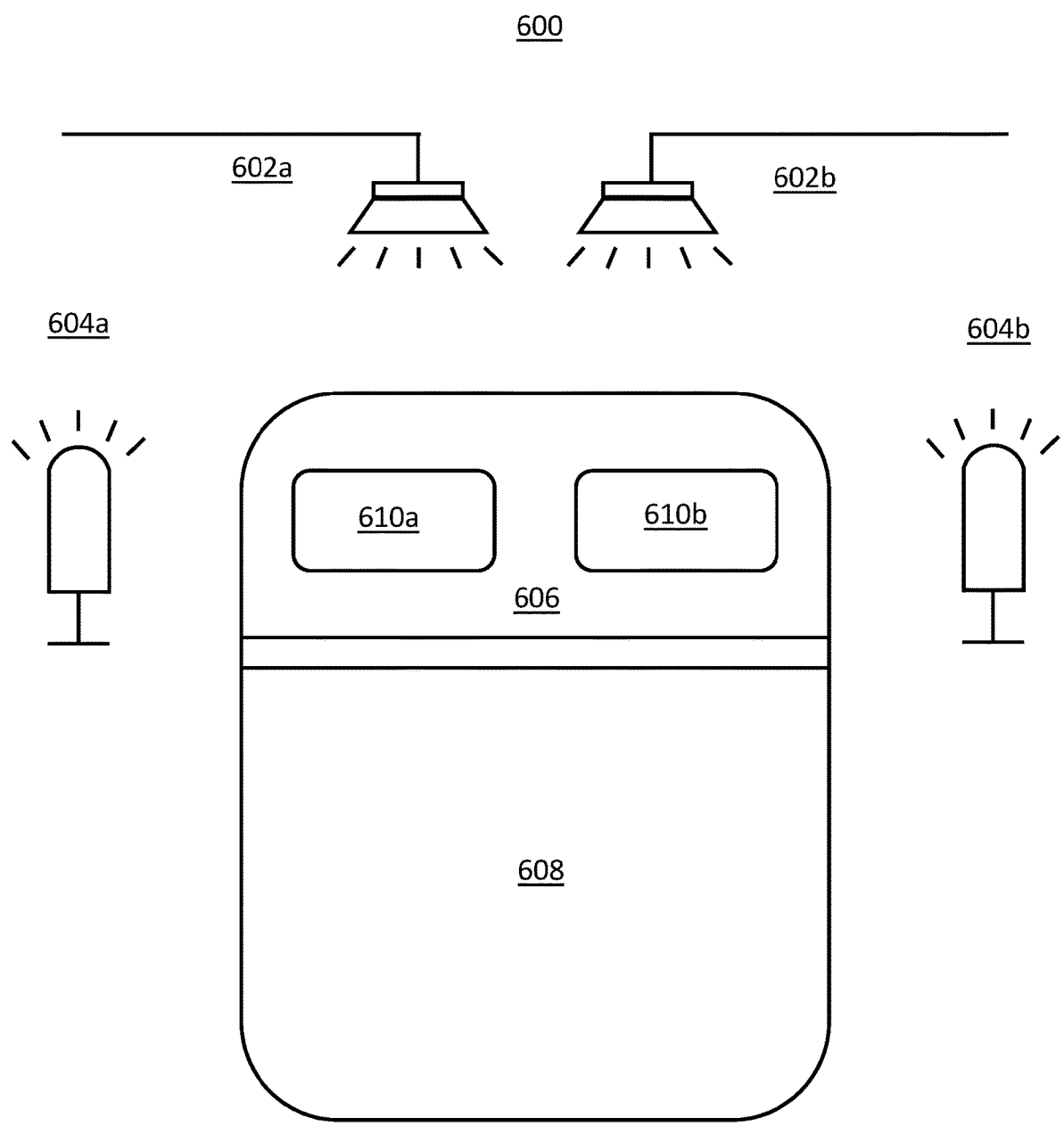
FIG. 6 shows an embodiment in which the circadian rhythm treatment hardware is built into a lighting system of the room of a building, for example.

In addition to a sleep mask, the light programs can be delivered in glasses or goggles. Another embodiment of the circadian rhythm treatment apparatus may include in-room lighting (controlled by a controller) that works with a mobile application that generates light programs based on circadian modeling algorithms to treat or prevent circadian rhythm disorders. FIG. 6 shows an embodiment circadian rhythm treatment hardware that is built into a lighting system of the room of a building (e.g., a bedroom). Ceiling lights 602a and b are light that are attached to, or that hang from, the ceiling and/or wall. Ceiling lights 602a and b may be used to deliver a circadian rhythm treatment (and to illuminate the room). Although two ceiling lights are shown FIG. 6, there may be one ceiling light—any number of ceiling lights may be used. Table lamps 604a and b are lights that may rest on the furniture or floor, and may be used to deliver a circadian rhythm treatment (and to illuminate the room). Furniture 606 (e.g. a bed) and blanket 608 and/or pillows 610a and b may be used by the user while receiving the circadian rhythm treatment. In an embodiment, the user may receive the circadian rhythm treatment (e.g. light flashes) while sleeping or relaxing on bed 606 (or in a chair), via ceiling lamp 602a, ceiling lamp 602b, table lamp 604a, table lamp 604b and/or other lamps or lights. In an embodiment, the user may receive circadian rhythm treatment while awake and performing other activities within 1-2 hours before or after sleep, or in the middle of sleep in case the user wakes up, via ceiling lamp 602a, ceiling lamp 602b, table lamp 604a, table lamp 604b, and/or other lights, in addition to and/or instead of receiving the treatment while sleeping or relaxing. Another embodiment of the circadian rhythm treatment apparatus may be built into, part of, and/or include a lamp or a set of lamps (controlled by a controller), that works with a mobile application and uses a personalized circadian rhythm disorder treatment program (e.g., light pulse program) to treat or prevent circadian rhythm disorders. Motion sensors may be embedded in 602, 604, 606, 608, and/or 610 to collect sleep data. Environmental sensors, such as light sensors may be embedded in 602, 604, 606, 608, and/or 610 to capture data input required for the mathematical models to compute circadian rhythm and general light treatment programs. The circadian rhythm treatment program may also work through accessing the API of a program and/or hardware device (an example of such a hardware device is discussed below in conjunction with FIG. 5) that controls the collection of Internet of Things (IoT) devices including the ceiling lamp 602a, ceiling lamp 602b, table lamp 604a, table lamp 604b and/or other lamps or lights.

The circadian rhythm treatment system may also deliver treatment via a computer display, television display, game console display, or mobile device display, which may be used for illuminating a confined area while the user is sleeping in involved in another activity (not related to the computer display, television display, game console display, or mobile device display. In an embodiment, the pulses of light used for circadian rhythm treatment system are too bright to be comfortable if applied while directly watching screen providing the light. However, the user is free to use the circadian rhythm treatment while the person is working on the computer or using the mobile device, watching television, and/or playing a video game, anyways, should the use choose to do so. The circadian rhythm treatment program may run on a mobile device (e.g., a cell phone or laptop) that is left on while the user is sleeping or engaged in other activities (but no looking directly at the screen). The circadian rhythm treatment system may be built into any lighting system, such as in any part of a home, television, vehicle, and/or outdoor area, in which the circadian rhythm treatment hardware is built into a lighting system of the room of a building (e.g., a bedroom). The circadian rhythm treatment system may be built into any lighting system, such as in any part of a home, television, vehicle, and/or outdoor area.

Hardware

Figure 7:
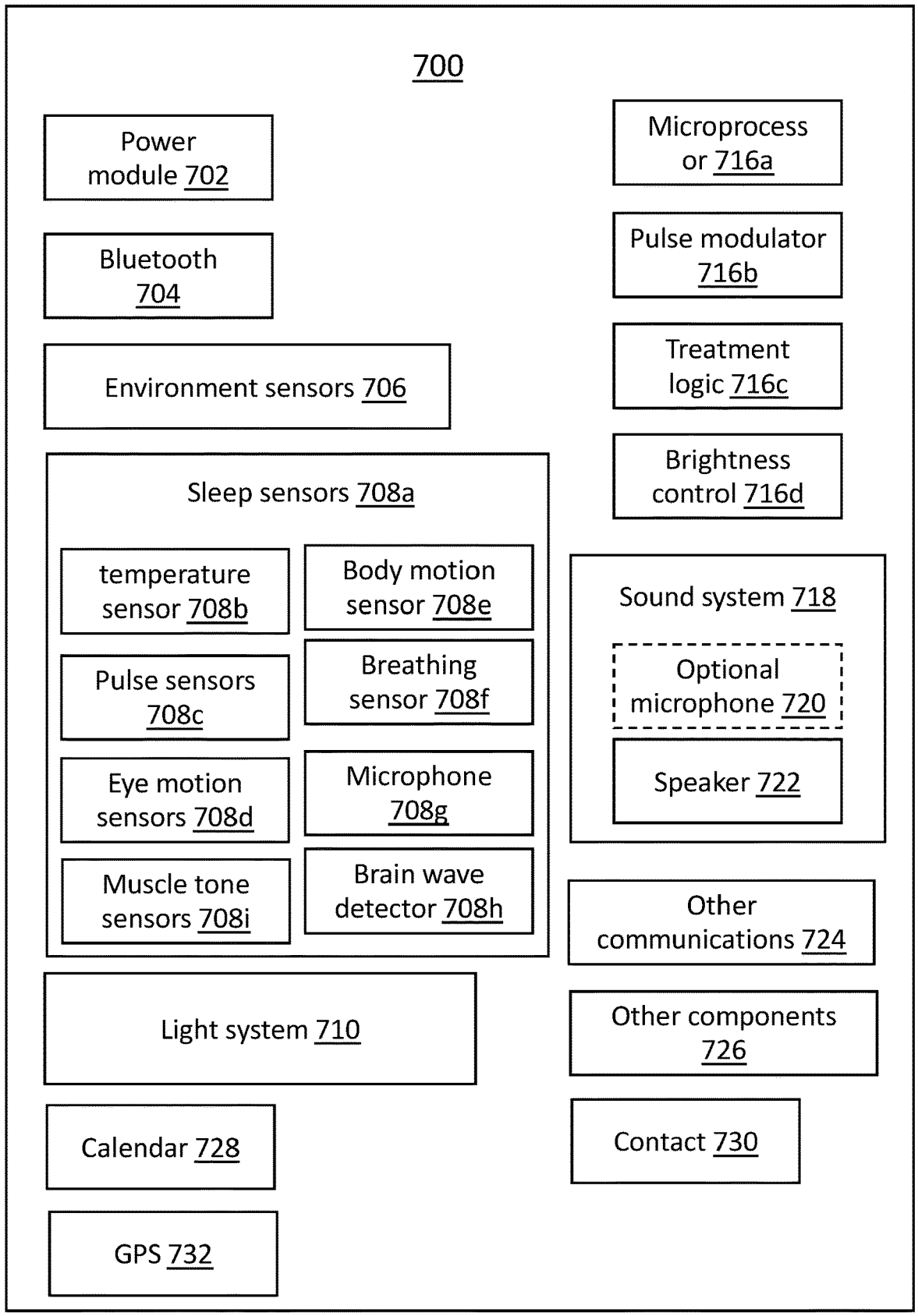
FIG. 7 shows a block diagram of an embodiment of the circadian rhythm therapy system.

The system may obtain data about the user through sensors in the circadian rhythm treatment apparatus or in the mobile phone or through an APIs of other software applications or wearables. FIG. 7 shows a block diagram of the system, which may include various hardware or software devices as possible sources from where the system can obtain data. System 700a may include power 702, near field communications 704, environment sensors 706, sleep sensors 708a. System 700 may include light system 710. System 700 includes microprocessor 716a, pulse modulator 716b, treatment logic 716c, brightness control 716d, sound system 718, which includes an optional microphone 720 and speaker 722, other communications 724, and/or other components 726. The sleep sensors 708a may include brain wave detector 708h such as dry-electrode Electroencephalography (EEG) sensors, body motion sensors 708e such as 3-6 axis accelerometers and a gyroscope, a light and body motion sensor combination such as an activity-monitoring actigraphy, a heart rate sensor 708c, and/or a respiration sensor 708f. There may also be sensors for eye movements 708d, muscle tones 708i, and/or body temperature 708b. The system may also obtain data through API of other software applications such as calendar 728 and GPS 732, or software that contains data collected by other wearable devices. The data may be used to establish, modify, or choose the most applicable algorithm to use, and/or as input for the algorithm to generate the circadian shifting program, and/or as feedback to evaluate the effect of the program and make necessary adjustments to the program. The environmental sensors may include temperature sensors, light sensor, sound sensor, and/or humidity sensors. Environment light sensor collects ambient light information, which is important for modeling circadian rhythms. The details will be discussed below. The sleep sensors may be used to determine the sleep/wake and/or the sleep stages and quality of the user's sleep, which may be used in the circadian rhythm adjustment algorithm, for example, to estimate the homeostatic sleep drive. The sleep/wake and sleep stage information may also be used in the circadian rhythm adjustment algorithm to determine the timing and/or intensity of the light emission. Additionally, information of light programs and sleep stages may also be used to correlate with the outcome of circadian rhythm adjustment, to understand whether the effect of circadian rhythm adjustment changes as lights bring given at different sleep stages.

Figure 8:
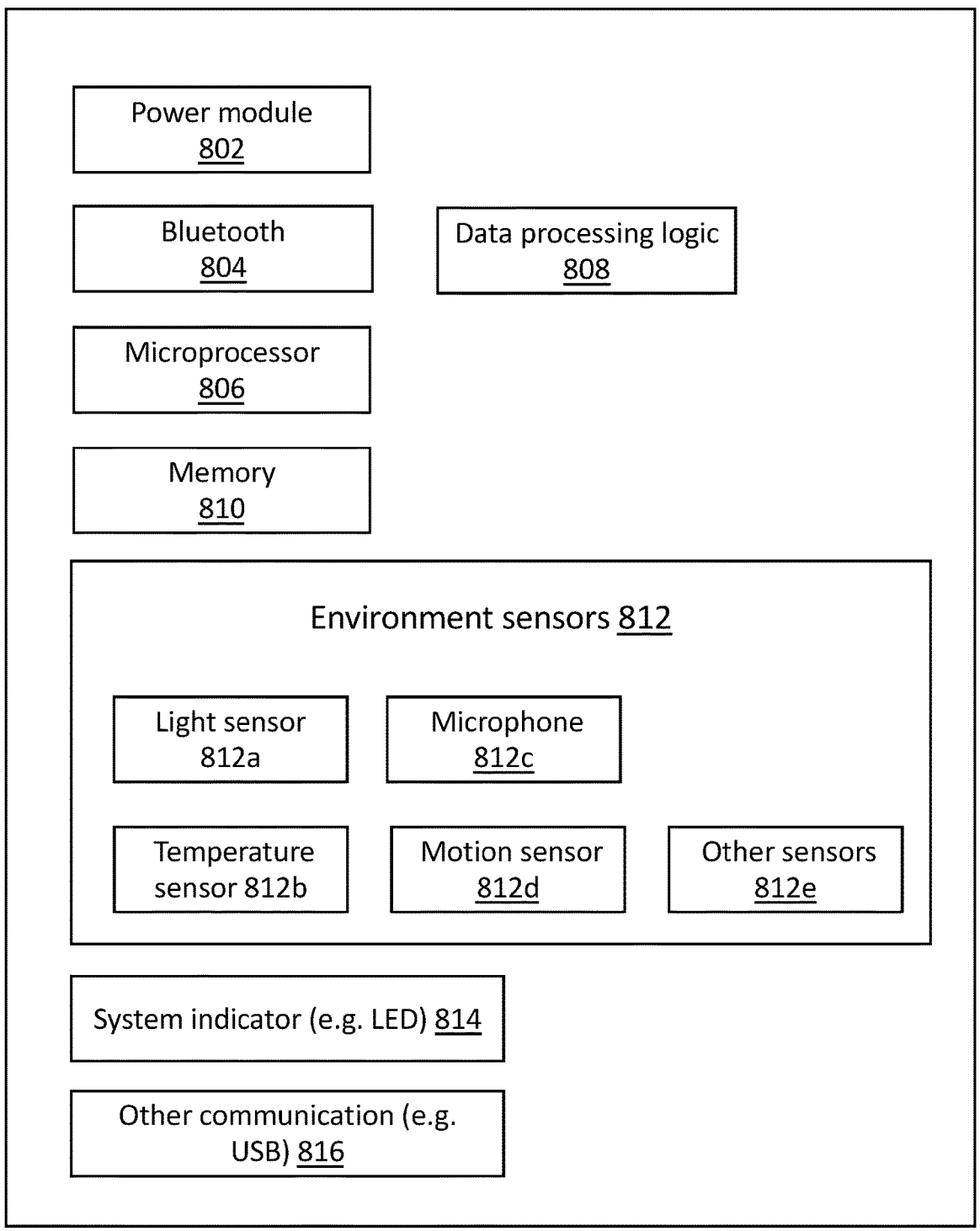
FIG. 8 shows a block diagram of an embodiment of the environmental sensing system

Alternative or in additional to user input of profiles and schedules, ambient light information can be used directly as circadian rhythm mathematical model input. In FIG. 7, one of the environment sensors 706 can be an ambient light sensor that collects light data as input for the circadian rhythm adjustment system. In one embodiment, the ambient light sensor is a sensing device separate from the circadian rhythm treatment device. In one embodiment, the sensing device may be wearable. In one embodiment, the sensing device may be a wearable light sensor in the form factor of a pin, a button, a brooch, a necklace, a chocker, or an earring, or some form factor that can be worn around the neck/chest area. The light-capturing part of the hardware generally faces the same direction as the user's face, to maximally mimic the amount of light received in the user's eyes. The wearable light sensor records the amount of light that the user's eyes are exposed to throughout the day. FIG. 8 shows a block diagram of the light sensor as possible sources from where the system can obtain data. The light sensor has multiple components: the electronic components including a printed circuit board assembly, an enclosure to house the electronic components, and mechanisms that enables the sensor to be worn on the user. System 800 may include power 802, near field communications 804 such as Bluetooth for data transmission, microprocessor 806 with data-processing logic 808, and memory 810 to store the raw data and post-process data. System 800 include environment sensors such as light sensor 812*a*, motion sensors 812*d*, temperature sensor 812*b*, microphone 812*c*, and other sensors 812*e*. System 800 may also include system status indicator 814 and other communication such as USB 816.

Model Input

A circadian rhythm adjusting system may begin by obtaining information relating to the user's circadian rhythm (e.g., information relating to times of sleep and/or wakefulness). The device may work with the mobile application with a user interface to take input and generate personalized circadian rhythm disorder treatment programs to treat or prevent circadian rhythm misalignment. The input variables of the model may be collected, via user input from a mobile application interface, information collected by sensors in the hardware, and/or via APIs of other software or hardware such as a wearable tracker, a central software data source such as Apple Health, a calendar system or a work scheduling system. The inputs for the model may include any one of, or any combination of, age, sex, eye colors, pupillometry, light sensitivity, usual bed time, usual wake time, current bed time, current wake time, usual sleep time, desired shift/sleep schedules, including desired bed time, desired wake time, desired sleep time, travel schedules, night shift schedules, and/or schedule constraints. In one embodiment, user input may also include nap times, day-time activities, food intake, exercise, caffeine intake, other potential factors influencing, and/or indicative of, wake and sleep. In an embodiment, the user can input multiple schedules at one time. The program then may automatically detect and automatically generate a program to accommodate all the schedules to implement at a given time based on calendar information input into a calendar and/or GPS information.

Figure 9:
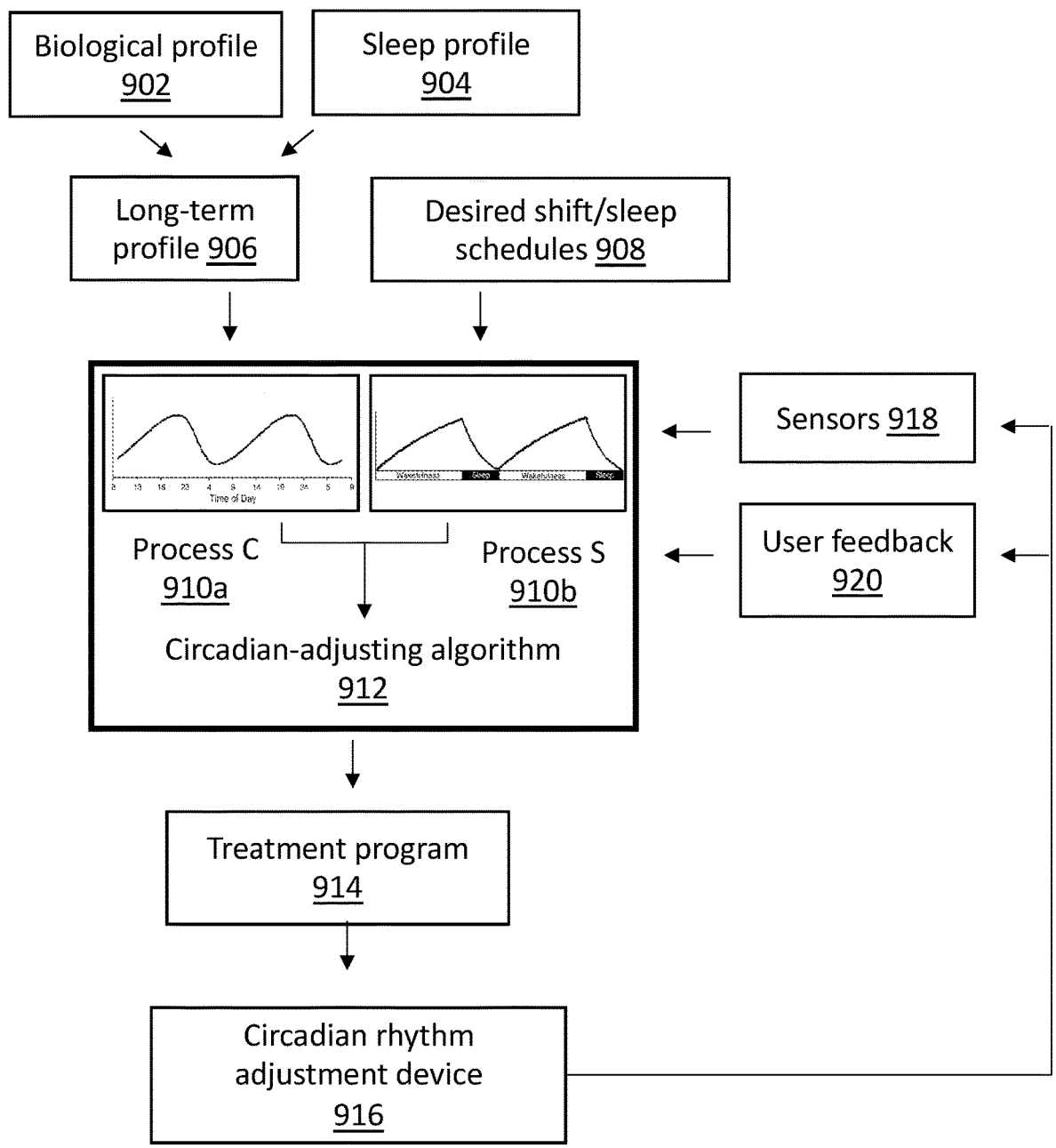
FIG. 9 shows a flowchart for a method in which the system of FIGS. 3A and 3B may operate.

FIG. 9 shows an exemplary process by which a circadian rhythm adjusting system may operate. As shown in FIG. 9, the system takes input and creates a biological profile for the user in step 902, and creates the user's sleep profile in step 904. Both the biological profile and the user's sleep profile are stored as part of the user's long-term profile in step 906. The biological profile may include the user's age, sex, eye color, pupillometry, weight, height, amount of exercise, light sensitivity, etc. Information about the user's sleep profile may include the user's typical bedtime and wake time, the typical sleep efficiency, the number of hours the user ordinarily sleeps, the number of times the user gets up in the night, whether the user has a form of insomnia, sleep apnea, or other sleep disorder. The sleep profile may also include the chronotype of family members. Alternative or additionally, in one embodiment, the system may connect to the API of other third-party hardware to retrieve long-term sleep data. In one embodiment, the long-term profile also includes genetic information obtained from laboratory assays on sample collected from the user and/or third-party sources containing genetic testing information about the user, for example, personal genomics companies such as 23andMe. In one embodiment, the long-term profile may also include natural circadian rhythm baseline established by bio-samples collected from the user or from wearables with sensors such as actigraphy. In step 908, the application then receives input (e.g., entered by the user) that indicates the user's current and target/desired sleep schedules, travel information, work shift information, sleep constraints (e.g. from work and social activities) and/or other information to understand the circadian phase shift needs. For example, the system may adjust the circadian rhythm based on the user's current sleep schedules as compared to the desired sleep schedules, or based on the user's desired work and/or travel schedules, where the user may input information indicating the change in the sleep pattern desired, via a graphical user interface.

In at least one embodiment, the inputs for the model may include sleep data specifically about the user, collected, or via sensors in the wearable devices and/or other device, via an APIs of software applications and/or via a user interface of an application and/or through hardware in a sleep mask or devices from which the light flashes are delivered. In this specification, "sleep data" may refer to data relating to sleep or which is probative of sleep and can be used, alone or with other data, to assess a user's sleep. For example, sleep data may include data relating to one or more of sleep schedules, wakefulness schedules, work schedules, flight schedules, feasible sleep windows, sleep constraints, circadian rhythms, sleep environment, light exposure, sleep disruptions, sleep quality, alertness level, physiological parameters relating to sleep, including movements, respiration, heart rate, brainwave, eye movement, muscle tones, and so on. One example of sleep data is ambient light data from a wearable light sensor in the form factor of a pin, a button, a brooch, a necklace, or an earring, or some form factor that can be worn around the neck/chest area facing generally the same direction as the user's face to mimic the amount of light received in the user's eyes throughout the day. The user will wear the light sensor as much as possible, except when showering and sleeping. When the user is sleeping, the light sensor may still be put facing upward next to the user's head to record the environmental light intensity in the bedroom during the time when the user is sleeping.

In at least one embodiment, an adjusted sleep treatment program is implemented. The system may generate an initial program based on the initial input. As the sleep program is running and new information is received, the treatment program is adjusted based on information received. The input may include data collected from sensors, for example, the ambient light exposure data or the sleep data, and user's feedback after using the device, for example, if/when they use the device on previous day(s). Based on new information, an updated program may be generated to fit the most current circadian clock of the user. The circadian rhythm treatment system can be used before, during, and/or after the occurrence of the change of sleep schedules or time zones or anytime when the user would like to improve sleep through optimizing circadian rhythms and alertness. Different programs may be established, presented, or started when the user starts the program depending on the time when the user open the circadian rhythm application. The adjustment to the treatment program may occur in the middle of a treatment program and/or may be applied to a future treatment.

In at least one embodiment, the inputs for the model may include data collected from look-alike demographics in laboratory studies, or studies conducted by other organizations. For example, benchmark biological markers may include any one of, or any combination of pupillometry, iris color, salivary melatonin, core body temperature, plasma cortisol, plasma melatonin, and urinary melatonin that can be collected in appropriately controlled inpatient environment and used to estimate properties of the central circadian pacemaker. In one embodiment, the salivary Dim Light Melatonin Onset (DLMO) data may be obtained in lab studies upon light treatment. In one embodiment, salivary or urinary melatonin may be collected and analyzed in the lab or by an analysis kit operated by the user. In one embodiment, ambient light exposure data, sleep diaries, and other self-reported survey data may be obtained in lab studies. These data obtained for certain population and/or certain light treatment programs may be used as input variables to model Process C. Similarly, benchmark polysomnography (PSG), EEG, EMG, movements, and other biological markers can be collected and fed into the mathematical mode to estimate sleep/wake and the Process S and/or calculate the light treatment program. For example, movement data may be used to estimate how long the user has been awake for, which may then be used to calculate Process S. During the night, the body goes through several sleep cycles (e.g. of 90 minutes to 120 minutes) with different stages. Each of the stages of sleep has a different brainwave frequency and amplitude: waking state/REM sleep: high-frequency (15-60 Hz), low-amplitude activity (~30 µV); N1: decreased frequency (4-8 Hz), increasing amplitude (50-100 µV); N2: (10-15 Hz, 50-150 µV) spindles; N3: 0.5-4 Hz (100-200 µV). EEG sensors on the head (which may be included in the mask or other elsewhere) can be used to detect the distinct brainwave signature in amplitude and frequency during different stages of sleep. The EEG may detect brainwaves during sleep, through which the system may be analyzed, to determine sleep/wake and/or stages of the sleep of the user. Other physiological markers such as reduced body movement and eye movement, slowed down heart rate and breathing, decreased body temperature, decreased blood pressure may also be used to determine sleep/wake and/or stages of the sleep of the user. During nocturnal awakenings (e.g. a result of the flashes of light being too bright), body movement increases, accompanied by a different eye movement pattern from that in N1-N3 sleep or REM sleep. The system may then adjust the circadian clock adjustment program based on the real-time input. For example, the light flash program may be paused or reduced temporarily if nocturnal awakenings were detected. Similar parameter changes can be captured by sensors in the system, used independently or in combination, to help inform and adjust the light program.

In one embodiment, genetics information correlated with circadian rhythms, chronotypes, sleep conditions or disorders may be used as part of the model, or be used to define or refine parameters of the model. As part of the circadian rhythm adjustment system, there may be sample collection devices to collect the saliva, urine, blood, or other biosamples from the user as part of profile establishment or as part of each treatment. The samples may be sent to the lab for analysis, the results of which may be used in the model to estimate Process C and/or Process S, or other factors that may affect the circadian rhythm treatment program. For example, genetic variants of PER1, PER2, PER3, or CLOCK may be used to inform the user's natural circadian tendency. Additionally, genetic variants of COMT, ADA, ADORA2A, DEC2, or ABCC9 may be used to inform the user's natural tendency on daytime sleepiness, brain wave patterns, usual sleep duration and estimate their homeostatic sleep drive. Related, but separately, in one embodiment, biomarkers such as melatonin may be collected from the saliva, urine, blood, or other samples of the user to establish a baseline for circadian rhythm. The biomarkers may be used for users who potentially have a natural circadian clock substantially different from 24 hours. For example, by sampling and measuring salivary melatonin continuously over a period of time, the system may determine the natural circadian rhythm of the user. If the user has a circadian cycle that is 28 hours instead of the typical 24 hours, the period T used in the model will be replaced by the actual period obtained from melatonin monitoring rather than a pre-assumed value of 24 hours from the general population or lab-generated data on look-alike demographic. As a similar example, if mutation in CRY1 which is associated with delayed sleep phase disorder is detected by genetic testing, then the model may assume that the user has a naturally delayed circadian phase and use the information to adjust the circadian rhythm estimation model.

Model

The regulation of the sleep-wake cycle is determined by many factors, including genetics, circadian rhythms, homeostatic sleep drive, sleep environment, conscious decisions and behaviors, and so on. The factors that determine the regulation of sleep may play a part in the circadian rhythm misalignment cases described above. Therefore, in at least one embodiment of the circadian rhythm adjustment system, to account for the circadian rhythm misalignment scenarios such as night shifts, instead of the circadian rhythm adjustment algorithm only considering circadian rhythm misalignment based only on the estimation of the PRC based on current and target sleep schedules, a model that includes multiple factors that regulate sleep and wake cycles, such as the circadian rhythm (Process C) and the homeostatic sleep drive (Process S), and based on the combination of multiple factors (e.g. sleep schedule constraints and conscious choices), the windows of time during which to apply a light treatment in order to shift the circadian rhythm are determined. As shown in the flow diagram in FIG. 9, after taking model inputs, a circadian rhythm adjusting algorithm 912 may compute both Process C in step 910*a* and Process S in step 910*b* and their interactions in regulating sleep/wake cycles to form a circadian rhythm adjusting program. The output of circadian rhythm adjusting algorithm 912 may then be incorporated into a light therapy algorithm to generate the treatment program in step 914 for the specific user and the specific schedules. The treatment program may then be sent to the circadian rhythm adjustment device in step 916 to deliver the light program. The model may be calibrated anytime during the process using additional information such as data collected from sensors in step 918 and/or user feedback in step 920.

Figure 10:
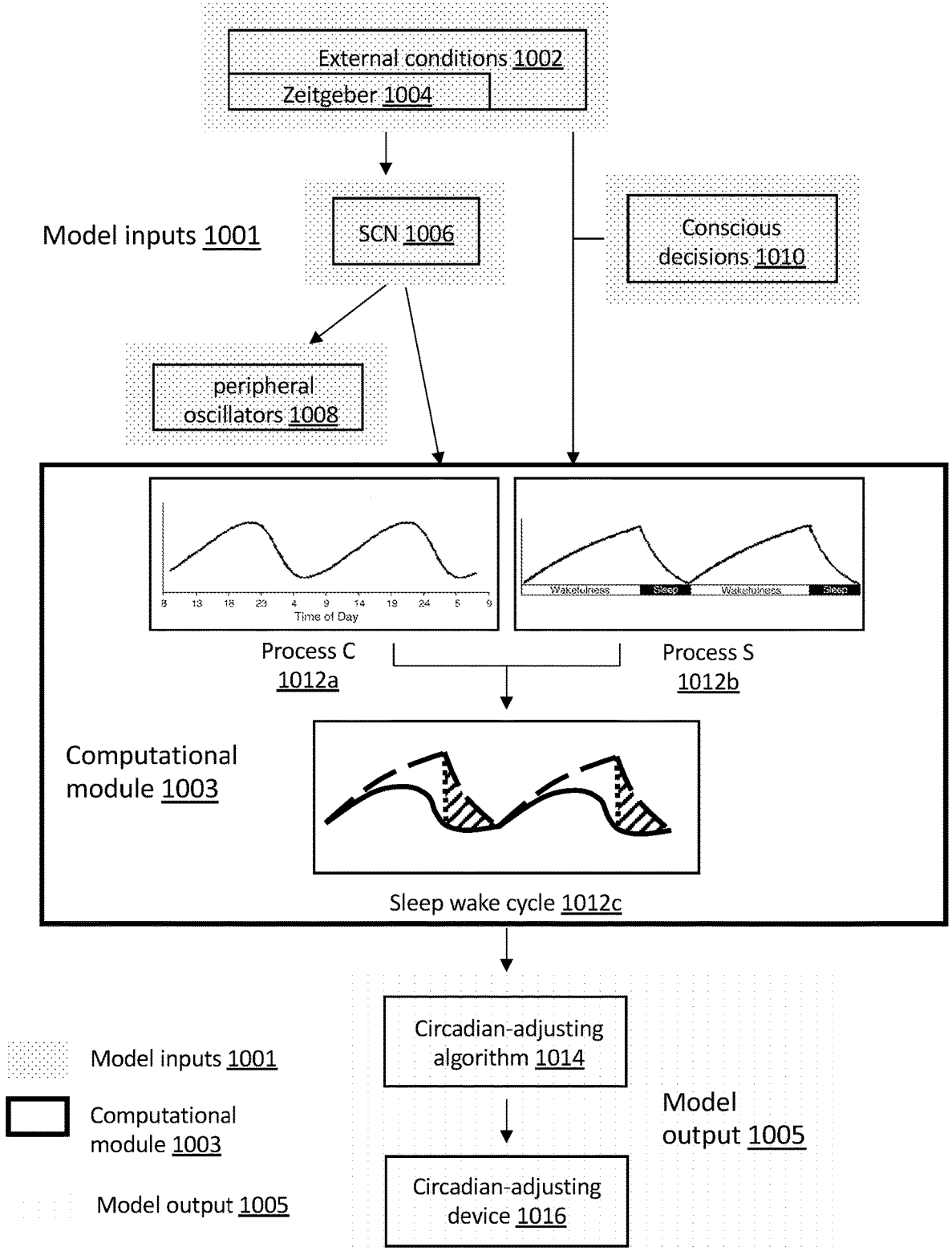
FIG. 10 shows a flowchart for how the circadian rhythm adjustment algorithm and treatment program are generated.

FIG. 10 shows a block diagram of a circadian rhythm adjusting system with model input, computation, and model output, in which the computation module calculates sleep wake cycle via analyzing Process C and Process S. Model input 1001 may include external conditions 1002, Zeitgeber 1004, markers for peripheral oscillators 1008, and schedules determined by conscious decisions 1010. Zeitgeber 1004 refers to physical and social events which entrain the circadian clock, for example, light from the environment. The suprachiasmatic nucleus (SCN) 1006 is the central circadian pacemaker in the brain. SCN regulates a number of markers for the circadian clock, including peripheral oscillators, such as melatonin and core body temperature. In one embodiment, signals from SCN are included as model input. The computation module or the modeling module 1003 include computation of Process C 1012*a* for the circadian rhythm (C) and Process S 1012*b* for the homeostatic sleep drive (S). The homeostatic sleep drive is a function of how long a person has been awake. It builds up during wakefulness and declines monotonically during sleep. Together, Process C and Process S regulate sleep. As shown in the sleep wake cycle 1012*c*, sleep switches on when the distance between S and C reaches maximum and switches off when the distance reaches minimum. The model may estimate sleep and wakefulness 1012*c* by calculating both Process C 1012*a* and Process S 1012*b*, and generate a predicted PRC and the optimal way to shift circadian phases. Based on the model output, a circadian rhythm therapy programs (e.g., treatment regimen) 1014 may be generated to shift circadian phases. The light program generated from the algorithm will then be sent to the circadian rhythm adjustment device 1016. In at least one embodiment, the main outputs for the model may be suggested timings for light therapy based on the PRC. Programs generated by the system to delay circadian phases happens during hour 15 to hour 24 (CT15-CT24), advance during hour 24 to hour 8 (CT24-CT8) of the subject's effective circadian time, in which CTO is defined as the cross-over point of the human phase-response curve. The cross-over point may be defined as the time of the fitted minimum of unmasked core body temperature. The system may predict the time that corresponds to CTO based on the information described before (the inputs to the C and/or S models), such as the user's biological profile, sleep schedules, travel or shift schedules, physiological data obtained from sensors, and/or other information obtained in lab studies. In one embodiment, the system may suggest specific light stimulation timing to delay or advance circadian clocks, together with other light flash parameters. The light timing will be incorporated into the circadian adjusting algorithm 1014.

The computational module may be designed to optimize for at least one of two outcomes, or both if possible: (1) maximizing circadian shifts to achieve the largest overlap between the "sleep" phase of the circadian clock with desired sleep time, and the largest overlap between the "awake" phase of the circadian clock with desired windows of wakefulness; and (2) instead of maximizing the amount of circadian phase shift, calculating the circadian phase shift so the window of high alertness can be best overlapped with desired window when peak performances are required or so the window of low alertness can be best avoided from when peak performances are required. Depending on the applications, the model may use different algorithms to handle different tiers of complexity, including (but not limited to) the following scenarios: (1) When sleep schedule change is simple, the model may only consider the difference in circadian phases and maximize circadian shifts to achieve most alignment. (2) When sleep schedule (and/or geographic location) changes are predictable, regular, with good sleep consistency that lasts for long enough to allow full entrainment by light therapy, the model may consider the additive effect between circadian rhythms and homeostatic sleep drive to maximize circadian shifts, with the assumption that these two processes are independent. (3) When sleep schedules are irregular, changing, unpredictable, or significant over a short amount of time that may be accompanied with prolong wakefulness and/or naps, the model may optimize for maximal overlap of circadian phase with desired sleep-wake schedule, take into account of both circadian rhythms and homeostatic sleep drive, with the assumption that these two processes are independent. Alternatively, the model may consider the nonadditive relationship caused by the interaction between these two processes and how one process affects the other when responding to regulatory signals. (4) Instead of optimizing for the maximal circadian phase shift, the model may optimize for performance by overlapping the maximal alertness with the windows when peak performance is required. The model may consider both circadian rhythms and homeostatic sleep drive, with the assumption of circadian rhythms and homeostatic sleep drive being essentially independent. (5) In cases with prolong wakefulness and/or naps, the model may optimize for performance during the windows when peak performance is required, while taking into account the interdependency between circadian rhythms and homeostatic sleep drive. (6) In the presence of other sleep-regulating factors (e.g. genetic components) that may significantly affect circadian rhythms and homeostatic sleep drive directly or indirectly, the model may take them into consideration and give them corresponding weight in the calculation.

To model Process C, one or the combination of any of at least three modeling approaches may be used, which may include (1) modeling the physiological components of the system; (2) using mathematical models to match the dynamical properties of the system; (3) data-driven modeling or statistical fitting of the data. For example, each of these three approaches may be different aspects of the same model. The Process C can be generally be considered as (or at least approximated by) a sinusoid function or a skewed sine wave of $f(t)=a \sin(\omega t+c)$, with amplitude a, angular frequency $\omega$, period $2\pi/\omega$, and phase c (and/or another harmonic function), while t is time, Similarly, the function $f(t)=a \cos(\omega x+c)$, $f(t)=a\, e^{\mp i(\omega t+c)}$, and/or a combination of the three (for example) could be used instead (however, the value of c depends on the choice or functions). Similarly, since the above functions can be expanded in terms of any set of orthogonal functions, other periodic functions may be used, such as Bessel functions. In at least one embodiment, $f(t)$ is a sum of harmonic functions (e.g., a sum of sine and/or cosine functions and/or a Fourier series). Multiple physiological parameters display periodic level changes, which can be used to determine the phase of Process C directly. Data collected from the circadian rhythm adjustment system may also be used to determine the phase of Process C or the parameters in the equation to model Process C. For example, biological markers of the circadian clock collected in appropriately controlled inpatient environment from the user or look-alike populations may be used to model circadian rhythms. These biological markers include a combination of one or more of core body temperature, plasma cortisol, plasma melatonin, and salivary melatonin, and so on. Process C can be expressed as the oscillation of core body temperature, where the lowest point of the circadian wakefulness signal overlaps with the temperature nadir, CTO (the time of the fitted minimum of unmasked core body temperature). Once CTO is set from core body temperature measurement or calculation based on other physiological parameters such as melatonin level or other data such as sleep schedules. Based on CTO, the PRC may be calculated (FIG. 1 102), based on which the light treatment window for delaying circadian phase can then be calculated as CT15-CT24 (FIG. 1 104), whereas light treatment window for advance circadian phase can then be calculated as CT24-CT8 (FIG. 1 106). (note that at ωt+c=CTO, $f$ (t) reaches its minimum value, and so the argument ωt+c=−π/2, and thus if t is the time on the clock, c is a measure of time duration between midnight and the time at which CTO occurs). In some people with normal sleep habits and circadian rhythms, CTO may occur between about 3:00 am and 7:00 am, but may occur at other times also, depending on the individual. In at least one embodiment, value used for the period T or angular frequency ω (ω=−2π/T) is based on an average value, which may be determined by measuring ω randomized cross section of different people. In at least one embodiment, the period is set as 24 or 24.15 hours for general purpose circadian modeling, and other specific numbers may be used when modeling for specific populations (and/or individuals). For example, a given population or individual may have a circadian clock period of 28 hours instead of 24 hours. In at least one embodiment, the circadian clock period may be set based on the biological sex of the user, with 24.19 for males and 24.09 for females. In at least one embodiment, the circadian clock period and amplitude may be set to demographic baseline according to the age of the user. In at least another embodiment, the period is determined based on emprical data of certain demographics which may be slightly larger or smaller than one day 24 hours, for example, in teenagers, and it would seem that ω may vary between individuals. In an embodiment, the circadian clock baseline may be established by continues melatonin measurement from the user's saliva sample or sleep-wake cycle recording with actigraphy data. In at least one embodiment, biological markers obtained from sleep study participants in strictly controlled lab environment and/or empirical data aggregated from many individuals may first be used to establish the models. The parameters of the model may then be further calibrated by data collected outside the lab from each individual, for example, via sensors in the mask, sensors in the ambient light sensing device, or other wearable device(s). In at least one embodiment, the biological markers or the model generated based on the biological markers may first be correlated with model inputs that can be collected from a non-laboratorial environment. The model may then be applied to estimate the circadian phases of users in a non-laboratory environment, based on user inputs collected from the mobile application interface or sensors from the hardware, or via API from third party applications. Examples of empirical data collected by the system based on the user's individual experiences/ behaviors may include: bed time and wake time, core body temperature, heart rate, melatonin, cortisol, and so on. Depending on the similarity of the user with the experiment participants, adjustments on the model may be applied when estimating the circadian phase of each individual user. In at least one embodiment, as the user uses the system and more data is collected about the user, the model is adjusted to the user's individual body and situation, and after sufficient use, the model may be entirely based on the user's individual body and situation. User feedback may be collected via user input or sensors in the hardware after the treatment sessions, to further calibrate the model for each user and/or to further perfect the model for handling users for which no data has been collected yet. For data collected outside of an appropriately controlled lab environment, variability introduced by noncircadian factors such as behaviors or schedule constraints may need to be compensated for. In some embodiments, the model may be matched to the oscillations behaviors of the circadian system. Stochastic models may also be used to account for the noise and randomness of the system, depending on the purpose of modeling. In some embodiments, data-driven modeling or statistical fitting may be used to model circadian rhythms. For example, Process C can be estimated by the following equation:

$$C = A\{0.97 \sin[w(tt_0) + 0.22 \sin[2\omega(t-t_0) + 0.07 \sin[3\omega(t-t_0) + 0.03 \sin[4\omega(t-t_0) + 0.001 \sin[5\omega(t-t_0)]\}$$

$$\omega = 2\pi/\tau$$

In which: C=Process C (note capital C is different than the phase, which is represented by the lower case c), which is independent of Process S; A=amplitude of skewed sine wave; t=time; τ=period of C; $t_0$ defines the circadian phase at the beginning of the stimulation.

The constants of this sinusoidal curve can be fitted using regression analysis to the melatonin or core body temperature data collected in the lab in strictly controlled environment that share various levels of similarity with the end user of the circadian rhythm adjustment system. When using biological marker such as melatonin and core body temperature, some rhythmic properties of the circadian system, such as the period, amplitude, and phase, can be extracted via statistical models. Once the model parameters are determined, it can be used as a base model for look-alike populations which may be further calibrated with user feedback or data captured as the user uses the device. More generally, $C=\{a_1 \sin[\omega(t-t_0)] + a_2 \sin[2\omega(t-t_0)] + a_3 \sin[3\omega(t-t_0)] + a_4 \sin[4\omega(t-t_0)] + a_5 \sin[5\omega(t-t_0)]\}$, where the set of amplitudes, $\{a_1, a_2, a_3, a_4, a_5\}$, may be determine empirically, and/or first assumed to be from the literature or lab studies on look-alike subjects, and then adjusted over time to values determined based on sensor input and user input to the system about the user. In at least an embodiment, higher order terms may be added (e.g., for someone without a regular sleep time, but that is forced to have periods of napping and being wake through the day and night). In at least one embodiment, each term may have a different value for ω and/or $t_0$.

The model may also estimate Process S and the linear (e.g. additive) relationship between Process C and Process S, with the assumption that Process C and Process S are independent without interfering with each other. As shown in FIG. 10 1012b, the sleep drive builds up during wakefulness and declines monotonically during sleep. The rate of increase and decrease of S may be estimated using an exponential model. For example, with a rise factor of r and a delay factor of d, Process S may be modeled using the following equation:

Sleep: $S_t = dS_{t-1}; d = e^{-\Delta t/\tau_d}$

Wake: $S_t = 1 - r(S_{t-1}); r = e^{-\Delta t/\tau_r}$

In which, S=Process S; d=decay factor of S; r=rise factor of S; $\tau_d$ and $\tau_r$=time constants; Δt=time step (which may be 30 min or other values as modeling requires); t & t−1=time indices between time step.

The function d, $\tau_d$, and/or $\tau_r$ may be obtained through literature or empirical data from look-alike subjects in lab studies and/or data collected the end user of the circadian rhythm adjustment system. For example, in laboratorial studies, the decay rate of S may be calculated from EEG measurements on experimental subjects and used in the model for look-alike subjects outside of the lab. Alternatively, in at least one embodiment, brainwave signals may be captured from EEG sensors implemented on the circadian-adjusting hardware (for example, a sleep mask) through contacts around forehead. In at least one embodiment, the sleep pressure may be estimated using a default r value (for example, from literature or laboratory studies) and then adjusted when more data is collected from the user by sensors in the circadian-adjusting hardware or other wearables. The homeostatic sleep pressure may also be measured by the length of time staying awake that can be deferred from the sleep/work schedules or length of time that is required for one to fall asleep. The data input for this estimation may be captured by sensors, such as an EEG, accelerometer (e.g., or 3-6 axis accelerometers), a gyroscope, an activity-monitoring actigraphy, an optical pulse sensor, a respiration sensor, from third-party wearables, applications (e.g., downloadable apps), estimated by the sleep onset latency from sleep diaries, and/or other user input. As mentioned above, there may be a different accelerometer and/or gyroscope for or more of three different, non-parallel axes, where the three axes optionally maybe perpendicular to one another. Alternatively, the sleep pressure may also be inferred from measuring one's alertness, the tendency for the user to dose off unintentionally, the changes in the tendency of the user to make mistakes (e.g., the number of typographical mistakes made), or user input. Alternatively or additionally, the alertness may be determined from the number of typographical mistakes made can be measured by monitoring the user's interactions with the user's cell phone and/or computer (or other electronic device) and counting spelling errors (or other types of clerical errors) measuring speed of data entry, and/or analysis of voice input during normal usage (the speed of ones speech and speech errors may change depending on how alert one is). Alternatively or additionally, the user may be asked to copy text during the different times of the day and speed and accuracy can be measured.

Figure 11:
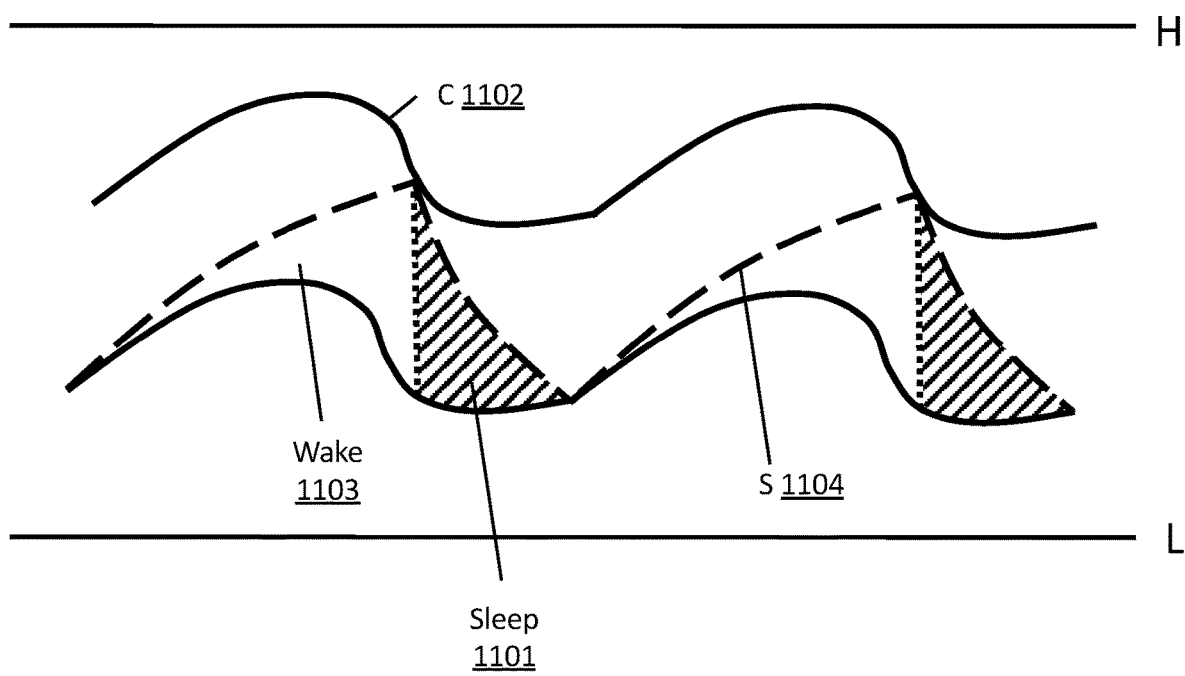
FIG. 11 shows a diagram of how elements of the algorithm interact.

When modeling the additive relationship between Process C and Process S, a model in FIG. 11 may be used. In the embodiment of FIG. 11, Process C 1102 is considered as a sin wave curve that has a higher threshold H and a lower threshold L (in other embodiments a different curve may be used for the C Process. Process S 1104 builds up during wakefulness and dissipates during sleep. Sleep 1101 switches on when S reaches the higher threshold H, and switches off when S reaches the lower threshold L. The frequency of sleep-wake alternations depends at least in part on the interval between H and L and on the rate of buildup and breakdown of S. Quantitative estimates of the C threshold variations can be derived by results from prior studies, or by measuring either the tendency to go to sleep during wakefulness, the tendency to wake up during sleep, and/or from the circadian oscillation from the S level at the time of awakening, which can be calculated directly from the duration of sleep in subjects waking up at different times of the day. The instantaneous breakdown rate of S can be calculated using an exponential model (in other embodiments other functions that increase with increases in time may be used, such as a polynomial). Sleep initiates when S>H+C, and terminates when S<L+C. The model may start with the parameters commonly used to estimate spontaneous sleep termination and onset, which may be taken as A=0.12; τ=24 h; $\overline{L}$=0.17; $\overline{H}$=0.67; Δt=0.5 h. Based on more information such as travel and/or night shift schedules, the parameters may be updated. The circadian rhythm adjustment system may also update the parameters based on other information, such as user input on their biological profiles and normal sleep schedules, or data collected on wearables in the system or through the third party, such as actigraphy and/or EEG readings. After being used for an extended period of time, the system may also refine the parameters based on user feedback or biofeedback on the sleep or the circadian rhythm as a result of each schedule change and corresponding treatment. In cases where the user takes a nap during the period of wakefulness, the homeostatic sleep drive changes, which also may be accountable for. Process S may be dissipated with naps whereas be accumulated with prolonged wakefulness. Therefore, the timing and duration of naps and/or prolong wakefulness may be part of the model input when applicable. The timing and duration of naps and/or prolong wakefulness may also be part of the model output as schedule suggestions for the user.

Figure 12:
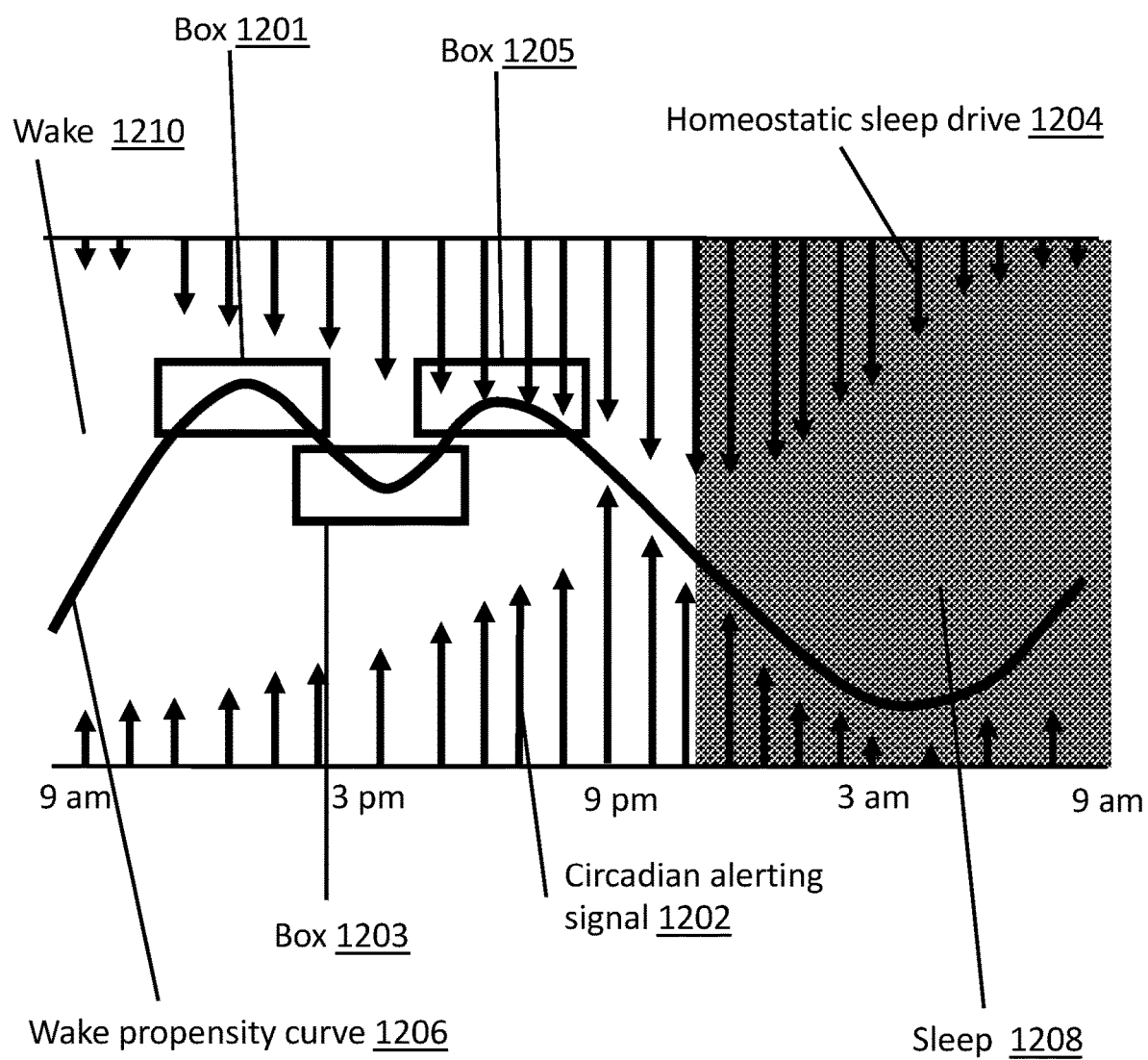

In the presence of substantial circadian phase misalignment such as night shifts or military deployment, full entrainment may not be physiologically feasible, but performances during a certain time frame may still be optimized and prioritized. In scenarios where full entrainment is not feasible, the primary parameter to optimize is the period of alertness when peak performance is desired. FIG. 12 shows how the wake propensity is regulated by Process C and Process S. In the plot, upward pointing arrows 1202 indicate the circadian signal for alertness, which promotes propensity to wake. Downward pointing arrows 1204 reprent the sleep homeostatic drive, which promotes propensity to sleep. The larger the arrow, the greater the propensity. A wake propensity curve 1206 is plotted, which is computed from the homeostatic sleep load and the circadian oscillation. The sleep period is represented as 1208, while the wake period is represented as 1210. While the homeostatic sleep pressure starts growing and keeps building up when the user is awake, late in the afternoon, the circadian signal for wakefulness kicks in and may override the homeostatic drive for sleep. The circadian alerting signal continues to increase into the night and peaks around 9 pm, offsetting the build-up of homeostatic pressure and allowing us to stay awake well into the evening and thereby achieve our human pattern of consolidated sleep and wakefulness. There is often a dip (shown as box 1203) in the late afternoon, when the homeostatic drive has been building for hours, but the circadian signal has not yet kicked in yet (that is the circadian signal has not yet become strong enough so that the person does not feel sleepy—but instead the person feels sleepy). If the application prioritizes performance during a certain time window while the user is awake, instead of shifting the circadian phase to a maximal magnitude, the model may shift the circadian phase, so that a time window with a local peak wake propensity, as shown in box 1201 and box 1205 in FIG. 12, are overlapped with the desired window when peak performance is requried. Alternatively, the model may shift the circadian phase so that the time with the local lowest wake propensity, as shown in box 1203, may be moved out of the desired window when peak performance is requried. In addition to suggesting the light therapy parameters for circadian phase shifts, the model may also suggest timing for naps or caffeine intake during wakefulness, among other factors that influence S, to achieve performance optimization.

In some circadian rhythm misalignment scenarios, especially during night shifts, during periods of partial sleep restriction or complete sleep restriction are involved, Process S and Process C are considered inter-dependent in the model. For example, scheduling of sleep and waking may alter the timing of light exposure and thereby affect the phase, amplitude, and/or period of C. Additionally, circadian rhythm adjustment in response to Zeitgeber may be less effective when the homeostatic sleep drive is high, which may change the circadian waveform between cycles when there is a partial or complete sleep restriction. Therefore, the impact of Process S on the shape of Process C needs to be considered. Meanwhile, where prolonged waking occurs, the circadian phase may modify the level of subsequent slow wave activity, so that the success of predicting the level of S may depend upon the time of day and not be simply a function of previous wake duration. In these scenarios, adjustments may be made in the model in order to compensate for the interaction. In an embodiment, the period (T), phase (c), and/or the amplitudes (a), may be functions of S. In at least one embodiment, an interaction between the C process and the S process and an interaction term may be added to C and/or S, which may have the forms of $\alpha*F(C_0, S_0)$, where $\alpha$ is a proportionality constant, "F(,)" represents an operation—which may be addition, convolution, correlation, and/or other operation, and $C_0$ and $S_0$ are the independent models, or alternatively the interaction term may have another form). For example, may be $S_0$ and $C_0$ are two different functions of time with different parameters). So for example, $\alpha*F(S,C)$ might be given by $\alpha*F(C_0,S_0)=\alpha*S_0(t)*C_0(t)$ (where "*" is just a simple mulitplicaiton) or it might be that $F(C_0,S_0)=S_0(t)/C_0(t)$ or it might be that $F(C_0,S_0)=\int S(t)C(t)dt$. Similarly, if $\alpha*F(C_0,S_0)=\alpha*S_0(t)*C_0(t)$, the full model may be represented as $f(t)=C_0(t)+S_0(t)+\alpha F(C_0,S_0)$ or $f(t)=C_0(t)+S_0(t)+\alpha C_0(t)*S_0(t)$.

In at least one of the embodiments, in use cases when light treatment is applied on multiple days, the circadian phase shift caused by light (Process L) may be introduced to model the new phase response curve after each treatment cycle either before or in the middle of the multi-day treatment program. The phase shift caused by the light programs $\Delta c$ may be modeled based on empirical data on the phase shifts caused by similar light treatment program that were measured physiological data collected from the lab using the circadian rhythm adjustment system or comparable treatment programs, or inferred by sleep/wake data and/or other data collected by the circadian rhythm adjustment system. In one embodiment, different light treatment program may be used throughout the course of the circadian rhythm adjustment, and different $\Delta c$ or different PRC may be used in the model based on the light treatment program utilized in the system on different days.

As an alternative to regression-based methods, time series for circadian markers can be analyzed using spectral methods such as Fourier analysis, periodograms, spectrograms, wavelet-based methods, autocorrelation, and Hilbert transforms. Other methods such as Bayesian spectral analysis and detrended fluctuation analysis may also be used to analyze and/or model circadian data. Depending on the input, different mathematical models may be chosen to generate the circadian rhythm adjustment program based on the magnitude of circadian rhythm misalignment, the time required for entrainment, and the sleep schedule constraints that may affect when the device may be used, and if and how sleep deprivation may affect the homeostatic sleep drive.

Model Output

Light therapy programs will be generated in the software (e.g., a mobile, desktop, or web-based application) based on the mathematical model outputs. In at least one embodiment, the main model output may include a prediction of circadian PRC based on the user's circadian clock on any point between the start and the end of the circadian rhythm adjustment, the type of light treatment used, and the expected circadian phase shifts caused by the light treatment. Based on the PRC, the CTO and the treatment windows in which light flashes can be delivered to advance or delay circadian phases will be determined. Based on the treatment windows and the user's sleep schedule constraints, a proposed sleep schedules will be generated. The light treatment program will be generated based on the timing of light pulse treatment and the other light flash setting such as intensity, duration, frequency, and wavelength, etc. In at least one embodiment, programs generated by the system to delay circadian phases happens during hour 15 to hour 24 (CT15-CT24), advance during hour 24 to hour 8 (CT24-CT8) of the subject's effective circadian time, in which CTO is defined as the cross-over point of the human phase-response curve. The cross-over point may be defined as the time of the fitted minimum of unmasked core body temperature. The system may predict the time that corresponds to CTO based on the information described before (the inputs to the C and/or S models), such as the user's biological profile, sleep schedules, travel or shift schedules, physiological data obtained from sensors, and/or other information obtained in lab studies.

In one embodiment, the system may generate a set of recommended treatment schedules to achieve the most optimized result and get feedback from the user about the feasibility of the schedule, based on which a final, negotiated schedule may be generated, and parameters of the mathematical model may be adjusted accordingly. In one embodiment, the system may generate a set of general recommended treatment schedules based on universal assumptions, and then adjust according to the user's specific variables that may impact their specific circadian rhythm computation. The mathematical model generated light treatment schedules may then be incorporated into a light program algorithm. A set of light therapy parameters of the treatment program may then be sent to the circadian rhythm adjustment hardware that delivers the light therapy, and the light therapy program (e.g., the treatment regimen) will be delivered to the user to shift circadian phases. The treatment may be a pattern of light pulses and/or other changes in lighting that are delivered to the user, via the circadian rhythm treatment apparatus that delivers the treatment (e.g., via a program that controls the lighting, such as by controlling pulses of light delivered to the user) to effectively treat or prevent circadian rhythm disorders. The treatment may be applied while the subject is asleep and/or awake in the middle of sleep or within 1-2 hours before or after sleep.

Alternatively, the model may output a basic function to estimate the circadian phase, the parameters of which may be data that can be captured from one or any of the combination of user input, sensors in the circadian treatment system, third party software, and/or third party hardware. Once the variables are input through the user interface, hardware sensors such as the ambient light sensor, and results from the lab studies, the model may generate an estimated PRC and windows in which light flashes or other light programs can be delivered to advance or delay circadian phases. In one embodiment, the model output may include recommendation for bedtime, wake time, light exposure, timings for meals, timings for exercise, and/or caffeine intake.

Based on the model output, light therapy programs including specific light therapy parameters may be generated and executed through the hardware in the circadian rhythm adjustment system. The light program may include different light pulse settings such as wavelength of the light, duration of pulses of light, interval of time during which pulses of light are delivered, the frequency of the pulses, the timing, and duration of the circadian rhythm disorder treatment program (e.g., via the light program). The light program may also include the timing, intensity, and wavelength of continuous light that works together or independently of the light flash program. The circadian rhythm treatment apparatus may deliver the treatment automatically and/or when activated. The user may have the option to adjust the parameters within the ranges that the manufacturer allows. For example, the user can choose different wavelengths of the light, different timings, and different durations of treatment administered by the mobile interface in the circadian rhythm disorder treatment program.

In at least one embodiment, as the user uses the circadian therapy program, more data on the changes and response to circadian rhythm shift may be gathered to establish a more accurate baseline (and improve information about the user's homeostasis sleep load), and the application may incorporate the data into computation of the circadian rhythm disorder treatment program (e.g., light program). In an embodiment, the light therapy program is dynamic and can be improved based on additional information collected each day from the user, the circadian rhythm treatment apparatus, or sensors in additional hardware. For example, there may be sleep sensors in the mask that track the sleep schedule and sleep/wake or stages of sleep of the user, such as by detecting the baseline of relevant physiological parameters, whether the user's eyes are closed, the user's head and body movements, the user's heart rate, and/or breathing pattern. The sensors may also collect information related to how alert the user is during a portion of the day. In one embodiment, a wearable light sensor that records ambient light exposure may be used as input to model/calibrate the circadian clock of the user each day. In one embodiment, the user may be asked about when and for how long they used the circadian rhythm treatment apparatus from the day before. In one embodiment, the information about circadian rhythm treatment device usage may be collected by a capacitive touch sensor that distinguish whether the device is in contact with the user's skin. The information may be used to calibrate the PRC estimation. In one embodiment, the system may contain a sample collecting and testing kit to measure physiological biomarkers for circadian rhythms, such as melatonin level in saliva, blood, or urine. The level of these biomarkers may be detected via assays run in real time, the results of which may be used to establish the baseline or to refine the model. The model may first establish a baseline shift program based on the average shift that can be achieved on a look-alike populational level, and then the application may adjust itself based on the sleep time of the user once the program starts. For example, if the mask (and/or system) determines that the user has achieved the entire shift in the user's circadian rhythm earlier than the populational average time for achieving the same shift in circadian rhythm, then the program may stop. The user can also stop the program manually based on how adjusted the user feels.

Figure 14:
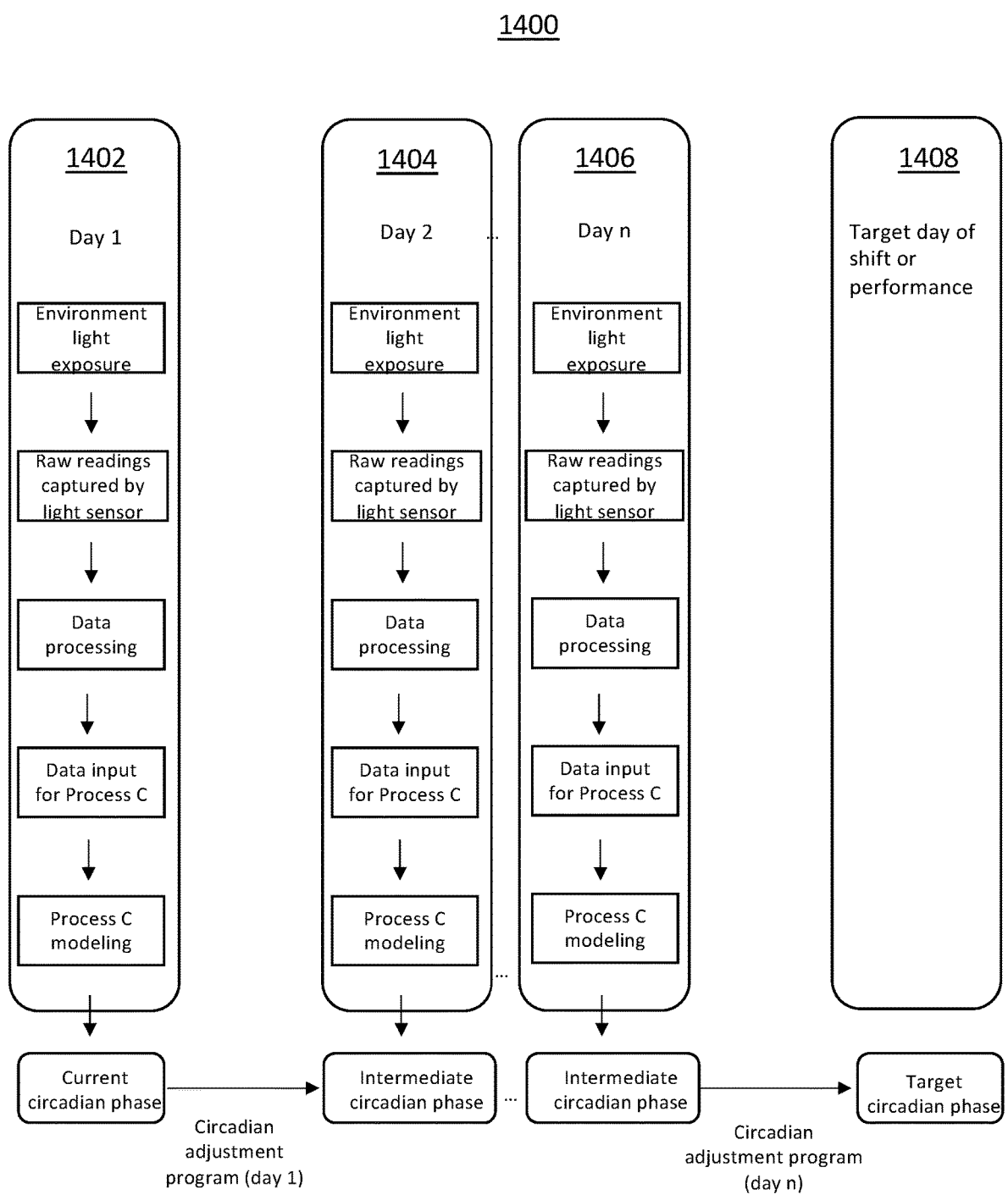
FIG. 14 shows a diagram of how the circadian rhythm treatment program may be adjusted throughout the course of the treatment based on sensor input.

There may be a feedback mechanism to further calibrate the model or improve the circadian rhythm adjustment program throughout the treatment process. In at least one embodiment, the light therapy program may be dynamic and may be improved based on additional information collected each day from the user or from sensors on the circadian rhythm treatment apparatus. As the user uses the circadian therapy program, more data on the changes and response to circadian rhythm shift may be gathered to establish a more accurate estimate on the user's circadian rhythm and homeostasis sleep pressure. The data may be fed into the model and adjust the circadian phase shift program accordingly. For example, in at least one embodiment, the system may record sleep information from a prior day (or other prior time period) or from real time information to know how much of a shift has been generated in a user, and the predicted PRC may be refined. Then based on one or more of the refined model, the refined model output, and the refined predicted PRC, the light therapy instructions may be adjusted to improve treatment efficacy. In at least one embodiment, the circadian rhythm adjustment system uses data captured from a wearable ambient light sensor to adjust the circadian rhythm treatment program on a daily basis. As shown in flow chart 1400 of FIG. 14, step 1402 illustrates the process of collecting the ambient light sensor reading and using it as part of the model input. Based on the ambient light data, a current circadian phase of the user may be computed, and a circadian rhythm adjustment program may be proposed based on the user's target circadian phase. As shown in step 1404, a similar process of data collection may also be performed on day 2. Based on the ambient light data input, together with other user feedback such as when the user slept and used the mask the date before, an updated circadian rhythm adjustment program may be proposed based on the user's circadian phase on day 2 and the target circadian phase. The process may repeat until the end of the treatment regimen. Step 1406 is an example of process of data collection that leads to light treatment program update on day N. In step 1408, if the circadian phase shift has not been achieved to the desire level on the target day of shift or performance based on user feedback or sensor data, a similar program adjustment process as steps 1402-1406 may be initiated. In one embodiment, different light treatment program may be used throughout the course of the circadian rhythm adjustment, and different Δc or different PRC may be used in the model based on the light treatment program utilized in the system on different days.

FIGS. 15, 16, and 17 show an exemplary methods for adjusting a user's circadian rhythm. In some embodiments, the methods shown in FIGS. 15, 16, and 17 may be performed using any of the systems described above with respect to FIG. 1-14. In FIGS. 15, 16, and 17, dashed lines indicate optional steps. Steps shown in solid lines may also be omitted in some embodiments.

FIG. 15 shows an exemplary method 1500 which may generally include steps of collecting input, generating a circadian rhythm adjustment program, and delivering treatment in accordance with the generated instructions. In step 1502, the system may collect information related to the user's present circadian rhythm. Such information may include the user's biological profile and sleep profiles, schedules about sleep and/or wakefulness, environmental light exposure, and chronotype. The data may be collected via a user interface on a software, from sensors in device, from lab assays, and/or other software or hardware such as a wearable tracker, a central software data source such as Apple Health, a calendar system, or a work scheduling system. In at least one embodiment, the biological profile may include the user's age, sex, eye color, pupillometry, weight, height, amount of exercise, light sensitivity, etc. In at least one embodiment, information about the user's sleep profile may include the user's typical bedtime and wake time, the typical sleep efficiency, the number of hours the user ordinarily sleeps, the number of times the user gets up in the night, whether the user has a form of insomnia, sleep apnea, or other sleep disorder. In one embodiment, the sleep profile may also include the chronotype of family members. In at least one embodiment, the inputs for the model may include data specifically about the user, collected via wearable devices and/or other device, via an APIs of software applications, via a user interface of an application, and/or through hardware in a sleep mask or devices from which the light flashes are delivered. In at least one embodiment, the information may include data collected sensors in the circadian rhythm treatment device, or sensors from other wearables such as actigraphy. In at least one embodiment, the data may include ambient light data from a wearable light sensor in the form factor of a pin, a button, a brooch, a necklace, or an earring, or some form factor that can be worn around the neck/chest area facing generally the same direction as the user's face to mimic the amount of light received in the user's eyes throughout the day. In at least one embodiment, the inputs for the model may include data collected from look-alike demographics in laboratorial studies, or studies conducted by other organizations. For example, benchmark biological markers may include any one of, or any combination of pupillometry, iris color, salivary melatonin, core body temperature, plasma cortisol, plasma melatonin, and urinary melatonin that can be collected in appropriately controlled inpatient environment and used to estimate properties of the central circadian pacemaker. In one embodiment, the salivary Dim Light Melatonin Onset (DLMO) data may be obtained in lab studies upon light treatment. In one embodiment, salivary or urinary melatonin may be collected and analyzed in the lab or by an analysis kit operated by the user. In one embodiment, ambient light exposure data, sleep diaries, and other self-reported survey data may be obtained in lab studies. In one embodiment, the information includes genetics information correlated with circadian rhythms, chronotypes, sleep conditions or disorders, which may be obtained from laboratory assays on sample collected from the user and/or third-party sources containing genetic testing information about the user, for example, personal genomics companies such as 23andMe. In at least an embodiment, multiple users may use the same device at different times. Each user may have his/her own account with past programs, biological, sleep, homeostasis sleep load profiles, and behavioral profiles. Based on the information collected throughout the time that user uses the circadian rhythm treatment apparatus, the software adjusts and improves itself to provide personalized circadian rhythm disorder treatment program (e.g., light program).

In optional step 1504, the system may collect information relating to one or more anticipated times of sleep and/or wakefulness, for the user, on one or more days. In some embodiments, this step collects any one of, or any combination of, the user's current and target sleep schedules, travel information, time zone information, work shift schedule, sleep constraints (e.g. from work and social activities), sleep schedule preferences, daylight saving information, and/or other information to understand the circadian phase shift needs. In at least one embodiment, the information may include past and/or present times of sleep and/or wakefulness. In at least one embodiment, the information may be collected from user input via a software interface. In at least one embodiment, the information may be collected from a GPS location or a location-specification system. In at least one embodiment, the information may be collected via a calendar system, a flight-scheduling system, or a work-scheduling system. In at least one embodiment, the information may be collected from time zone information, latitude information, sunrise/sunset times information via a GIS system. In at least one embodiment, the information may be deduced from past activities or schedule templates derived from past activities. In one embodiment, the difference between current and target sleep schedules may be collected in a format of certain magnitude of circadian phase misalignment (e.g. 3 hours of circadian phase misalignment). In at least one embodiment, the information to estimate current and/or target circadian rhythm phase may be collected by an ambient light sensor. The circadian rhythm treatment system can be used before, during, and/or after the occurrence of the change of sleep schedules or time zones or anytime when the user would like to improve sleep through optimizing circadian rhythms and alertness. In at least one embodiment, the user may input the travel schedules, work schedules, or any change of sleep and wake schedules that have started before entering the program. In one embodiment, the input information may include timing and length of naps, the intake of caffeine and other substances that may impact sleep and wakefulness. In at least one embodiment, the user may have the option of setting up step 1504 via modifying a preexisting template or a template created from a past schedule change. For example, the system may display in a user interface proposed times for sleeping and/or waking. The user may provide feedback, which may include accepting proposed times, rejecting proposed, and/or adjusting proposed times. Based on the user feedback, new proposed times for sleeping and/or waking may be recommended. In at least one embodiment, the user may have the option of turning any of their current or past step 1504 settings into a template and then repeat it with modifications as necessary.

Based on at least the information relating to the user's circadian rhythm, in step 1506, the system may generate a model for estimating the user's circadian rhythm over one or more days in response to the application or anticipated application. The estimates of the user's circadian rhythm may be configured to be adjusted in response to changes in the user's sleep and wakefulness times. The estimation of circadian rhythm over one or more days may be computed via estimation of PRC with certain treatment plan delivered via specific light patterns (for example, light flashes with certain intensity and frequency). In at least one embodiment, the estimation of circadian rhythm (Process C) may be modeled based on the magnitude of circadian rhythm misalignment, the number of days to adjust, and an estimated PRC for the user. In one embodiment, the PRC may be estimated based on human-subject study data (for example, light exposure data and melatonin data) using treatment programs determined to be representative for the user's treatment program (e.g., where both the user's treatment and the representative treatment use light flash treatment with intensity, duration, and frequency values within a specified range). In one embodiment, the PRC may be proximally estimated based on data from human-subject studies with other light treatment programs, and then calibrated based on additional information such as user feedback on how well the device works, sleep measurement, alertness measurement, and/or via data collected from sensors. In one embodiment, a proximal PRC based on data from human-subject studies with other light treatment programs may be used without further calibration.

Additionally and selectively, concurrently or subsequently, optional step 1508 may generate a model for estimating the user's homeostatic sleep drive (Process S) over one or more days, based on at least one or more current, past, and anticipated times of sleep and/or wakefulness. The estimates of the user's homeostatic sleep drive may be configured to be adjusted in response to changes in the user's sleep and wakefulness times. Based on information collected in step 1502, in one embodiment, the estimated of the user's homeostatic sleep drive may be based on the time of wakefulness in the past days. In one embodiment, the estimate of Process S is based on the anticipated time of wakefulness in one or more days. In at least one embodiment, the system may have the choice to skip calculating Process S depending the user's information input from step 1502 and 1504. In one embodiment, the system may calculate Process S using information such as the timing and duration of naps, or intake of caffeine or other substances, or other factors that may impact sleep and wakefulness. In one embodiment, the system may recommend sleep and wake schedules and/or nap schedules during the period of wakefulness as part of the treatment program.

After computing Process C and Process S, the system may then generate instructions to activate the light source to adjust the user's circadian rhythm, as shown in step 1510. Optionally, the step of generating instructions 1510 may be performed based on the models generated in step 1506 (circadian rhythm model) and optional step 1508 (homeostatic sleep drive model). For example, a user's PRC may indicate that to shift forward or backward the user's sleep schedule a desired amount, light flashes should be applied at a certain point during the user's circadian rhythm. The system may thus use the modeled estimate for the user's circadian rhythm to apply the light flashes during the correct time period to achieve the desired result. A model of homeostatic sleep drive may likewise be considered in specifying instructions for light flash treatment. For example, if the user has work shifts at irregular times, the user may need to be awake or asleep at times that deviate from what would ordinarily be expected, and using only a PRC based on circadian rhythm may not fully predict how timed light flashes will shift the user's circadian rhythm and times of wakefulness and sleep. By taking into account the user's estimated homeostatic sleep drive, both at present and over one or more days in the future, the timing of applied light flash treatment may better aligned with the times needed to achieve a desired shift to the user's circadian rhythm.

The instructions may include the timing of the light treatment program. In at least one embodiment, the treatment program may be a pattern of light pulses and/or other changes in lighting that are delivered to the user without waking up the user. In at least one embodiment, the treatment program may be a pattern of light pulses with period(s) of continuous light. Optionally, the user may use the continuous light program, by itself, without the circadian rhythm treatment program. For example, the continuous light program may be used for morning wake up, or may be supportive of an audio for meditation, which may be used with or without a circadian rhythm program in which a pattern of light pulses is delivered. In at least one embodiment, the light pulses may be designed with settings such as wavelength of the light, duration of pulses of light, interval of time during which pulses of light are delivered, the frequency of the pulses, intensity of the light applied during the pulses, the timing, and duration of the circadian rhythm disorder treatment program (e.g., via the light program). In at least one embodiment, the treatment program may be represented as blocks or trains of light flashes with various intensity, duration, frequency, and wavelength that start and stop at different times during sleep. Each light program may have two treatment windows as the result of the computation of Process C and/or Process S: the advance window is a time period in which the occurrence of light flashes may advance the circadian phase, and the delay window is a time period in which the occurrence of light flashes may delay the circadian phase. Within each window there may be one or multiple light flash treatment blocks, which is a period of time when light flashes happen. The treatment blocks may be adjacent to each other, or separated by a block of time when no light flashes occur. In one embodiment, one of more treatment blocks may be continuous light. In another embodiment, one or more of the treatment blocks may contain no lights.

In some embodiments, default settings of light patterns may be provided. For example, default settings may include the timing of blocks and the intensity, duration, and frequency of the light flashes within the blocks. The timing of blocks may be based on the models for circadian rhythm and/or homeostatic sleep drive. In some embodiments, the instructions may specify for light flashes to be applied that have an intensity between 25 and 5,000 lux and a duration between 1 picosecond and 500 milliseconds. The instructions may also specify that the light flashes should be applied at a frequency between once per 5 seconds and once per 120 seconds.

In at least one embodiment, the manufacturer may provide a default setting for the light flash parameters and/or provide the user the ability to adjust the settings. For example, in at least one embodiment, the manufacturer may provide a default intensity of 100 lux or even 50 lux at eyelid level before eyelid penetration for user with combination of certain biological traits that result in high light sensitivity, and a default intensity of 3000 lux or even 5000 lux eyelid level before eyelid penetration for user with combination of certain biological traits that result in low light sensitivity, and values in between for users with combination of certain biological traits that result in intermediate light sensitivity. Similarly, in at least one embodiment, the manufacturer may suggest initial light flash frequency settings based on the user's biological profile (such as age and/or eye color) and self-reported light sensitivity and how heavy a sleeper the user is, and based on human-subject studies on light flash frequency and sleep disruptions. For example, the manufacturer may provide a default light flash frequency of once per minute for user with combination of certain biological traits that result in high light sensitivity, and a default light flash frequency of once per 8 seconds for user with combination of certain biological traits that result in low light sensitivity, and values in between for users with combination of certain biological traits that result in intermediate light sensitivity. In at least one embodiment, different light flash intensity or frequencies are used at different times of the sleep to achieve the most substantial circadian phase shift without causing sleep disruptions. For example, a lower light flash frequency or lower intensity, or the combination of both, are used for the same user in the later part of the sleep when the homeostatic sleep pressure dissipates and therefore easier for the user to wake up.

The instructions to activate light program for circadian rhythm misalignment treatment in step 1510 may applied by a circadian rhythm adjustment apparatus to deliver the treatment program, which is shown in optional step 1512. Based on the instructions, the circadian rhythm adjustment apparatus may activate the light source (e.g. an LED) during a treatment window to adjust the user's circadian rhythm. In at least one embodiment, the treatment program may be delivered via a sleep mask. For example, the sleep mask may emit light flashes through a removable insert with electronics. In another embodiment, the light programs can be delivered in glasses or goggles. In one embodiment, the circadian rhythm treatment apparatus may include in-room lighting (controlled by a controller) that works with a mobile application that generates light programs based on circadian modeling algorithms to treat or prevent circadian rhythm disorders. In at least one embodiment, the light pulses use light sources that produces a wavelength between 380 to 750 nm. In at least one embodiment, a subset of the wavelength 380 to 750 nm for a specific segment of the light treatment, so different treatment segments may have different color. For example, a wavelength 380 to 750 nm may be used for the circadian rhythm adjustment program during sleep, a wavelength 600 to 750 nm may be used for the treatment towards the end of sleep, and wavelengths 380 to 550 nm may be used for treatment before bed, or a combination of different subsets of the color spectrum within one treatment segment.

Optional step 1514 describes a feedback collection mechanism to obtain updated information to improve the system, including information relating to circadian rhythm, user feedback, device usage, and/or the efficacy of the instructions for activating the light source during at least the treatment window. The data may be used to establish, modify, or choose the most applicable algorithm to use, and/or as input for the algorithm to generate the circadian shifting program, updated circadian rhythm alignment needs, and/or as feedback to evaluate the effect of the program and make necessary adjustments to the program. In one embodiment, the light treatment may be applied during an initial treatment window. After the initial treatment window, the user may be asked to answer questions about their experience using the device, and/or their sleep and alertness condition, based on the answers of which the system makes the adjustment in the instructions to activate the light source. In one embodiment, the user may have the option to update any changes in their schedules for sleep and wakefulness. In one embodiment, a wearable light sensor that records ambient light exposure may be used as input to model/calibrate the circadian clock of the user each day. In one embodiment, the user may be asked about when and for how long they used the circadian rhythm treatment apparatus from the day before. In one embodiment, the information about circadian rhythm treatment device usage may be collected by a capacitive touch sensor that distinguish whether the device is in contact with the user's skin. The information may be used to calibrate the PRC estimation. In one embodiment, the system may contain a sample collecting and testing kit to measure physiological biomarkers for circadian rhythms, such as melatonin level in saliva, blood, or urine. The level of these biomarkers may be detected via assays run in real time, the results of which may be used to establish the baseline or to refine the model. In one embodiment, the user may have the option to adjust light intensity, frequency, or other light program parameters based on their experience using the device. In one embodiment, the system may evaluate the level of sleepiness or alertness of the user via neurocognitive measurements for, including any one of, or any combination of, reaction times, processing speed. memory. laguage skills, coordination and motor skills. executive function, and emotional stability, and so on. In at least one embodiment, the feedback includes information captured from sensors that monitor sleep and wakefulness during the treatment process, for example, motion sensor, brainwave sensor, breathing sensor, pulse sensor, microphone, and so on. For example, the system may record sleep information from a prior day (or other prior time period) or from real time information to know how much of a shift has been generated in a user, and the predicted PRC may be refined. Then based on the refined model and the refined model output, the light therapy algorithm may be adjusted accordingly. For example, updated instructions may be generated and, based on those updated instructions, light treatment may be applied during a second treatment window. Further information may be acquired after the second and subsequent treatment windows, and any number of adjustments and modified instructions may be generated through any number of cycles of treatment and feedback.

Based on information collected from step 1514, in optional step 1516, the system may adjust the instructions as necessary for activating the light source to adjust the user's circadian rhythm. The system may recalculate any one of, or any combination of, the user's current circadian rhythm, target circadian rhythm, circadian rhythm realignment needs, recommended sleep schedules, light program parameters such as intensity, frequency, duration, wavelength, and timing, based on updated information. In at least one embodiment, the system may reduce the light intensity, pulse duration, and/or frequency, or the combination of both, if the system detects or the user reports sleep disruptions during the light program. In at least one embodiment, the system may recalculate the PRC if the user forgot to use the device or did not use the device according to the treatment protocol in prior day(s). In at least one embodiment, the system may recalculate the sleep and/or treatment window if the user reports updated sleep or wake schedules, time zones, flight information, or sleep time constraints. In at least one embodiment, the system may infer the efficacy of circadian rhythm alignment for a specific user based on the level of sleepiness or alertness of the user, or the sleep information collected from the sensors. In at least one embodiment, the system may increase the light intensity, pulse duration, and/or frequency if the user reports excess sleepiness at a time indicating that the expected shift to the user's circadian rhythm has not been achieved. Based on these data, the system may establish a baseline, as part of the user's long-term profile, of how sensitive this user's circadian rhythm is to light treatment programs, and use this information as model input to update the algorithm that generates the circadian rhythm treatment instructions in steps 1506, 1508, and 1510. In some embodiments, step 1516 may be performed using any of the details described below with respect to step 1712.

Optionally, in at least one embodiment, most of the information relating to the user's present circadian rhythms may be collected via sensors. FIG. 16 shows an exemplary method 1600 for adjusting a user's circadian rhythm using input from sensors. In some embodiments, method 1600 can be performed using any of the systems described above with respect to FIG. 1-14. In step 1602, the system may obtain information relating to times of sleep and/or wakefulness using a sensor. In at least one embodiment, the sensor may be an environment light sensor to collect light exposure to infer the user's present circadian rhythm. In at least one embodiment, the light sensor may be a wearable light sensor in the form factor of a pin, a button, a brooch, a necklace, a chocker, or an earring, or some form factor that can be worn around the neck/chest area. The light-capturing part of the hardware generally faces the same direction as the user's face, to maximally mimic the amount of light received in the user's eyes. The user may wear the light sensor for as much as possible throughout the day except when showering and sleeping. When the user is sleeping, the light sensor may still be put facing upward next to the user's head to record the environmental light intensity in the bedroom during the time when the user is sleeping. The wearable light sensor records the amount of light that the user's eyes are exposed to throughout the day. In at least one embodiment, the sensor may be motion-based to estimating the timing and quality of sleep for the user, such as 3-6 axis accelerometers and a gyroscope. In at least one embodiment, a capacitive touch sensor may be used to determine whether a device is being worn by the user based on data obtained from the capacitive sensor.

In optional step 1604, the system may collect information relating to one or more anticipated times of sleep and/or wakefulness, for the user, on one or more days. For example, any of the information described above with respect to step 1504 may be collected in step 1604. Based on at least the information relating to the user's circadian rhythm, in step 1606, the system may then generate a model for estimating the user's circadian rhythm over one or more days in response to the application or anticipated application. The estimates of the user's circadian rhythm may be configured to be adjusted in response to changes in the user's sleep and wakefulness times. For example, step 1606 may be performed as described above with respect to step 1506. In step 1608, the system may then generate instructions to activate the light source to adjust the user's circadian rhythm. Step 1608 may be performed generally as described above with respect to step 1510. In step optional 1610, based on the generated instructions, the system may activate the light source in the circadian rhythm treatment device during a treatment window to adjust the user's circadian rhythm. In at least one embodiment, the treatment program may be delivered via a sleep mask that emits light flashes through a removable insert with electronics. In another embodiment, the light programs can be delivered in glasses or goggles. In one embodiment, the circadian rhythm treatment apparatus may include in-room lighting (controlled by a controller) that works with a mobile application that generates light programs based on circadian modeling algorithms to treat or prevent circadian rhythm disorders. Step 1610 may be performed as described above with respect to step 1512.

In optional step 1612, the system may obtain updated information relating to circadian rhythm via user feedback and/or sensors throughout the treatment process. The data may be used to establish, modify, or choose the most applicable algorithm to use, and/or as input for the algorithm to generate the circadian shifting program, updated circadian rhythm alignment needs, and/or as feedback to evaluate the effect of the program and make necessary adjustments to the program. In at least one embodiment, the sensor may be an environment light sensor to collect light exposure to infer the user's present circadian rhythm. In at least one embodiment, the light sensor may be a wearable light sensor. In at least one embodiment, the sensor may be motion-based to estimating the timing and quality of sleep for the user, such as 3-6 axis accelerometers and a gyroscope. In at least one embodiment, a capacitive touch sensor may be used to determine whether a device is being worn by the user based on data obtained from the capacitive sensor to infer when the user uses the device in prior days. In at least one embodiment, the user may be asked to answer questions about their experience using the device, and/or their sleep and alertness condition, based on the answers of which the system makes the adjustment in the instructions to activate the light source. In one embodiment, the user may have the option to update any changes in their schedules for sleep and wakefulness. In one embodiment, the feedback may also include neurocognitive measurements to evaluate the user's sleepiness and alertness level. The information collected in step 1612 may also be collected in step 1514, described above with respect to FIG. 15. Based on information collected in step 1612, in step optional 1614, the system may adjust the instructions for activating the light source to adjust the user's circadian rhythm. This step may be performed as described above with respect to step 1516.

Light Settings

The circadian rhythm model output, for example, timing of the treatment windows to advance and delay circadian rhythm, will be integrated into a light program algorithm that generates the light program for circadian rhythm adjustment treatment. In one embodiment, the circadian rhythm treatment systems use light pulse to treat circadian rhythm misalignment. The light pulses may be designed with settings such as wavelength of the light, duration of pulses of light, interval of time during which pulses of light are delivered, the frequency of the pulses, the timing, and duration of the circadian rhythm disorder treatment program (e.g., via the light program). Depending on the light sensitivity of the user, light pulses of different intensity may be delivered to effectively treat the user (treating or preventing circadian rhythm disorder) without waking up the user. Due to retinal physiology and the sensitivity of the circadian adjustment system in the brain, light flash stimulation at night can potentially be more effective in shifting circadian rhythm than continuous light stimulation during the day. In any of the embodiments, the light flashes can be received either through the eyelids (of closed eyes) when the user is sleeping or resting, or directly into open eyes when the user is awake during the night or within 1-2 hours before or after sleep. Some users may, at times, sleep with their eyes open, some users may wake up in the middle of sleeping, and some users may at times rest their eyes in the middle of the day without going to sleep. The intensity of the lights may be adjusted based on whether or not the light needs to penetrate through the eyelids.

In at least one embodiment, the light therapy parameters may be sent to the hardware to execute the light program that uses light flashes to shift circadian phases. In at least one embodiment, a light-pulse-program may be used alone or in combination with a continuous light program before sleep, towards the end of sleep, and/or after waking up. The continuous light program may accompany and/or complement a circadian rhythm program, which may have different uses, settings, such as wavelength of the light, the timing of the light, and the duration of the light treatment. Optionally, the user may use the continuous light program, by itself, without the circadian rhythm treatment program. For example, the continuous light program may be used for morning wake up, or may be supportive of an audio for meditation, which may be used with or without a circadian rhythm program in which a pattern of light pulses is delivered. The morning or evening continuous light that is independent of the circadian rhythm-adjusting light flashes may have a different wavelength range than the white flashes.

The manufacturers may implement light therapy regimen (for example, a light flash program) with specific intensity, frequency, duration, wavelength, timing and reoccurring patterns. The manufacturer may provide a default setting for the light flash parameters and/or provide the user the ability to adjust the settings. The light settings provided by manufacturer may be based on results from lab studies or other human-subject studies. For example, the manufacture may use white light emitted from LED that covers the full spectrum or a subset of the full spectrum of the visible light (380 nm to 750 nm), the spectrum of colors used to make up the white light may imitate the spectrum of light emitted by the Sun at midday, Sunrise, or Sunset. The manufacturers may also choose a subset of the wavelength 380 to 750 nm for a specific segment of the light treatment, so different treatment segments may have different color. For example, the manufacturer may choose wavelength 380 to 750 nm for the circadian rhythm adjustment program during sleep, wavelength 600 to 750 nm for the treatment towards the end of sleep, and wavelengths 380 to 550 nm for treatment before bed, or a combination of different subsets of the color spectrum within one treatment segment.

Figure 13:
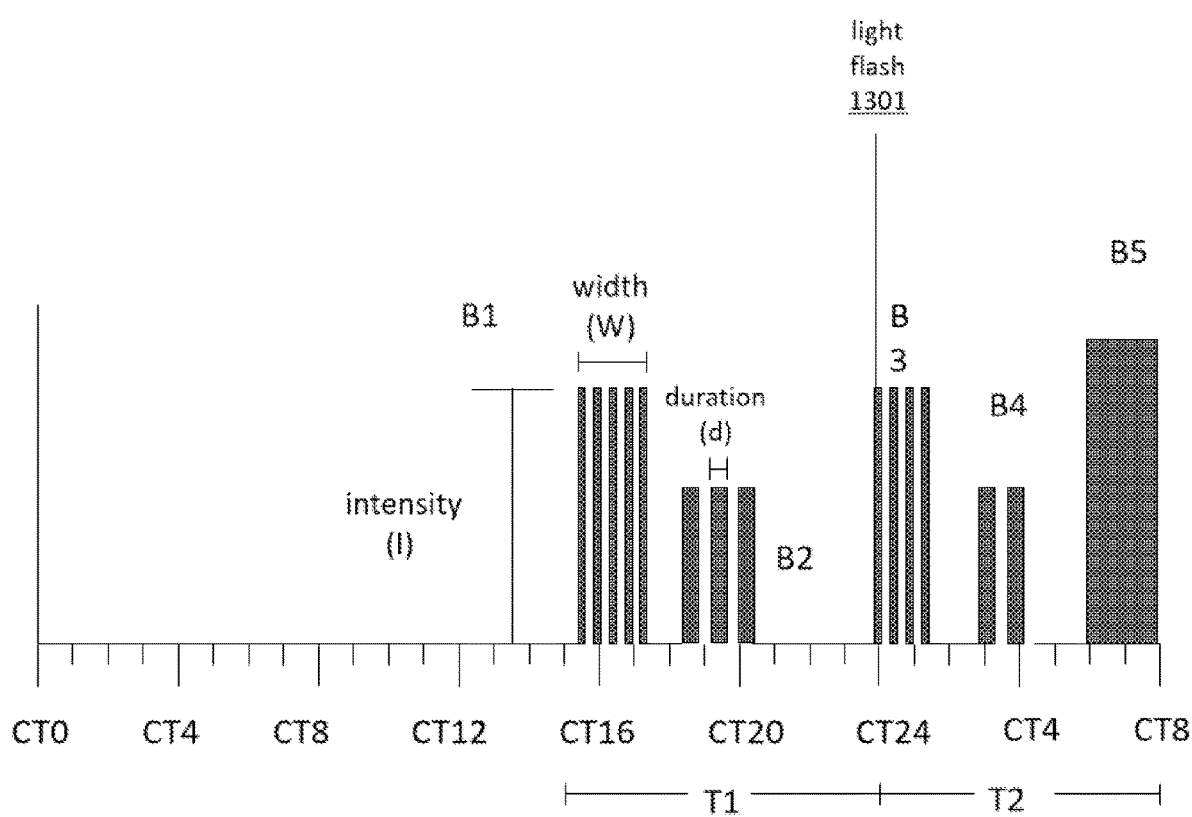
FIG. 13 shows an example of one or more blocks of light flashes to illustrate the light flashes parameters.

The light flash programs to treat circadian rhythm misalignment may follow specific designed multi-block patterns. Each light program has two treatment windows: the advance window is a time period in which the occurrence of light flashes may advance the circadian phase, and the delay window is a time period in which the occurrence of light flashes may delay the circadian phase. Within each window there may be one or multiple light flash treatment blocks, which is a period of time when light flashes happen. FIG. 13 shows an example of a treatment regimen 914 for treating circadian rhythm, which may include two treatment windows T1 and T2. In at least one embodiment, T1 and T2 are outputs of the circadian rhythm-estimating mathematical model. In at least one embodiment, T1 occurs during hour 15 to hour 24 (CT15-CT24) cause the user to wake later and T2 occurs during hour 24 to hour 8 (CT24-CT8) of the subject's effective circadian time cause the user to wake earlier. The time CT0 is defined as the cross-over point of the human phase-response curve or is defined as the time of the fitted minimum of unmasked core body temperature, deducted based on information, such as the user's biological profile, sleep schedules or other information such as core body temperature. In the notation CTxx (where xx is a one-two digit number, as in CT12), CT stands for Circadian Time, and CTxx is defined as the time of activity onset in a free-running human.

The advance and delay treatment windows T1 and T2 may each contain blocks of flashes. FIG. 13 shows an example of one or more blocks of light flashes within the treatment windows. Each filled bar 1301 represents one light flash or continuous light for a period of time. T1 may contain multiple light flash blocks (B1 and B2 in FIG. 13), and T2 main contain multiple treatment blocks (B3, B4, and B5 in FIG. 13). In this specification, the term "block," as in a block of flashes, refers to a "train" of flashes. The terms a "block of flashes" and a "train of flashes" are used interchangeably throughout this specification, and may be substituted one for another to obtain different embodiments. Each treatment block may have the same light flashes with one set of light parameters such as light intensity I, flash duration d which represents how long each light flash lasts, and the light flash frequency f. The treatment blocks may be adjacent to each other, or separated by a block of time when no light flashes occur. In one embodiment, one of more treatment blocks may be continuous light. In another embodiment, one or more of the treatment blocks may contain no lights. The period P is the time between a particular point in the cycle of the turning the flash on and then off or off and then on (e.g., the start of one flash) and the point on the next cycle (e.g., the start of the subsequent flash). The frequency of the flashes may be computed from the period, P, according to the formula $f=1/P$. In each treatment window there may be multiple blocks, the duration of the whole block is represented as width W. Each block of flashes may have one width that are the same or different from another block. However, the term "block" may also refer to a block without any flashes.

The manufacturer may provide a default setting of light patterns, including the timing of blocks and the intensity, duration, and frequency of the light flashes within the blocks. The timing of blocks may come from the output of the mathematical model. The flash patterns over a certain chosen period of time may be pre-determined by the manufacture based on the mathematical model output, and may be adjusted based on user input and/or data collected from sensors or other wearables or applications. In an embodiment, the total treatment period is at least 5 minutes long. In an embodiment, the treatment period is 240 minutes long or less. In one embodiment, the manufacturer may set the number of blocks with their timing and width (for example, any number of minutes between 5 minutes and 240 minutes). The manufacturer may also provide a default setting for the light flashes within each block. The specific treatment time within above time periods for adjusting the circadian rhythm may be further refined based on the impact the user's homeostatic sleep drive. The user may have the options to adjust the treatment windows or to provide feedback on how the treatment windows may be adjusted. The treatment windows may also be adjusted based on data collected from sensors in the system and/or other wearables or software.

Light flash intensity within block is chosen so as to be high enough to achieve efficacy, but low enough so as to not be uncomfortable or disruptive of user's sleep. Light intensity may be initially set to default values based on an intensity that an average individual finds comfortable and still results in an effective treatment. Alternatively or additionally, the initial setting may be determined according study results on human subjects with similar biological traits or light sensitivity who report sleep disruptions with different levels of light intensity, as higher intensity may lead to more substantial circadian phase shift, but could also increase the risk of sleep disruption. The manufacturer may suggest initial light intensity settings based on the user's biological profile (such as age and/or eye color) and self-reported light sensitivity and how heavy a sleeper the user is. The initial setting of light intensity may come from human-subject studies on light flash intensity and sleep disruptions. The user may later adjust the settings to what works best for that individual. Alternatively or additionally, the light intensity values may be adjusted automatically based on sensor reading, for example, on sleep disruptions. For example, the manufacturer may provide a default setting of how bright a flash of between about 100 microseconds –1 milliseconds. The flash may have a default intensity of 3000 lux at eyelid level before eyelid penetration set by the manufacturer, with an adjustable range of 50-4000 lux at eyelid level before eyelid penetration. In an embodiment in which the flash duration is between about 100-500 microseconds, the intensity of the light flashes may be 100-3000 lux as measured at the level of eyelid before penetrating through the eyelid. The manufacturer may provide a default intensity of 100 lux or even 50 lux at eyelid level before eyelid penetration for user with combination of certain biological traits that result in high light sensitivity, and a default intensity of 3000 lux or even 5000 lux eyelid level before eyelid penetration for user with combination of certain biological traits that result in low light sensitivity, and values in between for users with combination of certain biological traits that result in intermediate light sensitivity. The user may adjust the light intensity setting to anywhere between 300, 600, 1000, or even 3000 lux at eyelid level before penetration based on system feedback or the user's own experiencing using the device. In an embodiment in which the flash duration is between about 1-5 milliseconds (e.g., 3 millisecond), the intensity of the flash may be 750-3000 lux as measured at the level of eyelid before penetrating through the eyelid. The manufacturers may provide a default setting of light intensity based on the user's self-reported light sensitivity. In an embodiment in which the flash duration is less than 1 microsecond, the intensity may be 1000 lux or higher, such as, as high as 4000 or 5000 lux, measured at the level of eyelid before penetrating through the eyelid. In an embodiment in which the user is sleeping or resting with closed eyes or awake (or sleeping) with open eyes, the intensity may be at least 25 lux, 100-1000 lux, or 50-500 lux, or 100-5000 lux measured at the level of the open eye or at the level of eyelid before penetrating through the eyelids so the user has the flexibility of adjusting based on their sleep/wake situation. In the embodiments which apply when the user is sleeping or resting with closed eyes, the light intensity of flashes is determined partially based on the eyelid attenuation assumption used in some sleep research, in which on average about 10% full-spectrum light penetrates through the eyelid. Compared to using sensors to measure attenuation and then to determine the flash intensity, this assumption simplifies the device design, avoid components that are potentially uncomfortable for the user's eyes, and prolongs the battery life of the device.

The manufacturer may provide a default setting of how frequently a flash is repeated over a period of time. Higher flash frequency may lead to more substantial circadian phase shift, but could also increase the risk of sleep disruption. The manufacturer may provide initial frequency settings based on results of human-subject studies with look-alike populations to investigate the effect of light flash frequency and sleep disruption, together with user input and/or sensor data. The user may be provided the option to choose the frequency. For example, the light flash may be set to be any numbers between about 0.2 Hz to about 8.3 millHz (once every 5 seconds to once every 120 seconds) based on the effect of light flash frequency on circadian phase shifts. The manufacturer may suggest initial light flash frequency settings based on the user's biological profile (such as age and/or eye color) and self-reported light sensitivity and how heavy a sleeper the user is. The initial setting of light flash frequency may come from human-subject studies on light flash intensity and sleep disruptions. For example, the manufacturer may provide a default light flash frequency of once per minute for user with combination of certain biological traits that result in high light sensitivity, and a default light flash frequency of once per 8 seconds for user with combination of certain biological traits that result in low light sensitivity, and values in between for users with combination of certain biological traits that result in intermediate light sensitivity. The manufacturer may adjust the light flash frequency based on user feedback, or provide the settings that allow the user to adjust the frequency. The manufacturer may provide a set of default light flash frequencies used at different times of the sleep to achieve the most substantial circadian phase shift without causing sleep disruptions. For example, the manufacturer may decide to use a lower light flash frequency or lower intensity, or the combination of both, for the same user in the later part of the sleep when the homeostatic sleep pressure dissipates and therefore easier for the user to wake up.

In an embodiment, the frequency of the flash is limited to once every 6 seconds to once per 120 seconds. In one embodiment, the frequency of the flash is set at once every 6 to 12 seconds, once every 12 to 15 seconds, once every 15 to 20 seconds, or once every 20-30 seconds. In one embodiment, the frequency of flashes may be adjusted based on sensor reading on the sleep/wake status or the sleep stage information from the user. The flash frequency may be a constant number throughout the course of treatment, or can change throughout the course of the treatment as part of a pre-designed treatment protocol, or responding to the feedback from the users via user input or sensors in the device. For example, in one embodiment, the system may cause a light flash in block B1 to be once every 7 seconds, followed by a block B2 with light flashes of once every 60 seconds, which will then followed by a block B3 of once every 12 seconds. Alternatively or additionally, there may be one or more blocks with no flash. In one embodiment, one or more blocks may contain continuous light instead of light flashes with certain frequency. In an embodiment, any of the frequencies disclosed in this specification may be used, and may be applied for 30 minutes off, 30 minutes on, and then 30 minutes off or for another number of minutes on and off. In an embodiment, when turning the flashes on for a period and then turning the flashes off for another period of time, the total number of minutes to treatment (the sum of Ws of all the blocks B with light flashes) may be limited to 5 minutes to 3.5 hours. In an embodiment, the on/off periods are not necessarily equal.

In an embodiment, the frequency is automatically varied (to create "dynamic" frequency treatment) during the treatment period, based on sleep/wake and/or sleep stages computed based on theoretical analysis and/or using data collected from sensor readings. According to how the user sleeps at different times, there are an unlimited number of combinations of frequencies during different periods and the durations of each period have any given frequency. Optionally, the length of periods (blocks) with light flashes and without light flashes and the flash frequency within each block can be dynamically changed, determined in real time while the user is sleeping and receiving the circadian adjustment treatment, based on data captured by the sensors. For example, a block of light flashes may be canceled temporarily if nocturnal awakenings were detected.

The manufacturer may provide a default setting of light flash durations. Since light flash duration is unlikely to affect the magnitude of circadian phase shift, the manufacturer may provide a default value of the shortest light flash duration that can be achieved by the hardware design (e.g. between 1 nanosecond to 1 microsecond, or between 1 microsecond to 100 microseconds). In one embodiment, the light flash duration may be set by settings that result in a light flash of between about 100 microseconds and 500 microseconds. In another embodiment, the light flash duration may be set by settings that result in a light flash of between 500 microseconds to 1 millisecond. In another embodiment, the light flash duration is set a value between 1 millisecond to 5 milliseconds. In an embodiment, the flash duration may be 10 microseconds to 100 microseconds, 100 microseconds to 1 millisecond, 500 microseconds to 3 milliseconds, or 10 microseconds to 10 milliseconds. In an embodiment, the flash duration maybe 1 nanosecond to 1 microsecond. In one embodiment, the manufacturer may provide settings for the user to adjust the flash duration.

Any frequency or range of frequencies may be used with any intensity or range of intensities, any color or range of wave length of color, any flash duration or range of flash duration, treatment period or range of treatment periods, every treatment pattern of changes in frequency and/or on/off periods may be used together with one another. The manufacturer may provide a default combination of light flash parameters based on the user's biological profile. For example, for users with the combination of certain biological traits that result in high light sensitivity, the manufacturer may provide an initial setting of light flashes of 100-500 microseconds at 100 lux (or 50 lux) at eye level before eyelid penetration at once per 30 seconds in frequency. For users with the combination of certain biological traits that result in low light sensitivity, the manufacturer may provide an initial setting of light flashes of 100-500 microseconds at 3000 lux (or 5000 lux) at eye level before eyelid penetration at once per 7 seconds in frequency. For users with biological profile that indicates intermediate light sensitivity, the manufacturer may provide an initial setting of light flashes of 100-500 microseconds with intensity and frequency between the previous two groups. In an embodiment, the values of parameters have a tolerance of 10% of the value specified.

FIG. 17 shows an exemplary method 1700 for selecting light treatment parameters. For example, it may be desirable for a system to select light treatment parameters that achieve a desired amount of circadian phase shifts while mitigating the risk of sleep disruptions. Method 1700 may be combined with any of the methods described herein, including those described above with reference to FIGS. 14, 15, and 16. By combining method 1700 with those described in FIGS. 14, 15, and 16, treatment efficacy may advantageously be improved, while minimizing sleep disruptions that could reduce compliance with a proscribed treatment regimen.

Higher light pulse intensity, duration, and/or frequency may desirably increase an amount of phase shift, but may undesirably increase the risk of sleep disruption. Thus, it may be desirable to determine parameters for light intensity, duration, and frequency that are simultaneously sufficiently high to achieve substantial phase shift and sufficiently low to avoid disrupting the user's sleep. In step 1702, the system obtains data that may indicate or impact the user's sensitivity to light during sleep. The inputs for the model may include any one of, or any combination of, age, sex, eye colors, pupillometry, light sensitivity, self-rated how light sleeper the user is, typical sleep quality, typical hours of sleep, typical sleep efficiency, current sleep problems such as insomnia or environmental disruptions. In at least one embodiment, the system may ask the user to provided self-rated light sensitivity in predetermined categories. In one embodiment, the system may provide a hardware and/or software user-interface to measure the user's light sensitivity. In one embodiment, the user may be asked to answer questions that may provide information about the user's light sensitivities, for example, how they typically respond to different levels of light during sleep or wakefulness.

In step 1706, the system may compare the user's light sensitivity data against calibration data. In some embodiments, the calibration data may indicated relationships between light sensitivity and one or more values for light flash duration, light flash frequency, and/or light flash intensity determined to present an acceptably low likelihood of disrupting sleep. In some embodiments, the system may interpret the light sensitivity data collected from step 1702. The system may compare the user's data against existing data for calibration, data that may indicate the user's light sensitivity, and/or data that directly or indirectly suggest the likelihood of sleep disruption with certain light treatment programs. For example, in at least one embodiment, the system may suggest a light sensitivity category for the user based on the user's biological profile (such as age and/or eye color) and self-reported light sensitivity and how heavy a sleeper the user is. In one embodiment, the data and interpretation may be based on results from lab studies or other human-subject studies with look-alike populations to investigate the effect of light flash frequency and sleep disruption. In one embodiment, the data may be collected from the feedback provided by the pool of look-alike demographic of users using the circadian rhythm adjustment system. In one embodiment, the initial interpretation of light sensitivity may be based on hypothesis, based on which a set of light program parameters are chosen. The light settings may then be adjusted based on the user's feedback. The system may assign a value (for example, 1-5 to indicate high sensitivity to low sensitivity) to indicate the user's light sensitivity level as part of the user's long-term profile.

Step 1706 may also include determining one or more values for the light programs, including light flash duration, light flash frequency, and/or light flash intensity to present an acceptably low likelihood of disrupting sleep while maintaining the potential of causing substantial circadian phase shifts for the user according to the user's light sensitivity value, to achieve the balance of substantial circadian phase shifts without increasing the risk of sleep disruptions. The instructions to activate the light source may specify the light intensity, duration, wavelength, frequency, and timing that likely works with users with certain assigned light sensitivity value. In one embodiment, the data may be based on results from lab studies or other human-subject studies with look-alike populations to investigate the effect of light flash frequency and sleep disruption. For example, a database accumulated through human-subject studies may indicate that, for users with certain biological or demographic indicators (e.g., age, sex, eye color, self-reports on how heavily the user sleeps), light flashes of specified intensity, duration, and/or frequency values may present an acceptably low risk of disrupting the user's sleep. In another embodiment, the values of the light program parameters may be directly specified, or through some linear or non-linear conversions. For example, in at least one embodiment, the system may provide a default light flash frequency of once per minute for user with combination of certain biological traits that result in high light sensitivity, and a default light flash frequency of once per 8 seconds for user with combination of certain biological traits that result in low light sensitivity, and values in between for users with combination of certain biological traits that result in intermediate light sensitivity. In at least one embodiment, the system may provide a default intensity of 100 lux or even 50 lux at eyelid level before eyelid penetration for user with combination of certain biological traits that result in high light sensitivity, and a default intensity of 3000 lux or even 5000 lux eyelid level before eyelid penetration for user with combination of certain biological traits that result in low light sensitivity, and values in between for users with combination of certain biological traits that result in intermediate light sensitivity. The user may adjust the light intensity setting to anywhere between 300, 600, 1000, or even 3000 lux at eyelid level before penetration based on system feedback or the user's own experiencing using the device. In one embodiment, the system may use a lower light flash frequency or lower intensity, or the combination of both, for users with higher sensitivity to light during sleep, and a higher light flash frequency or higher intensity, or the combination of both, for users with lower sensitivity to light during sleep. In one embodiment, the system may provide a set of default light flash frequencies used at different times of the sleep for the same user to achieve the most substantial circadian phase shift without causing sleep disruptions. For example, the manufacturer may decide to use a lower light flash frequency or lower intensity, or the combination of both, for the same user in the later part of the sleep when the homeostatic sleep pressure dissipates and it is therefore easier for the user to wake up. In at least one embodiment, the light program parameters to achieve the balance of substantial circadian phase shifts without increasing the risk of sleep disruptions may be determined based on the user's self-reported sleep challenges. For example, the timing of light program may be delayed if the user reports significantly longer sleep onset latency compared to populational baseline data. In at least one embodiment, the light program parameters to achieve the balance of substantial circadian phase shifts without increasing the risk of sleep disruptions may be determined based on the sleep and wake data collected via sensors in the circadian rhythm adjustment system or other wearables or sleep trackers.

In step 1708, based on at least the light sensitivity data and the calibration data, the system may then generate instructions for activating a light source to adjust the user's circadian rhythm using a processor system comprising one or more processors. For example, the system may generate instructions that specify one or more windows of light flashes having intensity, duration, and/or frequency values that are determined, based on the calibration data, to present an acceptably low of disrupting the user's sleep. The values may also be determined, based on the calibration data, to present an acceptably high likelihood of achieving a desired level of circadian phase shift. The instructions may also be based on the data sources and models described above with reference to FIGS. 14, 15, and 16. For example, the instructions may also be based on one or more models for estimating circadian rhythm and/or homeostatic sleep drive. In some embodiments, the instructions may specify for light flashes to be applied that have an intensity between 25 and 5,000 lux and a duration between 1 picosecond and 500 milliseconds. The instructions may also specify that the light flashes should be applied at a frequency between once per 5 seconds and once per 120 seconds. The instructions may specify that the light flashes should be applied during one or more treatment windows selected to achieve a desired shift to the user's circadian rhythm. This selection may be made based on, e.g., estimates for the user's PRC, circadian rhythm, and/or homeostatic sleep drive.

The instructions to activate light program for circadian rhythm misalignment treatment in step 1708 may be sent to the circadian rhythm adjustment apparatus to deliver the treatment program, which is shown in optional step 1710. Based on the instructions, the circadian rhythm adjustment apparatus may activate the light source (e.g. an LED) during a treatment window to adjust the user's circadian rhythm. In at least one embodiment, the treatment program may be delivered via a sleep mask that emits light flashes through a removable insert with electronics. In another embodiment, the light programs can be delivered in glasses or goggles. In one embodiment, the circadian rhythm treatment apparatus may include in-room lighting (controlled by a controller) that works with a mobile application that generates light programs based on circadian modeling algorithms to treat or prevent circadian rhythm disorders. In at least one embodiment, the light pulses use light sources that produces a wavelength between 380 to 750 nm. In at least one embodiment, a subset of the wavelength 380 to 750 nm for a specific segment of the light treatment, so different treatment segments may have different color. For example, a wavelength 380 to 750 nm may be used for the circadian rhythm adjustment program during sleep, a wavelength 600 to 750 nm may be used for the treatment towards the end of sleep, and wavelengths 380 to 550 nm may be used for treatment before bed, or a combination of different subsets of the color spectrum within one treatment segment.

Step 1712 describe an optional adjustment step, in which based on updated information, light program parameters may be adjusted to improve circadian rhythm alignment efficacy and/or to further reduce the risk of sleep disruptions. The system may recalculate any one of, or any combination of, the user's light program parameters such as intensity, frequency, duration, wavelength, and timing, based on updated information. In at least one embodiment, the system may reduce the light intensity, frequency, or duration, or the combination of all, if the system detects or the user reports sleep disruptions during the light program. In at least one embodiment, the system may increase the intensity, frequency, or duration, or the combination of all, if the system detects good sleep quality or alertness from sleep-monitoring sensors, neurocognitive testing, and/or from self-reported survey answers. In at least one embodiment, the system may increase the light intensity, pulse duration, and/or frequency if the user reports excess sleepiness at a time indicating that the expected shift to the user's circadian rhythm has not been achieved. In at least one embodiment, the user may be provided with settings that may increase or decrease the light intensity, frequency, or duration, or the combination of all, according to the data collected in the feedback step and or how they feel throughout the treatment program. Optional step 1712 may be performed using any of the exemplary details described above with respect to step 1516.

NUMBERED EMBODIMENTS

A1. A system for adjusting a user's circadian rhythm, the system comprising:
one or more input modules for collecting information relating to a user's sleep and/or wakefulness; a light source;
a processor system including one or more processors that control the light source;
a memory system storing one or more machine instructions, wherein the system is configured to:
obtain information relating to the user's present circadian rhythm;
obtain information relating to one or more anticipated times of sleep and/or wakefulness, for the user, on one or more days;
based on at least the information relating to the user's present circadian rhythm, generate a model for estimating the user's circadian rhythm over one or more days, the estimates of the user's circadian rhythm being configured to be adjusted in response to application, or anticipated application, of light by the light source;
based on at least the one or more anticipated times of sleep and/or wakefulness, generate a model for estimating the user's homeostatic sleep drive over one or more days, the estimates of the user's homeostatic sleep drive being configured to be adjusted in response to changes in the user's sleep and wakefulness times; and
based on at least the model for estimating the user's circadian rhythm and the model for estimating the user's homeostatic sleep drive, generate instructions for activating the light source to adjust the user's circadian rhythm.

A2. The system of embodiment A1, wherein the information relating to the user's sleep and/or wakefulness is collected, at least in part, using a sensor.

A3. The system of embodiment A2, wherein the sensor is a light sensor, the light sensor being configured to sense the user's exposure to environmental light.

A4. The system of embodiment A2, wherein the sensor is a motion sensor, the system being configured to estimate whether a user is sleeping or awake based on data obtained from the motion sensor.

A5. The system of embodiment A2, wherein the sensor is a capacitive sensor, the system being configured to determine whether a device is being worn by the user based on data obtained from the capacitive sensor.

A6. The system of any of embodiments A1-A5, wherein the system is further configured to:

based on the generated instructions for activating the light source, activate the light source during a treatment window while the user sleeps to adjust the user's circadian rhythm;

after applying the light source during the treatment window, obtain subsequent information; and based on the subsequent information, modify the instructions for activating the light source.

A7. The system of embodiment A6, wherein the subsequent information is user feedback relating to information about updated sleep and/or wakefulness schedules, device usage in previous days/nights, and/or the efficacy of the light application during at least the treatment window.

A8. The system of embodiment A6, wherein the subsequent information is obtained by at least one of a light sensor, a motion sensor, and a capacitive sensor.

A9. The system of any of embodiments A1-A8, wherein the system is further configured to:

determine recommended sleep times, the recommended sleep times being selected to achieve a desired shift to the user's circadian rhythm;

display to the user the recommended sleep times;

receive, from the user, feedback relating to the recommended sleep times; and based on the feedback, adjust the recommended sleep times.

A10. The system of any of embodiments A1-A9, wherein the system comprises a sleep mask, the light being applied during the user's sleep via the sleep mask.

A11. The system of any of embodiments A1-A10, wherein the instructions for activating the light source comprise instructions to activate the light source in one or more pulses having an intensity between 25 and 5,000 lux and a duration between 1 picosecond and 500 milliseconds.

B1. A method for adjusting a user's circadian rhythm, the method comprising:

obtaining information relating to the user's present circadian rhythm;

obtaining information relating to one or more anticipated times of sleep and/or wakefulness, for the user, on one or more days;

based on at least the information relating to the user's circadian rhythm, generating a model for estimating the user's circadian rhythm over one or more days, the estimates of the user's circadian rhythm being configured to be adjusted in response to application, or anticipated application, of light by the light source;

based on at least the one or more anticipated times of sleep and/or wakefulness, generating a model for estimating the user's homeostatic sleep drive over one or more days, the estimates of the user's homeostatic sleep drive being configured to be adjusted in response to changes in the user's sleep and wakefulness times; and based on at least the model for estimating the user's circadian rhythm and the model for estimating the user's homeostatic sleep drive, generating instructions for activating the light source to adjust the user's circadian rhythm.

B2. The method of embodiment B 1, wherein the information relating to the user's sleep and/or wakefulness is collected, at least in part, using a sensor.

B3. The method of embodiment B2, wherein the sensor is a light sensor, the light sensor being configured to sense the user's exposure to environmental light.

B4. The method of embodiment B2, wherein the sensor is a motion sensor, the method further comprising estimating whether the user is sleeping or awake based on data obtained from the motion sensor.

B5. The method of embodiment B2, wherein the sensor is a capacitive sensor, the method further comprising determining whether a device is being worn by the user based on data obtained from the capacitive sensor.

B6. The method of any of embodiments B1-B5, the method further comprising:

based on the generated instructions for activating the light source, activating the light source during a treatment window while the user sleeps to adjust the user's circadian rhythm;

after applying the light source during the treatment window, obtaining subsequent information; and based on the subsequent information, modifying the instructions for activating the light source.

B7. The method of embodiment B6, wherein the subsequent information is user feedback relating to information about updated sleep and/or wakefulness schedules, device usage in previous days/nights, and/or the efficacy of the light application during at least the treatment window.

B8. The method of embodiment B6, wherein the subsequent information is obtained by at least one of a light sensor, a motion sensor, and a capacitive sensor.

B9. The method of any of embodiments B1-B8, wherein the method further comprises:

determining recommended sleep times, the recommended sleep times being selected to achieve a desired shift to the user's circadian rhythm;

displaying to the user the recommended sleep times;

receiving, from the user, feedback relating to the recommended sleep times; and based on the feedback, adjusting the recommended sleep times.

B10. The method of any of embodiments B1-B9, wherein the method further comprises applying light in accordance with the generated instructions via a sleep mask while the user sleeps.

B11. The method of any of embodiments B1-B10, wherein the instructions for activating the light source comprise instructions to activate the light source in one or more pulses having an intensity between 25 and 5,000 lux and a duration between 1 picosecond and 500 milliseconds.

C1. A system for adjusting a user's circadian rhythm, the system comprising:

one or more input modules for collecting sleep data;

a light source;

a sensor, the sensor being configured to detect information relating to a user's sleep and/or wakefulness;

a processor system including one or more processors that controls the light source;

a memory system storing one or more machine instructions, wherein the system is configured to: using the sensor, obtain information relating to times of sleep and/or wakefulness;

based on at least the information relating to the user's times of sleep and/or wakefulness, generate a model for estimating the user's circadian rhythm over one or more days, the estimates of the user's circadian rhythm being configured to be adjusted in response to application, or anticipated application, of light by the light source; and based on at least the model for estimating the user's circadian rhythm, generate instructions for activating the light source to adjust the user's circadian rhythm.

C2. The system of embodiment C1, wherein the instructions for activating the light source are also based, at least in part, on a model for estimating the user's homeostatic sleep drive over one or more days, the estimates of the user's homeostatic sleep drive being configured to be adjusted in response to changes in the user's sleep and wakefulness times.

C3. The system of any of embodiments C1-C2, wherein the sensor is a light sensor, the light sensor being configured to sense the user's exposure to environmental light.

C4. The system of any of embodiment C1-C2, wherein the sensor is a motion sensor, the system being configured to estimate whether a user is sleeping or awake based on data obtained from the motion sensor.

C5. The system of any of embodiments C1-C2, wherein the sensor is a capacitive sensor, the system being configured to determine whether a device is being worn by the user based on data obtained from the capacitive sensor.

C6. The system of any of embodiments C1-05, wherein the system is further configured to:

based on the generated instructions for activating the light source, activate the light source during a treatment window while the user sleeps to adjust the user's circadian rhythm;

after applying the light source during the treatment window, obtain subsequent information; and based on the subsequent information, modify the instructions for activating the light source.

C7. The system of embodiment C6, wherein the subsequent information is user feedback relating to information about device usage in previous days/nights and/or the efficacy of the light application during at least the treatment window.

C8. The system of embodiment C6, wherein the subsequent information is obtained by at least one of a light sensor, a motion sensor, and a capacitive sensor.

C9. The system of any of embodiments C1-C8, wherein the system is further configured to:

determine recommended sleep times, the recommended sleep times being selected to achieve a desired shift to the user's circadian rhythm;

display to the user the recommended sleep times;

receive, from the user, feedback relating to the recommended sleep times; and based on the feedback, adjust the recommended sleep times.

C10. The system of any of embodiments C1-C9, wherein the system comprises a sleep mask, the light being applied during the user's sleep via the sleep mask.

C11. The system of any of embodiments C1-C10, wherein the instructions for activating the light source comprise instructions to activate the light source in one or more pulses having an intensity between 25 and 5,000 lux and a duration between 1 picosecond and 500 milliseconds.

D1. A method for adjusting a user's circadian rhythm, the method comprising:

using a sensor, obtain information relating to times of sleep and/or wakefulness;

based on at least the information relating to the user's times of sleep and/or wakefulness, generate a model for estimating the user's circadian rhythm over one or more days, the estimates of the user's circadian rhythm being configured to be adjusted in response to application, or anticipated application, of light by the light source; and based on at least the model for estimating the user's circadian rhythm, generate instructions for activating the light source to adjust the user's circadian rhythm.

D2. The method of embodiment D1, wherein the instructions for activating the light source are also based, at least in part, on a model for estimating the user's homeostatic sleep drive over one or more days, the estimates of the user's homeostatic sleep drive being configured to be adjusted in response to changes in the user's sleep and wakefulness times.

D3. The method of any of embodiments D1-D2, wherein the sensor is a light sensor, the light sensor being configured to sense the user's exposure to environmental light.

D4. The method of any of embodiment D1-D2, wherein the sensor is a motion sensor, the method further comprising estimating whether the user is sleeping or awake based on data obtained from the motion sensor.

D5. The method of any of embodiments D1-D2, wherein the sensor is a capacitive sensor, the method further comprising determining whether a device is being worn by the user based on data obtained from the capacitive sensor.

D6. The method of any of embodiments D1-D5, wherein the method further comprises:

based on the generated instructions for activating the light source, activating the light source during a treatment window while the user sleeps to adjust the user's circadian rhythm;

after applying the light source during the treatment window, obtaining subsequent information; and based on the subsequent information, modifying the instructions for activating the light source.

D7. The method of embodiment D6, wherein the subsequent information is user feedback relating to information about device usage in previous days/nights and/or the efficacy of the light application during at least the treatment window.

D8. The method of embodiment D6, wherein the subsequent information is obtained by at least one of a light sensor, a motion sensor, and a capacitive sensor.

D9. The method of any of embodiments D1-D8, wherein the method further comprises:

determining recommended sleep times, the recommended sleep times being selected to achieve a desired shift to the user's circadian rhythm;

displaying to the user the recommended sleep times;

receiving, from the user, feedback relating to the recommended sleep times; and based on the feedback, adjusting the recommended sleep times.

D10. The method of any of embodiments D1-D9, wherein the method comprises applying light in accordance with the generated instructions via a sleep mask while the user sleeps.

D11. The method of any of embodiments D1-D10, wherein the instructions for activating the light source comprise instructions to activate the light source in one or more pulses having an intensity between 25 and 5,000 lux and a duration between 1 picosecond and 500 milliseconds.

E1. A system for adjusting a user's circadian rhythm, the system comprising:
one or more input modules for collecting sleep data;
a light source;
a processor system including one or more processors that controls the light source;
a memory system storing one or more machine instructions, wherein the system is configured to:
obtain information relating to times of sleep and/or wakefulness for the user;
based on at least the information relating to the user's times of sleep and/or wakefulness, generate a model for estimating the user's circadian rhythm over one or more days, the estimates of the user's circadian rhythm being configured to be adjusted in response to application, or anticipated application, of light by the light source;
based on at least the model for estimating the user's circadian rhythm, generate instructions for activating the light source to adjust the user's circadian rhythm;
using the instructions, activate the light source to adjust the user's circadian rhythm;
obtain efficacy information relating to an efficacy of the instructions for activating the light source to adjust the user's circadian rhythm; and
based on at least the efficacy information, adjusting the instructions for activating the light source to adjust the user's circadian rhythm.

E2. The system of embodiment E1, wherein the information relating to the user's sleep and/or wakefulness is collected, at least in part, using a sensor.

E3. The system of embodiment E2, wherein the sensor is a light sensor, the light sensor being configured to sense the user's exposure to environmental light.

E4. The system of embodiment E2, wherein the sensor is a motion sensor, the system being configured to estimate whether a user is sleeping or awake based on data obtained from the motion sensor.

E5. The system of embodiment E2, wherein the sensor is a capacitive sensor, the system being configured to determine whether a device is being worn by the user based on data obtained from the capacitive sensor.

E6. The system of any of embodiments E1-E5, wherein the instructions for activating the light source are also based, at least in part, on a model for estimating the user's homeostatic sleep drive over one or more days, the estimates of the user's homeostatic sleep drive being configured to be adjusted in response to changes in the user's sleep and wakefulness times.

E7. The system of any of embodiments E1-E6, wherein the efficacy information is user feedback relating to the efficacy of the light application during at least the treatment window.

E8. The system of any of embodiments E1-E6, wherein the efficacy information is obtained by at least one of a light sensor, a motion sensor, and a capacitive sensor.

E9. The system of any of embodiments E1-E8, wherein the system is further configured to:
determine recommended sleep times, the recommended sleep times being selected to achieve a desired shift to the user's circadian rhythm;
display to the user the recommended sleep times;
receive, from the user, feedback relating to the recommended sleep times; and
based on the feedback, adjust the recommended sleep times.

E10. The system of any of embodiments E1-E9, wherein the system comprises a sleep mask, the light being applied during the user's sleep via the sleep mask.

E11. The system of any of embodiments E1-E10, wherein the instructions for activating the light source comprise instructions to activate the light source in one or more pulses having an intensity between 25 and 5,000 lux and a duration between 1 picosecond and 500 milliseconds.

F1. A method for adjusting a user's circadian rhythm, the method comprising:
obtaining information relating to times of sleep and/or wakefulness for the user;
based on at least the information relating to the user's times of sleep and/or wakefulness, generating a model for estimating the user's circadian rhythm over one or more days, the estimates of the user's circadian rhythm being configured to be adjusted in response to application, or anticipated application, of light by the light source;
based on at least the model for estimating the user's circadian rhythm, generating instructions for activating the light source to adjust the user's circadian rhythm;
using the instructions, activating the light source during a treatment window to adjust the user's circadian rhythm;
obtain efficacy information relating to an efficacy of the instructions for activating the light source during at least the treatment window; and
based on at least the efficacy information, adjusting the instructions for activating the light source to adjust the user's circadian rhythm.

F2. The method of embodiment F 1, wherein the information relating to the user's sleep and/or wakefulness is collected, at least in part, using a sensor.

F3. The method of embodiment F2, wherein the sensor is a light sensor, the light sensor being configured to sense the user's exposure to environmental light.

F4. The method of embodiment F2, wherein the sensor is a motion sensor, the method further comprising estimating whether the user is sleeping or awake based on data obtained from the motion sensor.

F5. The method of embodiment F2, wherein the sensor is a capacitive sensor, the method further comprising determining whether a device is being worn by the user based on data obtained from the capacitive sensor.

F6. The method of any of embodiments F1-F5, wherein the instructions for activating the light source are also based, at least in part, on a model for estimating the user's homeostatic sleep drive over one or more days, the estimates of the user's homeostatic sleep drive being configured to be adjusted in response to changes in the user's sleep and wakefulness times.

F7. The method of any of embodiments F1-F6, wherein the efficacy information is user feedback relating to the efficacy of the light application during at least the treatment window.

F8. The method of any of embodiments F1-F6, wherein the efficacy information is obtained by at least one of a light sensor, a motion sensor, and a capacitive sensor.

F9. The method of any of embodiments F1-F8, wherein the method further comprises:

determining recommended sleep times, the recommended sleep times being selected to achieve a desired shift to the user's circadian rhythm;

displaying to the user the recommended sleep times;

receiving, from the user, feedback relating to the recommended sleep times; and based on the feedback, adjusting the recommended sleep times.

F10. The method of any of embodiments F1-F9, wherein the method comprises applying light in accordance with the generated instructions via a sleep mask while the user sleeps.

F11. The method of any of embodiments F1-F10, wherein the instructions for activating the light source comprise instructions to activate the light source in one or more pulses having an intensity between 25 and 5,000 lux and a duration between 1 picosecond and 500 milliseconds.

G1. A system for adjusting a user's circadian rhythm, the system comprising:

one or more input modules for collecting data;

a light source;

a processor system including one or more processors that controls the light source;

a memory system storing one or more machine instructions, wherein the system is configured to:

obtain light sensitivity data for a user, the light sensitivity data being probative of a user's light sensitivity during sleep;

compare the user's light sensitivity data against calibration data, the calibration data indicating relationships between light sensitivity and one or more values for light flash duration, light flash frequency, and/or light flash intensity determined to present an acceptably low likelihood of disrupting sleep;

based on at least the light sensitivity data and the calibration data, generate instructions for activating the light source to adjust the user's circadian rhythm, the activations of the light source applying flashes of light having a duration, frequency, and/or intensity values determined to present an acceptably low likelihood of disrupting the user's sleep.

G2. The system of embodiment G1, wherein the light sensitivity data comprises at least one of age, eye color, self-reported light sensitivity, and how heavily the user reports sleeping.

G3. The system of any of embodiments G1-G2, wherein the system is further configured to:

based on the generated instructions for activating the light source, activate the light source during a treatment window while the user sleeps to adjust the user's circadian rhythm;

after applying the light source during the treatment window, obtain subsequent information; and based on the subsequent information, modifying the instructions for activate the light source.

G4. The system of embodiment G3, wherein the subsequent information is user feedback relating to information about device usage in previous days/nights and/or the efficacy of the light application during at least the treatment window.

G5. The system of embodiment G3, wherein the subsequent information is obtained by at least one of a light sensor, a motion sensor, and a capacitive sensor.

G6. The system of any of embodiments G1-G5, wherein the instructions for activating the light source comprise instructions to activate the light source in one or more pulses having an intensity between 25 and 5,000 lux and a duration between 1 picosecond and 500 milliseconds.

G7. The system of any of embodiments G1-G6, wherein the instructions for activating the light source comprise instructions to activate the light source using pulses having a frequency between once per 5 seconds and once per 120 seconds.

G8. The system of any of embodiments G1-G7, wherein the calibration data is based on human-subject studies.

G9. The system of any of embodiments G1-G8, wherein the generated instructions for activating the light source specify that a treatment regimen for a night includes at least one higher-treatment phase and at least one lower-treatment phase, at least one of light flash intensity, frequency, and/or duration being greater during the higher-treatment phase than during the lower-treatment phase.

G10. The system of any of embodiments G1-G9, wherein the higher-treatment phase is applied before the lower-treatment phase, such that the user's homeostatic sleep drive is higher when the higher-treatment phase is applied than when the lower-treatment phase is applied.

G11. The system of any of embodiments G1-G10, wherein the system comprises a sleep mask, the light being applied during the user's sleep via the sleep mask.

H1. A method for adjusting a user's circadian rhythm, the method comprising:

obtaining, via one or more input modules, light sensitivity data for a user, the light sensitivity data being probative of a user's light sensitivity during sleep;

comparing the user's light sensitivity data against calibration data, the calibration data indicating relationships between light sensitivity and one or more values for light flash duration, light flash frequency, and/or light flash intensity determined to present an acceptably low likelihood of disrupting sleep;

based on at least the light sensitivity data and the calibration data, generate, using a processor system comprising one or more processors, instructions for activating a light source to adjust the user's circadian rhythm; and based on the generated instructions, apply, using the light source, flashes of light having duration, frequency, and/or intensity values determined to present an acceptably low likelihood of disrupting the user's sleep.

H2. The method of embodiment H1, wherein the light sensitivity data comprises at least one of age, eye color, self-reported light sensitivity, and how heavily the user reports sleeping.

H3. The method of any of embodiments H1-H2, wherein the method further comprises:

based on the generated instructions for activating the light source, activating the light source during a treatment window while the user sleeps to adjust the user's circadian rhythm;

after applying the light source during the treatment window, obtain subsequent information; and based on the subsequent information, modifying the instructions for activate the light source.

H4. The method of embodiment H3, wherein the subsequent information is user feedback relating to information about device usage in previous days/nights and/or the efficacy of the light application during at least the treatment window.

H5. The method of embodiment H3, wherein the subsequent information is obtained by at least one of a light sensor, a motion sensor, and a capacitive sensor.

H6. The method of any of embodiments H1-H5, wherein the instructions for activating the light source comprise instructions to activate the light source in one or more pulses having an intensity between 25 and 5,000 lux and a duration between 1 picosecond and 500 milliseconds.

H7. The method of any of embodiments H1-H6, wherein the instructions for activating the light source comprise instructions to activate the light source using pulses having a frequency between once per 5 seconds and once per 120 seconds.

H8. The method of any of embodiments H1-H7, wherein the calibration data is based on human-subject studies.

H9. The method of any of embodiments H1-H8, wherein the generated instructions for activating the light source specify that a treatment regimen for a night includes at least one higher-treatment phase and at least one lower-treatment phase, at least one of light flash intensity, frequency, and/or duration being greater during the higher-treatment phase than during the lower-treatment phase.

H10. The method of any of embodiments H1-H9, wherein the higher-treatment phase is applied before the lower-treatment phase, such that the user's homeostatic sleep drive is higher when the higher-treatment phase is applied than when the lower-treatment phase is applied.

H11. The method of any of embodiments H1-H10, wherein the step of applying the light flashes is performed via a sleep mask.

ALTERNATIVES AND EXTENSIONS

Each embodiment disclosed herein may be used or otherwise combined with any of the other embodiments disclosed. Any element of any embodiment may be used in any embodiment.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

The invention claimed is:

1. A system for adjusting a user's circadian rhythm, the system comprising:
one or more input modules for collecting data;
a light source;
a processor system including one or more processors that controls the light source;
a memory system storing one or more machine instructions, wherein the system is configured to:
obtain light sensitivity data for a user, the light sensitivity data being probative of a user's light sensitivity during sleep;
compare the user's light sensitivity data against calibration data, the calibration data indicating relationships between light sensitivity and one or more values for light flash duration, light flash frequency, and/or light flash intensity determined to present an acceptably low likelihood of disrupting sleep; and
based on at least the light sensitivity data and the calibration data, generate instructions for activating the light source to adjust the user's circadian rhythm, the activations of the light source applying flashes of light having a duration, frequency, and/or intensity values determined to present an acceptably low likelihood of disrupting the user's sleep.

2. The system of claim 1, wherein the light sensitivity data comprises at least one of age, eye color, self-reported light sensitivity, and how heavily the user reports sleeping.

3. The system of claim 1, wherein the system is further configured to:
based on the generated instructions for activating the light source, activate the light source during a treatment window while the user sleeps to adjust the user's circadian rhythm;
after applying the light source during the treatment window, obtain subsequent information; and
based on the subsequent information, modifying the instructions for activate the light source.

4. The system of claim 3, wherein the subsequent information is user feedback relating to information about device usage in previous days/nights and/or the efficacy of the light application during at least the treatment window.

5. The system of claim 3, wherein the subsequent information is obtained by at least one of a light sensor, a motion sensor, and a capacitive sensor.

6. The system of claim 1, wherein the instructions for activating the light source comprise instructions to activate the light source in one or more pulses having an intensity between 25 and 5,000 lux and a duration between 1 picosecond and 500 milliseconds.

7. The system of claim 1, wherein the instructions for activating the light source comprise instructions to activate the light source using pulses having a frequency between once per 5 seconds and once per 120 seconds.

8. The system of claim 1, wherein the generated instructions for activating the light source specify that a treatment regimen for a night includes at least one higher-treatment phase and at least one lower-treatment phase, at least one of light flash intensity, frequency, and/or duration being greater during the higher-treatment phase than during the lower-treatment phase.

9. The system of claim 8, wherein the at least one higher-treatment phase is applied before the at least one lower-treatment phase, such that the user's homeostatic sleep drive is higher when the at least one higher-treatment phase is applied than when the at least one lower-treatment phase is applied.

10. The system of claim 1, wherein the system comprises a sleep mask, the light being applied during the user's sleep via the sleep mask.

11. A method for adjusting a user's circadian rhythm, the method comprising:
obtaining, via one or more input modules, light sensitivity data for a user, the light sensitivity data being probative of a user's light sensitivity during sleep;
comparing the user's light sensitivity data against calibration data, the calibration data indicating relationships between light sensitivity and one or more values for light flash duration, light flash frequency, and/or light flash intensity determined to present an acceptably low likelihood of disrupting sleep;
based on at least the light sensitivity data and the calibration data, generate, using a processor system comprising one or more processors, instructions for activating a light source to adjust the user's circadian rhythm; and based on the generated instructions, apply, using the light source, flashes of light having duration, frequency, and/or intensity values determined to present an acceptably low likelihood of disrupting the user's sleep.

12. The method of claim 11, wherein the light sensitivity data comprises at least one of age, eye color, self-reported light sensitivity, and how heavily the user reports sleeping.

13. The method of claim 11, wherein the method further comprises:

based on the generated instructions for activating the light source, activating the light source during a treatment window while the user sleeps to adjust the user's circadian rhythm;

after applying the light source during the treatment window, obtain subsequent information; and based on the subsequent information, modifying the instructions for activate the light source.

14. The method of claim 13, wherein the subsequent information is user feedback relating to information about device usage in previous days/nights and/or the efficacy of the light application during at least the treatment window.

15. The method of claim 13, wherein the subsequent information is obtained by at least one of a light sensor, a motion sensor, and a capacitive sensor.

16. The method of claim 11, wherein the instructions for activating the light source comprise instructions to activate the light source in one or more pulses having an intensity between 25 and 5,000 lux and a duration between 1 picosecond and 500 milliseconds.

17. The method of claim 11, wherein the instructions for activating the light source comprise instructions to activate the light source using pulses having a frequency between once per 5 seconds and once per 120 seconds.

18. The method of claim 11, wherein the generated instructions for activating the light source specify that a treatment regimen for a night includes at least one higher-treatment phase and at least one lower-treatment phase, at least one of light flash intensity, frequency, and/or duration being greater during the higher-treatment phase than during the lower-treatment phase.

19. The method of claim 18, wherein the at least one higher-treatment phase is applied before the at least one lower-treatment phase, such that the user's homeostatic sleep drive is higher when the at least one higher-treatment phase is applied than when the at least one lower-treatment phase is applied.

20. The method of claim 11, wherein the step of applying the light flashes is performed via a sleep mask.

* * * * *